US012600991B2

(12) United States Patent
Nakayashiki

(10) Patent No.: US 12,600,991 B2
(45) Date of Patent: Apr. 14, 2026

(54) GENETICALLY MODIFIED MICROORGANISM FOR PRODUCTION OF ASPARTIC ACID AND DOWNSTREAM METABOLITES FROM ASPARTIC ACID AS TARGET SUBSTANCE, AND METHOD FOR PRODUCING TARGET SUBSTANCE USING SAME

(71) Applicant: Green Earth Institute Co., Ltd., Tokyo (JP)

(72) Inventor: Toru Nakayashiki, Chiba (JP)

(73) Assignee: Green Earth Institute Co., Ltd., Tokyo (JP)

( * ) Notice: Subject to any disclaimer, the term of this patent is extended or adjusted under 35 U.S.C. 154(b) by 1118 days.

(21) Appl. No.: 17/602,998

(22) PCT Filed: Sep. 6, 2019

(86) PCT No.: PCT/JP2019/035286
§ 371 (c)(1),
(2) Date: Nov. 4, 2021

(87) PCT Pub. No.: WO2020/208842
PCT Pub. Date: Oct. 15, 2020

(65) Prior Publication Data

US 2022/0177924 A1 Jun. 9, 2022

(30) Foreign Application Priority Data

Apr. 12, 2019 (JP) ................................ 2019-076629

(51) Int. Cl.

| | |
|---|---|
| ***C12N 15/90*** | (2006.01) |
| ***C12N 5/10*** | (2006.01) |
| ***C12N 9/02*** | (2006.01) |
| ***C12N 9/04*** | (2006.01) |
| ***C12N 9/88*** | (2006.01) |
| ***C12N 15/52*** | (2006.01) |
| ***C12N 15/70*** | (2006.01) |
| ***C12N 15/77*** | (2006.01) |
| ***C12P 7/42*** | (2006.01) |
| ***C12P 7/46*** | (2006.01) |
| ***C12P 13/06*** | (2006.01) |
| ***C12P 13/20*** | (2006.01) |
| ***C12R 1/15*** | (2006.01) |
| ***C12R 1/19*** | (2006.01) |

(52) U.S. Cl.
CPC ............. *C12N 15/902* (2013.01); *C12N 5/10* (2013.01); *C12N 9/0006* (2013.01); *C12N 9/0008* (2013.01); *C12N 9/001* (2013.01); *C12N 9/88* (2013.01); *C12N 15/52* (2013.01); *C12N 15/70* (2013.01); *C12N 15/77* (2013.01); *C12P 7/42* (2013.01); *C12P 7/46* (2013.01); *C12P 13/06* (2013.01); *C12P 13/20* (2013.01); *C12R 2001/15* (2021.05); *C12R 2001/19* (2021.05); *C12Y 101/01027* (2013.01); *C12Y 102/05001* (2013.01); *C12Y 103/01006* (2013.01); *C12Y 103/05001* (2013.01); *C12Y 103/05004* (2013.01); *C12Y 401/01031* (2013.01); *C12Y 401/01032* (2013.01)

(58) Field of Classification Search
None
See application file for complete search history.

(56) References Cited

U.S. PATENT DOCUMENTS

| | | | |
|---|---|---|---|
| 2003/0100079 | A1 | 5/2003 | Mockel et al. |
| 2015/0376661 | A1 | 12/2015 | Zheng et al. |

FOREIGN PATENT DOCUMENTS

| | | |
|---|---|---|
| CN | 101023178 | 8/2007 |
| EP | 2495317 | 9/2012 |
| JP | H0870860 | 3/1996 |
| JP | 2001190297 | 7/2001 |
| JP | 2003503064 | 1/2003 |
| JP | 2006000091 | 1/2006 |
| JP | 2006254730 | 9/2006 |
| JP | 2006254795 | 9/2006 |
| JP | 2006320278 | 11/2006 |
| JP | 2007043947 | 2/2007 |
| JP | 2007514436 | 6/2007 |
| JP | 2008513023 | 5/2008 |
| JP | 2010183860 | 8/2010 |
| JP | 2013516958 | 5/2013 |
| JP | 2016506738 | 3/2016 |
| KR | 1020070065870 | 6/2007 |
| WO | 0100852 | 1/2001 |

(Continued)

OTHER PUBLICATIONS

Bornscheuer et al. Curr Protoc Protein Sci. Nov. 2011; Chapter 26: Unit26.7. (Year: 2011).*

(Continued)

*Primary Examiner* — Christian L Fronda
(74) *Attorney, Agent, or Firm* — JCIPRNET

(57) ABSTRACT

The present disclosure relates to a genetically modified microorganism satisfying some of predetermined conditions. The predetermined conditions include: (I) succinate dehydrogenase activity or fumarate reductase activity being reduced or inactivated relative to a wild-type microorganism; (II) lactate dehydrogenase activity being reduced or inactivated relative to the wild-type microorganism; (III) the genetically modified microorganism having modified phosphoenolpyruvate carboxylase activity showing resistance to feedback inhibition by aspartic acid in wild-type phosphoenolpyruvate carboxylase activity, or exogenous phosphoenolpyruvate carboxylase activity having higher resistance to feedback inhibition by aspartic acid than that of the wild-type phosphoenolpyruvate carboxylase activity shown by the wild-type microorganism; and (IV) pyruvate:quinone oxidoreductase being reduced or inactivated relative to the wild-type microorganism.

30 Claims, 8 Drawing Sheets

Specification includes a Sequence Listing.

(56) References Cited

FOREIGN PATENT DOCUMENTS

| | | |
|---|---|---|
| WO | 2005059154 | 6/2005 |
| WO | 2006034156 | 3/2006 |
| WO | 2011087139 | 7/2011 |

OTHER PUBLICATIONS

Yoshikuni et al. Curr Opin Chem Biol. Apr. 2007;11(2):233-9. (Year: 2007).*
Chica et al. Curr Opin Biotechnol. Aug. 2005;16(4):378-84. (Year: 2005).*
Singh et al. Curr Protein Pept Sci. 2017, 18, 1-11 (Year: 2017).*
Kizer et al. Appl Environ Microbiol. May 2008;74(10):3229-41. (Year: 2008).*
Prather et al. Curr Opin Biotechnol. Oct. 2008;19(5):468-74. (Year: 2008).*
"Office Action of China Counterpart Application" with English translation thereof, issued on Apr. 26, 2022, p. 1-p. 11.
"International Search Report (Form PCT/ISA/210) of PCT/JP2019/035286", mailed on Nov. 19, 2019, with English translation thereof, pp. 1-7.
Kento Tokuyama et al., "Application of adaptive laboratory evolution to overcome a flux limitation in an *Escherichia coli* production strain," Biotechnology and Bioengineering, Feb. 2018, pp. 1542-1551.
Masaru Wada et al., "Effects of phosphoenolpyruvate carboxylase desensitization on glutamic acid production in Corynebacterium glutamicum ATCC 13032," Journal of Bioscience and Bioengineering, Feb. 2016, pp. 172-177.
Zhen Chen et al., "Deregulation of Feedback Inhibition of Phosphoenolpyruvate Carboxylase for Improved Lysine Production in Corynebacterium glutamicum," Applied and Environmental Microbiology, Feb. 2014, pp. 1388-1393.
Masato Yano et al., "The Replacement of Lys620 by Serine Desensitizes *Escherichia coli* Phosphoenolpyruvate Carboxylase to the Effects of the Feedback Inhibitors I-aspartate and I-malate," European Journal of Biochemistry, Apr. 1997, pp. 74-81.
Satoshi Mitsuhashi et al., "Disruption of Malate:Quinone Oxidoreductase Increases L-Lysine Production by Corynebacterium glutamicum," Bioscience, Biotechnology, and Biochemistry, Nov. 2006, pp. 1-5.
"Notice of Reasons for Rejection of Japan Counterpart Application", issued on Apr. 14, 2023, with English translation thereof, p. 1-p. 8.
"Office Action of Japan Counterpart Application" with English translation thereof, issued on Nov. 7, 2022, p. 1-p. 13.
"Office Action of Korea Counterpart Application", issued on Feb. 13, 2024, with English translation thereof, p. 1-p. 8.
"Office Action of China Counterpart Application", issued on Sep. 30, 2022, with English translation thereof, pp. 1-10.
"Search Report of Europe Counterpart Application", issued on Nov. 3, 2022, pp. 1-13.
Tu Changsheng et al., "Biochemical Engineering," Light Industry Press, Dec. 1981, pp. 96-98.
"Office Action of China Counterpart Application" with English translation thereof, issued on Nov. 29, 2021, p. 1-p. 18.
Boris Litsanov et al., "Efficient aerobic succinate production from glucose in minimal medium with Corynebacterium glutamicum," Microbial Biotechnology, Sep. 2011, pp. 116-128.
Xiaoyu Piao et al., "Metabolic engineering of *Escherichia coli* for production of L-aspartate and its derivative β-alanine with high stoichiometric yield," Metabolic Engineering, vol. 54, Jul. 2019, pp. 244-254.
Masataka Nakamura et al., "Nucleotide sequence of the asnA gene coding for asparagine synthetase of *E. coli* K-12," Nucleic Acids Research, vol. 9, Sep. 1981, pp. 4669-4676.
Akio Sugiyama et al., "Overexpression and purification of asparagine synthetase from *Escherichia coli*," Biosci. Biotech. Biochem., Mar. 1992, pp. 376-379.
Keita Fukui et al., "Identification of succinate exporter in Corynebacterium glutamicum and its physiological roles under anaerobic conditions", Journal of Biotechnology, vol. 154, Mar. 2011, pp. 25-36.
Jiao Meng et al., "High-yield anaerobic succinate production by strategically regulating multiple metabolic pathways based on stoichiometric maximum in *Escherichia coli*", Microbial Cell Factories, Aug. 2016, pp. 1-13.
Deyu Xu et al., "Removal of Feedback Inhibition of Corynebacterium glutamicum Phosphoenolpyruvate Carboxylase by Addition of a Short Terminal Peptide," Biotechnology and Bioprocess Engineering, vol. 23, Mar. 2018, pp. 72-78.
"Search Report of Europe Counterpart Application", issued on Jul. 29, 2022, p. 1-p. 15.

* cited by examiner

FIG. 2A
FIG. 2B
FIG. 2C
Primer F2
ldh
Primer F3
Primer R2
Primer R3
sdhC
sdhB
Primer F4
sdhA
Primer F5
Primer R4
Primer R5
Primer F6
poxB
Primer F7
Primer R6
Primer R7

D299

```
                  310        320        330        340        350
              ....|....| ....|....| ....|....| ....|....| ....|....|
C. glutamicum       THRAAETVLK YYARQLHSLE HELSLSDRMN KVTPQLLALA DAGHNDVP--
C. ammoniagenes     TRQAADTVLE YYVDELALLE KELSLSDRYS ESSAELQELA ARGNNDVP--
C. callunae         TSRAAETVLK YYGRQLHTLE HELSLSDRMS SVTEELRELA DAGKNDVP--
C. doosanense       TQAAADTVLD YYDEQLGELE KELSLSDRYS ECSQELRELA DRGNNDVP--
C. efficiens        THRAAETVLK YYVKQLHALE HELSLSDRMN VISDELRVLA DAGQNDMP--
C. halotolerans     TRRAAQTVLK HYETQLLALE HELSLSDRMT SVTVDLVALA KRGLNDVP--
C. humireducens     SRRAAQTVLK YYVTQLHALE HELSLSDRMT SVTVELVALA GRGKNDVP--
C. marinum          SRRAAQTVLK HYSGELHALE HELSLSDRMT SVSVELVGLA ARGRNDVP--
C. pollutisoli      SRRAAQTVLK YYAQQLHALE HELSLSDRMT SVTVELVALA GKGRNDVP--
C. deserti          THRAAQTVLK YYTRQLHSLE HELSLSDRMN AVTQELSKLA DAGNNDVP--
Arthrobacter sp. PGP41  LQIQNQHAVR ISIGMIDELI SILSNSTALA GADQELLDSI DSDLKNLPGL
E. coli k-12        LLLSRWKATD LFLKDIQVLV SELSMVEATP ------ELLALV GEEGAAEP--
```

FIG. 3A

```
                  670        680        690        700        710        720
              ....|....| ....|....| ....|....| ....|....| ....|....| ....|....|
C. glutamicum       RGGGPSYDAI LAQPRGAVQG SVRITEQGEI ISAKYGNPET ARRNLEALVS ATLEASLLDV
C. ammoniagenes     RGGGPTYDAI LAQPEGAVRG SVRITEQGEV ISAKYGTATS ARRHLEAFVA GTLEASLLDT
C. callunae         RGGGPSYDAI LAQPKGAVRG SLRITEQGEI ISAKYGSPET ARRNLEALVS ATLEASLLDV
C. doosanense       RGGGPTYDAI LAQPVGAVRG SVRITEQGEV ISAHYGTATT ARRHLEAFVA GTLEASLLDT
C. efficiens        RGGGPSYDAI LAQPKGAVRG AVRVTEQGEI ISAKYGNPDT ARRNLEALVS ATLEASLLDD
C. halotolerans     RGGGPSYEAI LAQPKGAVDG SVRITEQGEI ISAKYGSGHT ARRNLEALVS ATLEASLLDV
C. humireducens     RGGGPSYDAL LAQPQGAVDG SVRITEQGEI ISAKYGSPRT ARRNLEALVS ATLEASLLTV
C. marinum          RGGGPSYEAI LAQPQGAVDG SVRITEQGEI ISAKYGSPRT ARRNLEALVS ATLEASLLPV
C. pollutisoli      RGGGPSYDAI LAQPQGAVDG SVRITEQGEI ISAKYGSERA ARRNLEALVS ATLEASLLTV
C. deserti          RGGGPSYDAI LAQPKGAVLG SVRITEQGEI ISAKYGNPET ARRNLEALVS ATLEATLLDV
Arthrobacter sp. PGP41  RGGGPTYDAI LAQPNGVLEG EIKFTEQGEV ISDKYSLPEL ARENLELSLA AVLQGSALHK
E. coli K-12        RGGAPAHAAL LSQPPGSLKG GLRVTEQGEM IRFKYGLPEI TVSSLSLYTG AILEANLLP~
```

FIG. 3B

```
                              K813
                          850       860       870       880       890       900
                      ....|....| ....|....| ....|....| ....|....| ....|....| ....|....|
C. glutamicum         SWPFFTSVLD NMAQVMSKAE LRLAKLYADL IPDTEVAERV YSVIREEYFL TKKMFCVITG
C. ammoniagenes       AWPFFRSVLD NMAQVMGKAS MDLAKIYSTL VDDAETSKRV FTTIVDEYEL TREVFHRITG
C. callunae           TWPFFTSVLD NMAQVMSKAE LRLAKLYSEL IPDREVAQRI YDVIFDEYFL TKEMFCVITG
C. doosanense         TWSFFRSVMD NMAQVMGKAS MDLARIYSTL VDDPEVSERV FSTIADEFEL TQSVFHRITG
C. efficiens          CWPFFTSVLD NMAQVMSKAE LRLARLYADL IPDREVADRI YETIFGEYFL TKEMFCTITG
C. halotolerans       TWPFFTSVMS NMAQVMSKAG MELAGLYAGL VDDREVAGRI RGIISEEFRL TREMFTKVTG
C. humireducens       SWPFFTSIMS NMAQVMSKAG MDLAELYARL IDDREVAERV HGVITEEFEL TREMFSTVTG
C. marinum            SWPFFASVMS NMAQVMSKAG MELAELYARL VDDREIADRI LGVISAEFDL TRQMFGVVTG
C. pollutisoli        TWPFFASIMS NMAQVMSKAG MDLAELYARL IDDREVADRV HGVITAEFEL TRGMFSTVTG
C. deserti            SWPFFTSVLD NMAQVMSKAE LRLAKLYADL IPDQEVAERI YTDIFEEYFL TKKMFCKITG
Arthrobacter sp. PGP41 NWHFFRSVLS NVEMTLAKTD LDIAGYYVST LVPEELHH-I FRSIREEYEL TVAEVQNLTG
E. coli K-12          DWPFFSTRLG MLEMVFAKAD LWLAEYYDQR LVDKALWP-L GKELRNLQEE DIKVVLAIAN

                          910 S869  920       930       940       950       960
                      ....|....| ....|....| ....|....| ....|....| ....|....| ....|....|
C. glutamicum         SDDLLDDNPL LARSVQRRYP YLLPLNVIQV EMMRRYRKGD QS-------- ---EQVSRNI
C. ammoniagenes       HESLMAGNER LERSVHRRYP YLLPLNAIQI ELLRRYRAGD DS-------- ---FLVSKTI
C. callunae           STDLLDENPL LARSVRSRFP YLLPLNVIQV EMMRRYRAGD ES-------- ---KGVSRNI
C. doosanense         HESLMAGNDR LERSVQRRYP YLLPLNAIQI ELLRRYRSGD DS-------- ---FLVSKTI
C. efficiens          SQDLLDDNPA LARSVRSRFP YLLPLNVIQV EMMRRYRSGD EG-------- ---TAVPRNI
C. halotolerans       SEDLLADNPM LARSVRRRFP YLLPLNIIQV ELLRRHRAGD ER-------- ---DAVSRGI
C. humireducens       SAELLADNPA LARSVRRRFP YLLPLNIIQL ELLRRHRAGD SR-------- ---RAVSRGI
C. marinum            SEDLLADNPA LARSVRRRFP YLLPLNIIQL EMLRRHRAGD DR-------- ---EVVSRGI
C. pollutisoli        SEELLADNPA LARSVRRRFP YLLPLNIIQL EMLRRHRAGD AR-------- ---QAVSRGI
C. deserti            SSDLLDDNPL LARSVQRRYP YLLPLNVIQV EMMRRFRSGD DS-------- ---DGISRNI
Arthrobacter sp. PGP41 ESLLLDAQPT LKRSLEIRDQ YLDPISYLQV ELLRRVRAEA ADAADGISGA EIDERLQRAM
E. coli K-12          DSHLMADLPW IAESIQLRNI YTDPLNVLQA ELLHRSRQAE KE------GQ EPDPRVEQAL
                                   R873
                          970
                      ....|....| ....|
C. glutamicum         QLTMNGLSTA LRNSG
C. ammoniagenes       QVTMNGLATG LRNSG
C. callunae           QLTMNGLATA LRNSG
C. doosanense         QVTMNGLATG LRNSG
C. efficiens          RLTMNGLSTA LRNSG
C. halotolerans       RLTMNGLATA LRNSG
C. humireducens       QLTMNGLATA LRNSG
C. marinum            QLTMNGLATA LRNSG
C. pollutisoli        QLTMNGLATA LRNSG
C. deserti            QLTMNGLSTA LRNSG
Arthrobacter sp. PGP41 LITVNGVAAG LRNTG
E. coli K-12          MVTIAGIAAG MRNTG
                         N917
```

FIG. 3C

SEQUENCE LISTING

```
<160> NUMBER OF SEQ ID NOS: 49

<210> SEQ ID NO 1
<211> LENGTH: 2870
<212> TYPE: DNA
<213> ORGANISM: Corynebacterium glutamicum
<220> FEATURE:
<221> NAME/KEY: CDS
<222> LOCATION: (78)..(2837)
<223> OTHER INFORMATION: Phosphoenolpyruvate_carboxylase_coding_region

<400> SEQUENCE: 1

aaacacctgt tttgctgggt gattttttat ctcatgcacg ccaacaccct caatgtgaaa     60

gagtgtttaa agtagtt atg act gat ttt tta cgc gat gac atc agg ttc       110
                   Met Thr Asp Phe Leu Arg Asp Asp Ile Arg Phe
                   1               5                   10

ctc ggt caa atc ctc ggt gag gta att gcg gaa caa gaa ggc cag gag      158
Leu Gly Gln Ile Leu Gly Glu Val Ile Ala Glu Gln Glu Gly Gln Glu
            15                  20                  25

gtt tat gaa ctg gtc gaa caa gcg cgc ctg act tct ttt gat atc gcc      206
Val Tyr Glu Leu Val Glu Gln Ala Arg Leu Thr Ser Phe Asp Ile Ala
        30                  35                  40

aag ggc aac gcc gaa atg gat agc ctg gtt cag gtt ttc gac ggc att      254
Lys Gly Asn Ala Glu Met Asp Ser Leu Val Gln Val Phe Asp Gly Ile
    45                  50                  55

act cca gcc aag gca aca ccg att gct cgc gca ttt tcc cac ttc gct      302
Thr Pro Ala Lys Ala Thr Pro Ile Ala Arg Ala Phe Ser His Phe Ala
60                  65                  70                  75
```

-continued

```
ctg ctg gct aac ctg gcg gaa gac ctc tac gat gaa gag ctt cgt gaa      350
Leu Leu Ala Asn Leu Ala Glu Asp Leu Tyr Asp Glu Glu Leu Arg Glu
                80                  85                  90

cag gct ctc gat gca ggc gac acc cct ccg gac agc act ctt gat gcc      398
Gln Ala Leu Asp Ala Gly Asp Thr Pro Pro Asp Ser Thr Leu Asp Ala
            95                  100                 105

acc tgg ctg aaa ctc aat gag ggc aat gtt ggc gca gaa gct gtg gcc      446
Thr Trp Leu Lys Leu Asn Glu Gly Asn Val Gly Ala Glu Ala Val Ala
        110                 115                 120

gat gtg ctg cgc aat gct gag gtg gcg ccg gtt ctg act gcg cac cca      494
Asp Val Leu Arg Asn Ala Glu Val Ala Pro Val Leu Thr Ala His Pro
    125                 130                 135

act gag act cgc cgc cgc act gtt ttt gat gcg caa aag tgg atc acc      542
Thr Glu Thr Arg Arg Arg Thr Val Phe Asp Ala Gln Lys Trp Ile Thr
140                 145                 150                 155

acc cac atg cgt gaa cgc cac gct ttg cag tct gcg gag cct acc gct      590
Thr His Met Arg Glu Arg His Ala Leu Gln Ser Ala Glu Pro Thr Ala
                160                 165                 170

cgt acg caa agc aag ttg gat gag atc gag aag aac atc cgc cgt cgc      638
Arg Thr Gln Ser Lys Leu Asp Glu Ile Glu Lys Asn Ile Arg Arg Arg
            175                 180                 185

atc acc att ttg tgg cag acc gcg ttg att cgt gtg gcc cgc cca cgt      686
Ile Thr Ile Leu Trp Gln Thr Ala Leu Ile Arg Val Ala Arg Pro Arg
        190                 195                 200

atc gag gac gag atc gaa gta ggg ctg cgc tac tac aag ctg agc ctt      734
Ile Glu Asp Glu Ile Glu Val Gly Leu Arg Tyr Tyr Lys Leu Ser Leu
    205                 210                 215

ttg gaa gag att cca cgt atc aac cgt gat gtg gct gtt gag ctt cgt      782
Leu Glu Glu Ile Pro Arg Ile Asn Arg Asp Val Ala Val Glu Leu Arg
220                 225                 230                 235

gag cgt ttc ggc gag ggt gtt cct ttg aag ccc gtg gtc aag cca ggt      830
Glu Arg Phe Gly Glu Gly Val Pro Leu Lys Pro Val Val Lys Pro Gly
                240                 245                 250

tcc tgg att ggt gga gac cac gac ggt aac cct tat gtc acc gcg gaa      878
Ser Trp Ile Gly Gly Asp His Asp Gly Asn Pro Tyr Val Thr Ala Glu
            255                 260                 265

aca gtt gag tat tcc act cac cgc gct gcg gaa acc gtg ctc aag tac      926
Thr Val Glu Tyr Ser Thr His Arg Ala Ala Glu Thr Val Leu Lys Tyr
        270                 275                 280

tat gca cgc cag ctg cat tcc ctc gag cat gag ctc agc ctg tcg gac      974
Tyr Ala Arg Gln Leu His Ser Leu Glu His Glu Leu Ser Leu Ser Asp
    285                 290                 295

cgc atg aat aag gtc acc ccg cag ctg ctt gcg ctg gca gat gca ggg     1022
Arg Met Asn Lys Val Thr Pro Gln Leu Leu Ala Leu Ala Asp Ala Gly
300                 305                 310                 315

cac aac gac gtg cca agc cgc gtg gat gag cct tat cga cgc gcc gtc     1070
His Asn Asp Val Pro Ser Arg Val Asp Glu Pro Tyr Arg Arg Ala Val
                320                 325                 330

cat ggc gtt cgc gga cgt atc ctc gcg acg acg gcc gag ctg atc ggc     1118
His Gly Val Arg Gly Arg Ile Leu Ala Thr Thr Ala Glu Leu Ile Gly
            335                 340                 345

gag gac gcc gtt gag ggc gtg tgg ttc aag gtc ttt act cca tac gca     1166
Glu Asp Ala Val Glu Gly Val Trp Phe Lys Val Phe Thr Pro Tyr Ala
        350                 355                 360

tct ccg gaa gaa ttc tta aac gat gcg ttg acc att gat cat tct ctg     1214
Ser Pro Glu Glu Phe Leu Asn Asp Ala Leu Thr Ile Asp His Ser Leu
    365                 370                 375

cgt gaa tcc aag gac gtt ctc att gcc gat gat cgt ttg tct gtg ctg     1262
Arg Glu Ser Lys Asp Val Leu Ile Ala Asp Asp Arg Leu Ser Val Leu
```

-continued

```
380                 385                 390                 395

att tct gcc atc gag agc ttt gga ttc aac ctt tac gca ctg gat ctg     1310
Ile Ser Ala Ile Glu Ser Phe Gly Phe Asn Leu Tyr Ala Leu Asp Leu
                400                 405                 410

cgc caa aac tcc gaa agc tac gag gac gtc ctc acc gag ctt ttc gaa     1358
Arg Gln Asn Ser Glu Ser Tyr Glu Asp Val Leu Thr Glu Leu Phe Glu
            415                 420                 425

cgc gcc caa gtc acc gca aac tac cgc gag ctg tct gaa gca gag aag     1406
Arg Ala Gln Val Thr Ala Asn Tyr Arg Glu Leu Ser Glu Ala Glu Lys
        430                 435                 440

ctt gag gtg ctg ctg aag gaa ctg cgc agc cct cgt ccg ctg atc ccg     1454
Leu Glu Val Leu Leu Lys Glu Leu Arg Ser Pro Arg Pro Leu Ile Pro
    445                 450                 455

cac ggt tca gat gaa tac agc gag gtc acc gac cgc gag ctc ggc atc     1502
His Gly Ser Asp Glu Tyr Ser Glu Val Thr Asp Arg Glu Leu Gly Ile
460                 465                 470                 475

ttc cgc acc gcg tcg gag gct gtt aag aaa ttc ggg cca cgg atg gtg     1550
Phe Arg Thr Ala Ser Glu Ala Val Lys Lys Phe Gly Pro Arg Met Val
                480                 485                 490

cct cac tgc atc atc tcc atg gca tca tcg gtc acc gat gtg ctc gag     1598
Pro His Cys Ile Ile Ser Met Ala Ser Ser Val Thr Asp Val Leu Glu
            495                 500                 505

ccg atg gtg ttg ctc aag gaa ttc gga ctc atc gca gcc aac ggc gac     1646
Pro Met Val Leu Leu Lys Glu Phe Gly Leu Ile Ala Ala Asn Gly Asp
        510                 515                 520

aac cca cgc ggc acc gtc gat gtc atc cca ctg ttc gaa acc atc gaa     1694
Asn Pro Arg Gly Thr Val Asp Val Ile Pro Leu Phe Glu Thr Ile Glu
    525                 530                 535

gat ctc cag gcc ggc gcc gga atc ctc gac gaa ctg tgg aaa att gat     1742
Asp Leu Gln Ala Gly Ala Gly Ile Leu Asp Glu Leu Trp Lys Ile Asp
540                 545                 550                 555

ctc tac cgc aac tac ctc ctg cag cgc gac aac gtc cag gaa gtc atg     1790
Leu Tyr Arg Asn Tyr Leu Leu Gln Arg Asp Asn Val Gln Glu Val Met
                560                 565                 570

ctc ggt tac tcc gat tcc aac aag gat ggc gga tat ttc tcc gca aac     1838
Leu Gly Tyr Ser Asp Ser Asn Lys Asp Gly Gly Tyr Phe Ser Ala Asn
            575                 580                 585

tgg gcg ctt tac gac gcg gaa ctg cag ctc gtc gaa cta tgc cga tca     1886
Trp Ala Leu Tyr Asp Ala Glu Leu Gln Leu Val Glu Leu Cys Arg Ser
        590                 595                 600

gcc ggg gtc aag ctt cgc ctg ttc cac ggc cgt ggt ggc acc gtc ggc     1934
Ala Gly Val Lys Leu Arg Leu Phe His Gly Arg Gly Gly Thr Val Gly
    605                 610                 615

cgc ggt ggc gga cct tcc tac gac gcg att ctt gcc cag ccc agg ggg     1982
Arg Gly Gly Gly Pro Ser Tyr Asp Ala Ile Leu Ala Gln Pro Arg Gly
620                 625                 630                 635

gct gtc caa ggt tcc gtg cgc atc acc gag cag ggc gag atc atc tcc     2030
Ala Val Gln Gly Ser Val Arg Ile Thr Glu Gln Gly Glu Ile Ile Ser
                640                 645                 650

gct aag tac ggc aac ccc gaa acc gcg cgc cga aac ctc gaa gcc ctg     2078
Ala Lys Tyr Gly Asn Pro Glu Thr Ala Arg Arg Asn Leu Glu Ala Leu
            655                 660                 665

gtc tca gcc acg ctt gag gca tcg ctt ctc gac gtc tcc gaa ctc acc     2126
Val Ser Ala Thr Leu Glu Ala Ser Leu Leu Asp Val Ser Glu Leu Thr
        670                 675                 680

gat cac caa cgc gcg tac gac atc atg agt gag atc tct gag ctc agc     2174
Asp His Gln Arg Ala Tyr Asp Ile Met Ser Glu Ile Ser Glu Leu Ser
    685                 690                 695

ttg aag aag tac gcc tcc ttg gtg cac gag gat caa ggc ttc atc gat     2222
```

```
Leu Lys Lys Tyr Ala Ser Leu Val His Glu Asp Gln Gly Phe Ile Asp
700                 705                 710                 715

tac ttc acc cag tcc acg ccg ctg cag gag att gga tcc ctc aac atc      2270
Tyr Phe Thr Gln Ser Thr Pro Leu Gln Glu Ile Gly Ser Leu Asn Ile
                720                 725                 730

gga tcc agg cct tcc tca cgc aag cag acc tcc tcg gtg gaa gat ttg      2318
Gly Ser Arg Pro Ser Ser Arg Lys Gln Thr Ser Ser Val Glu Asp Leu
            735                 740                 745

cga gcc atc cca tgg gtg ctc agc tgg tca cag tct cgt gtc atg ctg      2366
Arg Ala Ile Pro Trp Val Leu Ser Trp Ser Gln Ser Arg Val Met Leu
        750                 755                 760

cca ggc tgg ttt ggt gtc gga acc gca tta gag cag tgg att ggc gaa      2414
Pro Gly Trp Phe Gly Val Gly Thr Ala Leu Glu Gln Trp Ile Gly Glu
    765                 770                 775

ggg gag cag gcc acc caa cgc att gcc gag ctg caa aca ctc aat gag      2462
Gly Glu Gln Ala Thr Gln Arg Ile Ala Glu Leu Gln Thr Leu Asn Glu
780                 785                 790                 795

tcc tgg cca ttt ttc acc tca gtg ttg gat aac atg gct cag gtg atg      2510
Ser Trp Pro Phe Phe Thr Ser Val Leu Asp Asn Met Ala Gln Val Met
                800                 805                 810

tcc aag gca gag ctg cgt ttg gca aag ctc tac gca gac ctg atc cca      2558
Ser Lys Ala Glu Leu Arg Leu Ala Lys Leu Tyr Ala Asp Leu Ile Pro
            815                 820                 825

gat acg gaa gta gcc gag cga gtc tat tcc gtc atc cgc gag gag tac      2606
Asp Thr Glu Val Ala Glu Arg Val Tyr Ser Val Ile Arg Glu Glu Tyr
        830                 835                 840

ttc ctg acc aag aag atg ttc tgc gta atc acc ggc tct gat gat ctg      2654
Phe Leu Thr Lys Lys Met Phe Cys Val Ile Thr Gly Ser Asp Asp Leu
    845                 850                 855

ctt gat gac aac cca ctt ctc gca cgc tct gtc cag cgc cga tac ccc      2702
Leu Asp Asp Asn Pro Leu Leu Ala Arg Ser Val Gln Arg Arg Tyr Pro
860                 865                 870                 875

tac ctg ctt cca ctc aac gtg atc cag gta gag atg atg cga cgc tac      2750
Tyr Leu Leu Pro Leu Asn Val Ile Gln Val Glu Met Met Arg Arg Tyr
                880                 885                 890

cga aaa ggc gac caa agc gag caa gtg tcc cgc aac att cag ctg acc      2798
Arg Lys Gly Asp Gln Ser Glu Gln Val Ser Arg Asn Ile Gln Leu Thr
            895                 900                 905

atg aac ggt ctt tcc act gcg ctg cgc aac tcc ggc tag tccagccggc      2847
Met Asn Gly Leu Ser Thr Ala Leu Arg Asn Ser Gly
        910                 915

tgggtagtac tcgtgtatac tgt                                            2870


<210> SEQ ID NO 2
<211> LENGTH: 919
<212> TYPE: PRT
<213> ORGANISM: Corynebacterium glutamicum

<400> SEQUENCE: 2

Met Thr Asp Phe Leu Arg Asp Asp Ile Arg Phe Leu Gly Gln Ile Leu
1               5                   10                  15

Gly Glu Val Ile Ala Glu Gln Glu Gly Gln Glu Val Tyr Glu Leu Val
            20                  25                  30

Glu Gln Ala Arg Leu Thr Ser Phe Asp Ile Ala Lys Gly Asn Ala Glu
        35                  40                  45

Met Asp Ser Leu Val Gln Val Phe Asp Gly Ile Thr Pro Ala Lys Ala
    50                  55                  60

Thr Pro Ile Ala Arg Ala Phe Ser His Phe Ala Leu Leu Ala Asn Leu
65                  70                  75                  80
```

-continued

```
Ala Glu Asp Leu Tyr Asp Glu Glu Leu Arg Glu Gln Ala Leu Asp Ala
                85                  90                  95

Gly Asp Thr Pro Pro Asp Ser Thr Leu Asp Ala Thr Trp Leu Lys Leu
            100                 105                 110

Asn Glu Gly Asn Val Gly Ala Glu Ala Val Ala Asp Val Leu Arg Asn
        115                 120                 125

Ala Glu Val Ala Pro Val Leu Thr Ala His Pro Thr Glu Thr Arg Arg
    130                 135                 140

Arg Thr Val Phe Asp Ala Gln Lys Trp Ile Thr Thr His Met Arg Glu
145                 150                 155                 160

Arg His Ala Leu Gln Ser Ala Glu Pro Thr Ala Arg Thr Gln Ser Lys
                165                 170                 175

Leu Asp Glu Ile Glu Lys Asn Ile Arg Arg Arg Ile Thr Ile Leu Trp
            180                 185                 190

Gln Thr Ala Leu Ile Arg Val Ala Arg Pro Arg Ile Glu Asp Glu Ile
        195                 200                 205

Glu Val Gly Leu Arg Tyr Tyr Lys Leu Ser Leu Leu Glu Glu Ile Pro
    210                 215                 220

Arg Ile Asn Arg Asp Val Ala Val Glu Leu Arg Glu Arg Phe Gly Glu
225                 230                 235                 240

Gly Val Pro Leu Lys Pro Val Val Lys Pro Gly Ser Trp Ile Gly Gly
                245                 250                 255

Asp His Asp Gly Asn Pro Tyr Val Thr Ala Glu Thr Val Glu Tyr Ser
            260                 265                 270

Thr His Arg Ala Ala Glu Thr Val Leu Lys Tyr Tyr Ala Arg Gln Leu
        275                 280                 285

His Ser Leu Glu His Glu Leu Ser Leu Ser Asp Arg Met Asn Lys Val
    290                 295                 300

Thr Pro Gln Leu Leu Ala Leu Ala Asp Ala Gly His Asn Asp Val Pro
305                 310                 315                 320

Ser Arg Val Asp Glu Pro Tyr Arg Arg Ala Val His Gly Val Arg Gly
                325                 330                 335

Arg Ile Leu Ala Thr Thr Ala Glu Leu Ile Gly Glu Asp Ala Val Glu
            340                 345                 350

Gly Val Trp Phe Lys Val Phe Thr Pro Tyr Ala Ser Pro Glu Glu Phe
        355                 360                 365

Leu Asn Asp Ala Leu Thr Ile Asp His Ser Leu Arg Glu Ser Lys Asp
    370                 375                 380

Val Leu Ile Ala Asp Asp Arg Leu Ser Val Leu Ile Ser Ala Ile Glu
385                 390                 395                 400

Ser Phe Gly Phe Asn Leu Tyr Ala Leu Asp Leu Arg Gln Asn Ser Glu
                405                 410                 415

Ser Tyr Glu Asp Val Leu Thr Glu Leu Phe Glu Arg Ala Gln Val Thr
            420                 425                 430

Ala Asn Tyr Arg Glu Leu Ser Glu Ala Glu Lys Leu Glu Val Leu Leu
        435                 440                 445

Lys Glu Leu Arg Ser Pro Arg Pro Leu Ile Pro His Gly Ser Asp Glu
    450                 455                 460

Tyr Ser Glu Val Thr Asp Arg Glu Leu Gly Ile Phe Arg Thr Ala Ser
465                 470                 475                 480

Glu Ala Val Lys Lys Phe Gly Pro Arg Met Val Pro His Cys Ile Ile
                485                 490                 495
```

```
Ser Met Ala Ser Ser Val Thr Asp Val Leu Glu Pro Met Val Leu Leu
            500                 505                 510

Lys Glu Phe Gly Leu Ile Ala Ala Asn Gly Asp Asn Pro Arg Gly Thr
        515                 520                 525

Val Asp Val Ile Pro Leu Phe Glu Thr Ile Glu Asp Leu Gln Ala Gly
    530                 535                 540

Ala Gly Ile Leu Asp Glu Leu Trp Lys Ile Asp Leu Tyr Arg Asn Tyr
545                 550                 555                 560

Leu Leu Gln Arg Asp Asn Val Gln Glu Val Met Leu Gly Tyr Ser Asp
                565                 570                 575

Ser Asn Lys Asp Gly Gly Tyr Phe Ser Ala Asn Trp Ala Leu Tyr Asp
            580                 585                 590

Ala Glu Leu Gln Leu Val Glu Leu Cys Arg Ser Ala Gly Val Lys Leu
        595                 600                 605

Arg Leu Phe His Gly Arg Gly Gly Thr Val Gly Arg Gly Gly Gly Pro
    610                 615                 620

Ser Tyr Asp Ala Ile Leu Ala Gln Pro Arg Gly Ala Val Gln Gly Ser
625                 630                 635                 640

Val Arg Ile Thr Glu Gln Gly Glu Ile Ile Ser Ala Lys Tyr Gly Asn
                645                 650                 655

Pro Glu Thr Ala Arg Arg Asn Leu Glu Ala Leu Val Ser Ala Thr Leu
            660                 665                 670

Glu Ala Ser Leu Leu Asp Val Ser Glu Leu Thr Asp His Gln Arg Ala
        675                 680                 685

Tyr Asp Ile Met Ser Glu Ile Ser Glu Leu Ser Leu Lys Lys Tyr Ala
    690                 695                 700

Ser Leu Val His Glu Asp Gln Gly Phe Ile Asp Tyr Phe Thr Gln Ser
705                 710                 715                 720

Thr Pro Leu Gln Glu Ile Gly Ser Leu Asn Ile Gly Ser Arg Pro Ser
                725                 730                 735

Ser Arg Lys Gln Thr Ser Ser Val Glu Asp Leu Arg Ala Ile Pro Trp
            740                 745                 750

Val Leu Ser Trp Ser Gln Ser Arg Val Met Leu Pro Gly Trp Phe Gly
        755                 760                 765

Val Gly Thr Ala Leu Glu Gln Trp Ile Gly Glu Gly Glu Gln Ala Thr
    770                 775                 780

Gln Arg Ile Ala Glu Leu Gln Thr Leu Asn Glu Ser Trp Pro Phe Phe
785                 790                 795                 800

Thr Ser Val Leu Asp Asn Met Ala Gln Val Met Ser Lys Ala Glu Leu
                805                 810                 815

Arg Leu Ala Lys Leu Tyr Ala Asp Leu Ile Pro Asp Thr Glu Val Ala
            820                 825                 830

Glu Arg Val Tyr Ser Val Ile Arg Glu Glu Tyr Phe Leu Thr Lys Lys
        835                 840                 845

Met Phe Cys Val Ile Thr Gly Ser Asp Asp Leu Leu Asp Asp Asn Pro
    850                 855                 860

Leu Leu Ala Arg Ser Val Gln Arg Arg Tyr Pro Tyr Leu Leu Pro Leu
865                 870                 875                 880

Asn Val Ile Gln Val Glu Met Met Arg Arg Tyr Arg Lys Gly Asp Gln
                885                 890                 895

Ser Glu Gln Val Ser Arg Asn Ile Gln Leu Thr Met Asn Gly Leu Ser
            900                 905                 910

Thr Ala Leu Arg Asn Ser Gly
```

915

<210> SEQ ID NO 3
<211> LENGTH: 919
<212> TYPE: PRT
<213> ORGANISM: Corynebacterium efficiens YS-314

<400> SEQUENCE: 3

```
Met Asn Glu Leu Leu Arg Asp Asp Ile Arg Tyr Leu Gly Arg Ile Leu
1               5                   10                  15

Gly Glu Val Ile Ser Glu Gln Glu Gly His His Val Phe Glu Leu Val
            20                  25                  30

Glu Arg Ala Arg Arg Thr Ser Phe Asp Ile Ala Lys Gly Arg Ala Glu
        35                  40                  45

Met Asp Ser Leu Val Glu Val Phe Ala Gly Ile Asp Pro Glu Asp Ala
    50                  55                  60

Thr Pro Val Ala Arg Ala Phe Thr His Phe Ala Leu Leu Ala Asn Leu
65                  70                  75                  80

Ala Glu Asp Leu His Asp Ala Ala Gln Arg Glu Gln Ala Leu Asn Ser
                85                  90                  95

Gly Glu Pro Ala Pro Asp Ser Thr Leu Glu Ala Thr Trp Val Lys Leu
            100                 105                 110

Asp Asp Ala Gly Val Gly Ser Gly Glu Val Ala Ala Val Ile Arg Asn
        115                 120                 125

Ala Leu Val Ala Pro Val Leu Thr Ala His Pro Thr Glu Thr Arg Arg
    130                 135                 140

Arg Thr Val Phe Asp Ala Gln Lys His Ile Thr Ala Leu Met Glu Glu
145                 150                 155                 160

Arg His Leu Leu Leu Ala Leu Pro Thr His Ala Arg Thr Gln Ser Lys
                165                 170                 175

Leu Asp Asp Ile Glu Arg Asn Ile Arg Arg Arg Ile Thr Ile Leu Trp
            180                 185                 190

Gln Thr Ala Leu Ile Arg Val Ala Arg Pro Arg Ile Glu Asp Glu Val
        195                 200                 205

Glu Val Gly Leu Arg Tyr Tyr Lys Leu Ser Leu Leu Ala Glu Ile Pro
    210                 215                 220

Arg Ile Asn His Asp Val Thr Val Glu Leu Ala Arg Arg Phe Gly Gly
225                 230                 235                 240

Asp Ile Pro Thr Thr Ala Met Val Arg Pro Gly Ser Trp Ile Gly Gly
                245                 250                 255

Asp His Asp Gly Asn Pro Phe Val Thr Ala Glu Thr Val Thr Tyr Ala
            260                 265                 270

Thr His Arg Ala Ala Glu Thr Val Leu Lys Tyr Tyr Val Lys Gln Leu
        275                 280                 285

His Ala Leu Glu His Glu Leu Ser Leu Ser Asp Arg Met Asn Val Ile
    290                 295                 300

Ser Asp Glu Leu Arg Val Leu Ala Asp Ala Gly Gln Asn Asp Met Pro
305                 310                 315                 320

Ser Arg Val Asp Glu Pro Tyr Arg Arg Ala Ile His Gly Met Arg Gly
                325                 330                 335

Arg Met Leu Ala Thr Thr Ala Ala Leu Ile Gly Glu Glu Ala Val Glu
            340                 345                 350

Gly Thr Trp Phe Lys Thr Phe Thr Pro Tyr Thr Asp Thr His Glu Phe
        355                 360                 365
```

-continued

```
Lys Arg Asp Leu Asp Ile Val Asp Gly Ser Leu Arg Met Ser Arg Asp
    370                 375                 380

Asp Ile Ile Ala Asp Asp Arg Leu Ala Met Leu Arg Ser Ala Leu Asp
385                 390                 395                 400

Ser Phe Gly Phe Asn Leu Tyr Ser Leu Asp Leu Arg Gln Asn Ser Asp
                405                 410                 415

Gly Phe Glu Asp Val Leu Thr Glu Leu Phe Ala Thr Ala Gln Thr Glu
            420                 425                 430

Lys Asn Tyr Arg Gly Leu Thr Glu Ala Glu Lys Leu Asp Leu Leu Ile
        435                 440                 445

Arg Glu Leu Ser Thr Pro Arg Pro Leu Ile Pro His Gly Asp Pro Asp
    450                 455                 460

Tyr Ser Glu Ala Thr Asn Arg Glu Leu Gly Ile Phe Ser Lys Ala Ala
465                 470                 475                 480

Glu Ala Val Arg Lys Phe Gly Pro Leu Met Val Pro His Cys Ile Ile
                485                 490                 495

Ser Met Ala Ser Ser Val Thr Asp Ile Leu Glu Pro Met Val Leu Leu
            500                 505                 510

Lys Glu Phe Gly Leu Ile Arg Ala Asn Gly Lys Asn Pro Thr Gly Ser
        515                 520                 525

Val Asp Val Ile Pro Leu Phe Glu Thr Ile Asp Asp Leu Gln Arg Gly
    530                 535                 540

Ala Gly Ile Leu Glu Glu Leu Trp Asp Ile Asp Leu Tyr Arg Asn Tyr
545                 550                 555                 560

Leu Glu Gln Arg Asp Asn Val Gln Glu Val Met Leu Gly Tyr Ser Asp
                565                 570                 575

Ser Asn Lys Asp Gly Gly Tyr Phe Ala Ala Asn Trp Ala Leu Tyr Asp
            580                 585                 590

Ala Glu Leu Arg Leu Val Glu Leu Cys Arg Gly Arg Asn Val Lys Leu
        595                 600                 605

Arg Leu Phe His Gly Arg Gly Gly Thr Val Gly Arg Gly Gly Gly Pro
    610                 615                 620

Ser Tyr Asp Ala Ile Leu Ala Gln Pro Lys Gly Ala Val Arg Gly Ala
625                 630                 635                 640

Val Arg Val Thr Glu Gln Gly Glu Ile Ile Ser Ala Lys Tyr Gly Asn
                645                 650                 655

Pro Asp Thr Ala Arg Arg Asn Leu Glu Ala Leu Val Ser Ala Thr Leu
            660                 665                 670

Glu Ala Ser Leu Leu Asp Asp Val Glu Leu Pro Asn Arg Glu Arg Ala
        675                 680                 685

His Gln Ile Met Gly Glu Ile Ser Glu Leu Ser Phe Arg Arg Tyr Ser
    690                 695                 700

Ser Leu Val His Glu Asp Pro Gly Phe Ile Gln Tyr Phe Thr Gln Ser
705                 710                 715                 720

Thr Pro Leu Gln Glu Ile Gly Ser Leu Asn Ile Gly Ser Arg Pro Ser
                725                 730                 735

Ser Arg Lys Gln Thr Asn Thr Val Glu Asp Leu Arg Ala Ile Pro Trp
            740                 745                 750

Val Leu Ser Trp Ser Gln Ser Arg Val Met Leu Pro Gly Trp Phe Gly
        755                 760                 765

Val Gly Thr Ala Leu Arg Glu Trp Ile Gly Glu Gly Glu Gly Ala Ala
    770                 775                 780

Glu Arg Ile Ala Glu Leu Gln Glu Leu Asn Arg Cys Trp Pro Phe Phe
```

785 790 795 800

Thr Ser Val Leu Asp Asn Met Ala Gln Val Met Ser Lys Ala Glu Leu
805 810 815

Arg Leu Ala Arg Leu Tyr Ala Asp Leu Ile Pro Asp Arg Glu Val Ala
820 825 830

Asp Arg Ile Tyr Glu Thr Ile Phe Gly Glu Tyr Phe Leu Thr Lys Glu
835 840 845

Met Phe Cys Thr Ile Thr Gly Ser Gln Asp Leu Leu Asp Asp Asn Pro
850 855 860

Ala Leu Ala Arg Ser Val Arg Ser Arg Phe Pro Tyr Leu Leu Pro Leu
865 870 875 880

Asn Val Ile Gln Val Glu Met Met Arg Arg Tyr Arg Ser Gly Asp Glu
885 890 895

Gly Thr Ala Val Pro Arg Asn Ile Arg Leu Thr Met Asn Gly Leu Ser
900 905 910

Thr Ala Leu Arg Asn Ser Gly
915

<210> SEQ ID NO 4
<211> LENGTH: 919
<212> TYPE: PRT
<213> ORGANISM: Corynebacterium callunae DSM 20147

<400> SEQUENCE: 4

Met Asn Asp Leu Leu Arg Asp Asp Ile Arg Phe Leu Gly Arg Ile Leu
1 5 10 15

Gly Lys Val Ile Ser Glu Gln Glu Gly Ser Glu Val Tyr Glu Leu Val
20 25 30

Glu Arg Ala Arg Gln Thr Ser Phe Gln Ile Ala Lys Gly Asn Leu Glu
35 40 45

Met Asp Thr Leu Val Glu Val Phe Lys Gly Ile Asp Pro Glu Lys Ala
50 55 60

Thr Pro Val Ala Arg Ala Phe Thr His Phe Ala Leu Leu Ala Asn Leu
65 70 75 80

Ala Glu Asp Leu His Asp Ala Glu Ala Arg Glu Gln Ala Leu Asp Ser
85 90 95

Gly Glu Thr Pro Pro Glu Ser Thr Leu Glu Ser Thr Trp Leu Lys Leu
100 105 110

Asp Glu Ala Glu Val Lys Ala Ser Asp Val Ser Asp Val Leu Arg Asn
115 120 125

Ala Gln Val Ala Pro Val Leu Thr Ala His Pro Thr Glu Thr Arg Arg
130 135 140

Arg Thr Val Phe Asp Ala Gln Lys Trp Ile Thr Ala Tyr Met Gln Glu
145 150 155 160

Arg Gln Leu Leu Leu Ala Ala Pro Lys Asn Ala Arg Thr Gln Ala Lys
165 170 175

Leu Asp Ala Ile Glu Lys Asn Ile His Arg Arg Ile Ser Val Leu Trp
180 185 190

Gln Thr Ala Leu Ile Arg Val Ala Arg Pro Arg Ile Glu Asp Glu Ile
195 200 205

Glu Val Gly Leu Arg Tyr Tyr Lys Leu Ser Leu Leu Glu Glu Ile Pro
210 215 220

Arg Ile Asn Arg Asp Val Val Leu Glu Leu Arg Ser Arg Tyr Gly Lys
225 230 235 240

-continued

```
Val Ile Pro Ala Lys Ala Val Ile Lys Pro Gly Ser Trp Ile Gly Gly
                245                 250                 255

Asp His Asp Gly Asn Pro Tyr Val Thr Ala Asp Val Val Ala Tyr Ser
            260                 265                 270

Thr Ser Arg Ala Ala Glu Thr Val Leu Lys Tyr Tyr Gly Arg Gln Leu
        275                 280                 285

His Thr Leu Glu His Glu Leu Ser Leu Ser Asp Arg Met Ser Ser Val
    290                 295                 300

Thr Glu Glu Leu Arg Glu Leu Ala Asp Ala Gly Lys Asn Asp Val Pro
305                 310                 315                 320

Ser Arg Val Asp Glu Pro Tyr Arg Arg Ala Val His Gly Ile Arg Gly
                325                 330                 335

Arg Ile Leu Ala Thr Thr Ala His Leu Ile Gly Glu His Ala Val Glu
            340                 345                 350

Gly Thr Trp Phe Lys Ile Phe Glu Pro Tyr Ser Ser Pro Glu Glu Phe
        355                 360                 365

Ala Ala Glu Leu Lys Ile Val Asp Asp Ser Leu Arg Ala Ser His Asp
    370                 375                 380

Glu Leu Ile Ala Asp Asp Arg Leu Ala Ala Ile Tyr Ala Ala Val Gln
385                 390                 395                 400

Ser Phe Gly Phe Asn Leu Tyr Ser Leu Asp Leu Arg Gln Asn Ser Glu
                405                 410                 415

Ser Tyr Glu Asp Val Leu Thr Glu Leu Phe Gln Asn Ala Gln Val Thr
            420                 425                 430

Ala Asp Tyr Arg Asn Leu Asp Glu Ala Ala Lys Thr Glu Leu Leu Leu
        435                 440                 445

Lys Glu Leu Arg Ser Pro Arg Pro Leu Ile Pro Asn Gly Gly Trp Asp
    450                 455                 460

Phe Thr Glu Pro Thr Glu Arg Glu Leu Gly Ile Phe Lys Met Ala Ala
465                 470                 475                 480

His Ala Val Glu Lys Phe Gly Pro Asn Met Val Pro His Cys Ile Ile
                485                 490                 495

Ser Met Ala Ser Ser Val Thr Asp Val Leu Glu Pro Met Val Leu Leu
            500                 505                 510

Lys Glu Phe Gly Leu Ile Lys Ala Lys Gly Asp Thr Pro Val Gly Ser
        515                 520                 525

Ile Asp Val Ile Pro Leu Phe Glu Thr Ile Asp Asp Leu Gln Ala Gly
    530                 535                 540

Ala Gly Ile Leu Glu Asp Leu Trp Lys Ile Asp Leu Tyr Arg Asn Tyr
545                 550                 555                 560

Leu Gln Gln Arg Asp Asn Val Gln Glu Val Met Leu Gly Tyr Ser Asp
                565                 570                 575

Ser Asn Lys Asp Gly Gly Tyr Phe Ser Ala Asn Trp Ala Leu Tyr Asp
            580                 585                 590

Ala Glu Leu Gln Leu Val Asp Leu Cys Arg Ser Ala Gly Val Lys Leu
        595                 600                 605

Arg Leu Phe His Gly Arg Gly Gly Thr Val Gly Arg Gly Gly Gly Pro
    610                 615                 620

Ser Tyr Asp Ala Ile Leu Ala Gln Pro Lys Gly Ala Val Arg Gly Ser
625                 630                 635                 640

Leu Arg Ile Thr Glu Gln Gly Glu Ile Ile Ser Ala Lys Tyr Gly Ser
                645                 650                 655

Pro Glu Thr Ala Arg Arg Asn Leu Glu Ala Leu Val Ser Ala Thr Leu
```

660 665 670

Glu Ala Ser Leu Leu Asp Val Ser Asp Leu Ser Asp Pro Glu Arg Ala
675 680 685

Tyr Glu Ile Met Arg Glu Ile Ser Glu Leu Ser Leu Gln Lys Tyr Ser
690 695 700

Ser Leu Val His Glu Asp Pro Gly Phe Ile Asp Tyr Phe Thr Gln Ser
705 710 715 720

Thr Pro Leu Arg Glu Ile Gly Ser Leu Asn Ile Gly Ser Arg Pro Ser
725 730 735

Ser Arg Lys Gln Thr Ser Ser Val Glu Asp Leu Arg Ala Ile Pro Trp
740 745 750

Val Leu Ser Trp Ser Gln Ser Arg Val Met Leu Pro Gly Trp Phe Gly
755 760 765

Val Gly Thr Ala Leu Gln Gln Trp Ile Gly Ser Gly Glu Gln Ala Thr
770 775 780

Glu Arg Ile Lys Glu Leu Gln Glu Leu Asn Glu Thr Trp Pro Phe Phe
785 790 795 800

Thr Ser Val Leu Asp Asn Met Ala Gln Val Met Ser Lys Ala Glu Leu
805 810 815

Arg Leu Ala Lys Leu Tyr Ser Glu Leu Ile Pro Asp Arg Glu Val Ala
820 825 830

Gln Arg Ile Tyr Asp Val Ile Phe Asp Glu Tyr Phe Leu Thr Lys Glu
835 840 845

Met Phe Cys Val Ile Thr Gly Ser Thr Asp Leu Leu Asp Glu Asn Pro
850 855 860

Leu Leu Ala Arg Ser Val Arg Ser Arg Phe Pro Tyr Leu Leu Pro Leu
865 870 875 880

Asn Val Ile Gln Val Glu Met Met Arg Arg Tyr Arg Ala Gly Asp Glu
885 890 895

Ser Lys Gly Val Ser Arg Asn Ile Gln Leu Thr Met Asn Gly Leu Ala
900 905 910

Thr Ala Leu Arg Asn Ser Gly
915

<210> SEQ ID NO 5
<211> LENGTH: 920
<212> TYPE: PRT
<213> ORGANISM: Corynebacterium ammoniagenes DSM 20306

<400> SEQUENCE: 5

Met Ser Glu Gln Val Arg Asp Asp Ile Arg Leu Leu Gly Arg Ile Leu
1 5 10 15

Gly Gln Val Ile Ala Glu Gln Glu Gly Glu Asp Val Tyr Glu Leu Val
20 25 30

Glu Ser Thr Arg Arg Leu Ala Phe Gly Val Ala Arg Gly Glu Glu Asp
35 40 45

Ala Glu Ala Leu Leu Ser Ala Phe Arg Ala Val Asp Glu Asn Lys Ile
50 55 60

Asn Leu Val Ala Arg Ser Phe Ser His Phe Ala Leu Met Ala Asn Ile
65 70 75 80

Ala Glu Asp Leu Asp Asp Glu Ser Ala Leu Ala Ala Arg Glu Asp Glu
85 90 95

Gly Ala Pro Ala Pro Asp Ala Ser Leu Glu Ala Val Leu Ala Lys Leu
100 105 110

-continued

```
Gln Ala Ala Gly Asp Ile Ser Thr Ser Asp Ile Thr Arg Val Leu Asp
        115                 120                 125

Thr Ala Gln Val Ser Pro Val Phe Thr Ala His Pro Thr Glu Thr Arg
    130                 135                 140

Arg Arg Thr Val Phe Asp Val Gln Ala Arg Ile Ile Ala Leu Leu Arg
145                 150                 155                 160

Glu Arg His Gly Ile Leu Ala Gln Pro Glu Thr Thr Arg Arg Lys Ala
            165                 170                 175

Arg Leu Ala Glu Ile Glu Arg Glu Ala His Leu Arg Met Thr Ile Leu
            180                 185                 190

Trp Gln Thr Ala Leu Ile Arg Ile Ala Arg Pro Gln Ile Glu Asp Glu
        195                 200                 205

Ala Asn Val Gly Leu Arg Tyr Phe Lys Arg Ser Leu Leu Glu Gln Val
    210                 215                 220

Pro Ala Ile Asn Arg Asp Thr Ile Ala Gly Leu Arg Glu Ala Phe Gly
225                 230                 235                 240

Ser Ala Val Pro Asn Arg Gln Val Val Arg Thr Gly Ser Trp Ile Gly
                245                 250                 255

Gly Asp His Asp Gly Asn Pro Tyr Val Thr Gly Glu Thr Leu Arg Tyr
            260                 265                 270

Ala Thr Arg Gln Ala Ala Asp Thr Val Leu Glu Tyr Tyr Val Asp Glu
        275                 280                 285

Leu Ala Leu Leu Glu Lys Glu Leu Ser Leu Ser Asp Arg Tyr Ser Glu
    290                 295                 300

Ser Ser Ala Glu Leu Gln Glu Leu Ala Ala Arg Gly Asn Asn Asp Val
305                 310                 315                 320

Pro Ser Arg Val Asp Glu Pro Tyr Arg Arg Ala Ile His Gly Val His
                325                 330                 335

Gly Arg Met Val Ala Thr Arg Ala Ala Ile Ala Asn Thr Gln Ser Asp
            340                 345                 350

Thr Glu Gln Gly Glu Phe Ala Pro Tyr Ala Ser Pro Ser Glu Phe Ala
        355                 360                 365

Ala Asp Leu Ser Val Ile Asp Arg Ser Leu Arg Gln Phe Asn Asp Ala
    370                 375                 380

Ile Ile Ala Glu Asp Arg Leu Leu Arg Ile Arg Ser Ala Val Asp Thr
385                 390                 395                 400

Phe Gly Phe His Leu Asn Ala Leu Asp Leu Arg Gln Asn Ser Glu Ser
                405                 410                 415

Phe Glu Phe Val Leu Asp Glu Leu Phe Ala Ala Ala Gly Val Thr Ala
            420                 425                 430

Ala Gly Ala Gly Tyr Lys Asp Leu Asp Glu Asn Ala Lys Arg Glu Leu
        435                 440                 445

Leu Ile Ala Glu Leu Thr Ser Ala Arg Pro Leu Thr Phe Gly Trp Ser
    450                 455                 460

Lys Gly Phe Ser Glu Thr Thr Glu Arg Glu Leu Gly Ile Phe Arg Ala
465                 470                 475                 480

Ala Ala Glu Ala Ile Asn Asp Leu Gly Pro Glu Val Val Pro His Cys
                485                 490                 495

Ile Val Ser Met Thr Gly Thr Val Ser Asp Ile Leu Glu Pro Met Val
            500                 505                 510

Leu Leu Lys Glu Val Gly Ile Ile Ser Phe Asp Pro Ala Gln Gln Arg
        515                 520                 525

Leu Val Gly Ser Val Asp Ile Ala Pro Leu Phe Glu Thr Ile Glu Asp
```

```
    530                 535                 540

Leu Gln Ala Gly Ala Arg Ile Leu Glu Glu Leu Trp Glu Val Asp Leu
545                 550                 555                 560

Tyr Arg His Tyr Leu Arg Gly Arg Asn Asp Thr Gln Glu Val Val Leu
                565                 570                 575

Gly Tyr Ser Asp Ser Asn Lys Asp Gly Gly Tyr Leu Leu Ala Asn Trp
            580                 585                 590

Ala Leu Tyr Asp Ala Gln Ile Asp Ile Val Asp Ala Cys Glu Arg His
        595                 600                 605

Gly Val Ala Leu Arg Phe Ser His Gly Arg Gly Gly Val Val Gly Arg
    610                 615                 620

Gly Gly Gly Pro Thr Tyr Asp Ala Ile Leu Ala Gln Pro Glu Gly Ala
625                 630                 635                 640

Val Arg Gly Ser Val Arg Ile Thr Glu Gln Gly Glu Val Ile Ser Ala
                645                 650                 655

Arg Tyr Gly Thr Ala Thr Ser Ala Arg Arg His Leu Glu Ala Phe Val
            660                 665                 670

Ala Gly Thr Leu Glu Ala Ser Leu Leu Asp Thr Glu Arg Leu Lys Gln
        675                 680                 685

Pro Glu Arg Ala Tyr Asp Ile Met Arg Glu Val Ser Ser Leu Ala Gly
    690                 695                 700

Glu Lys Tyr Lys Gln Leu Val Arg Asp Asp Glu Gly Phe Ile Asp Tyr
705                 710                 715                 720

Phe Thr Gln Ser Thr Pro Leu His Glu Ile Gly Asp Leu Asn Leu Gly
                725                 730                 735

Ser Arg Pro Thr Ala Arg Lys Gln Thr Glu Ser Ile Ser Asp Leu Arg
            740                 745                 750

Ala Ile Pro Trp Val Leu Ser Trp Ser Gln Ser Arg Val Asn Leu Pro
        755                 760                 765

Gly Trp Phe Gly Val Gly Ser Gly Ile Thr Gln Trp Ala Gly Glu Asp
    770                 775                 780

Asp Gln Arg Trp Asp Asp Leu Arg Thr Leu Tyr Gln Ala Trp Pro Phe
785                 790                 795                 800

Phe Arg Ser Val Leu Asp Asn Met Ala Gln Val Met Gly Lys Ala Ser
                805                 810                 815

Met Asp Leu Ala Lys Ile Tyr Ser Thr Leu Val Asp Asp Ala Glu Thr
            820                 825                 830

Ser Lys Arg Val Phe Thr Thr Ile Val Asp Glu Tyr Glu Leu Thr Arg
        835                 840                 845

Glu Val Phe His Arg Ile Thr Gly His Glu Ser Leu Met Ala Gly Asn
    850                 855                 860

Glu Arg Leu Glu Arg Ser Val His Arg Arg Tyr Pro Tyr Leu Leu Pro
865                 870                 875                 880

Leu Asn Ala Ile Gln Ile Glu Leu Leu Arg Arg Tyr Arg Ala Gly Asp
                885                 890                 895

Asp Ser Phe Leu Val Ser Lys Thr Ile Gln Val Thr Met Asn Gly Leu
            900                 905                 910

Ala Thr Gly Leu Arg Thr Ser Gly
        915                 920


<210> SEQ ID NO 6
<211> LENGTH: 923
<212> TYPE: PRT
<213> ORGANISM: Corynebacterium marinum DSM 44953
```

-continued

<400> SEQUENCE: 6

```
Met Ala Asp Arg Asp His Leu Gln Glu Asp Ile Arg Tyr Leu Gly Arg
1               5                   10                  15

Ile Leu Gly Arg Val Ile Ala Glu Gln Glu Gly Glu Asp Val Phe Asp
            20                  25                  30

Leu Val Glu His Ala Arg Gln Gln Ala Phe Glu Val Ala Arg Glu Asn
        35                  40                  45

Ala Ser Leu Glu Val Leu Val Glu Leu Phe Arg Asn Ile Asp Pro Ala
    50                  55                  60

Arg Ala Thr Pro Val Ile Arg Ala Phe Ser His Phe Ala Leu Met Ala
65                  70                  75                  80

Asn Leu Ala Glu Asp Ile His Asp Asp Phe Asn Arg Glu Arg Ile Leu
                85                  90                  95

Asp Glu Gly Gly Val Pro Ala Ser Thr Leu Glu Ala Thr Trp Glu Lys
            100                 105                 110

Phe Glu Ala Ala Gly Val Ser Pro Ala Asp Val Glu Lys Val Val Ser
        115                 120                 125

Asp Ala Leu Val Ala Pro Val Phe Thr Ala His Pro Thr Glu Thr Arg
    130                 135                 140

Arg Arg Thr Val Phe Asp Ala Gln Lys Lys Ile Thr Gly Leu Met Leu
145                 150                 155                 160

Thr Arg His Gln Leu Gln Asp Ala Glu Thr Thr Ala Arg Thr Gln Glu
                165                 170                 175

Arg Leu Asp Asp Ile Glu Arg Ser Ile Arg Arg Arg Met Thr Ile Leu
            180                 185                 190

Trp Gln Thr Ala Leu Ile Arg Gln Ala Arg Pro Arg Ile Glu Asp Glu
        195                 200                 205

Ile Glu Val Gly Leu Arg Tyr Tyr His Leu Ser Leu Leu Arg Glu Ile
    210                 215                 220

Pro Ala Leu Asn Arg Ala Val His Asp Thr Leu Thr Ser Arg Phe Asp
225                 230                 235                 240

Val Arg Phe Arg Asp Gly Gly Gly Ser Ala Ile Val Arg Pro Gly Ser
                245                 250                 255

Trp Ile Gly Gly Asp His Asp Gly Asn Pro Phe Val Thr Ala Asp Thr
            260                 265                 270

Leu Asp Tyr Ala Ser Arg Arg Ala Ala Gln Thr Val Leu Lys His Tyr
        275                 280                 285

Ser Gly Glu Leu His Ala Leu Glu His Glu Leu Ser Leu Ser Asp Arg
    290                 295                 300

Met Thr Ser Val Ser Val Glu Leu Val Gly Leu Ala Ala Arg Gly Arg
305                 310                 315                 320

Asn Asp Val Pro Ser Arg Val Asp Glu Pro Tyr Arg Gln Ala Ile His
                325                 330                 335

Gly Ile Arg Gly Arg Ile Leu Ala Thr Thr Ala Ala Leu Ile Gly Glu
            340                 345                 350

Asp Ala Val Glu Gly Val Trp His Arg Glu His Gln Pro Tyr Ala Ser
        355                 360                 365

Ala Ala Glu Phe Asp Ala Asp Leu Arg Ile Val Asp Glu Ser Leu Arg
    370                 375                 380

Ser Ser Asn Asp Ala Ile Ile Ala Asp Asp Cys Leu Ala Ala Ile Arg
385                 390                 395                 400

Ala Ala Val Ala Ser Phe Gly Phe His Leu His Ser Ile Asp Leu Arg
```

-continued

```
            405                 410                 415

Gln Asn Ser Glu Ser Phe Glu Asn Val Leu Thr Glu Val Phe Ala Thr
        420                 425                 430

Ala His Val His Pro Gly Tyr Ser Ala Leu Gly Glu Glu Glu Lys Ile
    435                 440                 445

Glu Leu Leu Ile Gly Glu Leu Arg Thr Pro Arg Pro Leu Val Pro Arg
    450                 455                 460

Gly Tyr Arg Gly Phe Ser Glu Ala Thr Gln Arg Glu Leu Asp Leu Leu
465                 470                 475                 480

Asn Arg Ala Ala Asp Ser Val Ala His Phe Gly Ala Glu Met Ile Pro
                485                 490                 495

His Gln Ile Ile Ser Met Ala Gln Ser Val Ser Asp Ile Leu Glu Pro
            500                 505                 510

Met Val Leu Leu Lys Glu Val Gly Leu Ile Arg Ala Asn Gly Ala Gly
        515                 520                 525

Pro Thr Gly Ser Val Asp Ile Ile Pro Leu Phe Glu Thr Ile Asp Asp
    530                 535                 540

Leu Glu Ala Gly Ala Gly Ile Leu Arg Arg Leu Trp Gln Leu Pro Leu
545                 550                 555                 560

Tyr Gln His Tyr Leu Glu His Arg Gly Asn Val Gln Glu Val Met Leu
                565                 570                 575

Gly Tyr Ser Asp Ser Asn Lys Asp Gly Gly Tyr Phe Ala Ala Asn Trp
            580                 585                 590

Ala Leu Tyr Asp Ala Glu Thr Gln Leu Val Gln Ala Gly Arg Asp His
        595                 600                 605

Gly Val Arg Leu Arg Leu Phe His Gly Arg Gly Gly Thr Val Gly Arg
    610                 615                 620

Gly Gly Gly Pro Ser Tyr Glu Ala Ile Leu Ala Gln Pro Gln Gly Ala
625                 630                 635                 640

Val Asp Gly Ser Val Arg Ile Thr Glu Gln Gly Glu Ile Ile Ser Ala
                645                 650                 655

Lys Tyr Gly Ser Pro Arg Thr Ala Arg Arg Asn Leu Glu Ala Leu Val
            660                 665                 670

Ser Ala Thr Leu Glu Ala Ser Leu Leu Pro Val Asp Glu Leu Thr Asp
        675                 680                 685

Arg Asp Arg Ala Met Glu Ile Met Arg Glu Leu Ser Leu Ile Ser Arg
    690                 695                 700

Arg Lys Tyr Ser Gln Leu Val His Asp Asp Pro Gly Phe Ile Arg Tyr
705                 710                 715                 720

Phe Thr Gln Ser Thr Pro Leu Asp Glu Ile Gly Ser Leu Asn Ile Gly
                725                 730                 735

Ser Arg Pro Thr Ser Arg Lys Gln Thr Thr Ala Val Glu Asp Leu Arg
            740                 745                 750

Ala Ile Pro Trp Val Leu Ala Trp Ser Gln Ser Arg Val Leu Leu Pro
        755                 760                 765

Gly Trp Phe Gly Val Gly Thr Ala Leu Glu Glu Trp Ile Gly Gln Gly
    770                 775                 780

Pro Asp Arg Ala Asp Arg Val Ala Glu Leu Arg Ala Leu Tyr Glu Ser
785                 790                 795                 800

Trp Pro Phe Phe Ala Ser Val Met Ser Asn Met Ala Gln Val Met Ser
                805                 810                 815

Lys Ala Gly Met Glu Leu Ala Glu Leu Tyr Ala Arg Leu Val Asp Asp
            820                 825                 830
```

```
Arg Glu Ile Ala Asp Arg Ile Leu Gly Val Ile Ser Ala Glu Phe Asp
        835                 840                 845

Leu Thr Arg Gln Met Phe Gly Val Val Thr Gly Ser Glu Asp Leu Leu
    850                 855                 860

Ala Asp Asn Pro Ala Leu Ala Arg Ser Val Arg Arg Arg Phe Pro Tyr
865                 870                 875                 880

Leu Leu Pro Leu Asn Ile Ile Gln Leu Glu Met Leu Arg Arg His Arg
                885                 890                 895

Ala Gly Asp Asp Arg Glu Val Val Ser Arg Gly Ile Gln Leu Thr Met
            900                 905                 910

Asn Gly Leu Ala Thr Ala Leu Arg Asn Ser Gly
        915                 920


<210> SEQ ID NO 7
<211> LENGTH: 923
<212> TYPE: PRT
<213> ORGANISM: Corynebacterium humireducens NBRC 106098

<400> SEQUENCE: 7

Met Thr Val Arg Asp His Leu Gln Glu Asp Ile Arg Tyr Leu Gly Arg
1               5                   10                  15

Ile Leu Gly Gln Val Ile Ala Glu Gln Glu Gly Glu Asp Val Phe Asn
            20                  25                  30

Leu Val Glu His Ala Arg Gln Gln Ala Phe Glu Val Ala Lys Gly Asn
        35                  40                  45

Ala Ser Leu Glu Val Leu Val Asp Leu Phe Arg Asn Ile Glu Pro Glu
    50                  55                  60

Arg Ala Thr Pro Val Ile Arg Ala Phe Ser His Phe Ala Leu Met Ala
65                  70                  75                  80

Asn Leu Ala Glu Asp Ile His Asp Asp Phe His Arg Glu Arg Ile Leu
                85                  90                  95

Asp Glu Gly Gly Ala Pro Asp Ser Thr Leu Asn Ala Thr Trp Glu Lys
            100                 105                 110

Phe Arg Glu Ala Gly Val Ser Ala Ala Asp Ile Glu Arg Ser Leu Ser
        115                 120                 125

Ala Gly Leu Val Ala Pro Val Leu Thr Ala His Pro Thr Glu Thr Arg
    130                 135                 140

Arg Arg Thr Val Phe Asp Ala Gln Lys His Ile Thr Glu Leu Met Leu
145                 150                 155                 160

Gln Arg His Ala Val Gln Asp Ala Glu Pro Asn Ala Arg Thr Glu Asp
                165                 170                 175

Arg Leu Ala Glu Ile Glu Arg Asn Ile Arg Arg Arg Met Thr Ile Leu
            180                 185                 190

Trp Gln Thr Ala Leu Ile Arg Gln Ala Arg Pro Arg Ile Glu Asp Glu
        195                 200                 205

Ile Glu Val Gly Leu Arg Tyr Tyr Thr Leu Ser Leu Leu Arg Glu Ile
    210                 215                 220

Pro Ala Leu Asn Arg His Val Val Asp Thr Leu Thr Glu Arg Phe Gly
225                 230                 235                 240

Ala Asp Leu Arg Asn Ser Ala Gly Gln Ala Ile Val Arg Pro Gly Ser
                245                 250                 255

Trp Ile Gly Gly Asp His Asp Gly Asn Pro Phe Val Thr Ala Asp Thr
            260                 265                 270

Leu Asp Tyr Ala Ser Arg Arg Ala Ala Gln Thr Val Leu Lys Tyr Tyr
```

-continued

```
        275                 280                 285

Val Thr Gln Leu His Ala Leu Glu His Glu Leu Ser Leu Ser Asp Arg
    290                 295                 300

Met Thr Ser Val Thr Val Glu Leu Val Ala Leu Ala Gly Arg Gly Lys
305                 310                 315                 320

Asn Asp Val Pro Ser Arg Val Asp Glu Pro Tyr Arg Arg Ala Val His
                325                 330                 335

Gly Val Arg Gly Arg Ile Leu Ala Thr Thr Ala Ala Leu Ile Gly Glu
            340                 345                 350

Asp Ala Val Glu Gly Val Trp His Arg Glu His Glu Pro Tyr Gly Ser
        355                 360                 365

Pro Gln Glu Phe Glu Ala Asp Leu Arg Val Ile Asp Thr Ser Leu Arg
    370                 375                 380

Ala Ser His Asp Glu Ile Ile Ala Asp Asp Arg Leu Ser Ser Ile Arg
385                 390                 395                 400

Ala Ala Val Ala Ser Phe Gly Phe His Leu Tyr Ser Ile Asp Leu Arg
                405                 410                 415

Gln Asn Ser Glu Ser Phe Glu Asn Val Leu Thr Glu Val Phe Ala Thr
            420                 425                 430

Ala His Val His Pro Asn Tyr Asp Thr Leu Arg Glu Glu Val Lys Ile
        435                 440                 445

Glu Leu Leu Thr Arg Glu Leu Gln Thr Pro Arg Pro Leu Val Pro Arg
    450                 455                 460

Gly Tyr Arg Gly Phe Ser Glu Pro Thr Gln Arg Glu Leu Asp Leu Ile
465                 470                 475                 480

Ser Gln Ala Ala Asp Ser Val Ala Arg Phe Gly Glu Gln Met Ile Pro
                485                 490                 495

His Gln Ile Ile Ser Met Ala Gln Ser Val Ser Asp Ile Leu Glu Pro
            500                 505                 510

Met Val Leu Leu Lys Glu Val Gly Leu Ile Gln Ala Asn Gly Gln Gly
        515                 520                 525

Pro Thr Gly Ser Val Asp Ile Ile Pro Leu Phe Glu Thr Ile Asp Asp
    530                 535                 540

Leu Gln Ala Gly Ala Gly Ile Leu Arg Glu Leu Trp Asp Leu Pro Ile
545                 550                 555                 560

Tyr Arg Ala Tyr Leu Ala Gln Arg Gly Asp Ile Gln Glu Val Met Leu
                565                 570                 575

Gly Tyr Ser Asp Ser Asn Lys Asp Gly Gly Tyr Phe Ala Ala Asn Trp
            580                 585                 590

Ala Leu Tyr Asp Ala Glu Thr Asp Leu Val Lys Val Gly Arg Glu Tyr
        595                 600                 605

Gly Val Arg Leu Arg Leu Phe His Gly Arg Gly Gly Thr Val Gly Arg
    610                 615                 620

Gly Gly Gly Pro Ser Tyr Asp Ala Leu Leu Ala Gln Pro Gln Gly Ala
625                 630                 635                 640

Val Asp Gly Ser Val Arg Ile Thr Glu Gln Gly Glu Ile Ile Ser Ala
                645                 650                 655

Lys Tyr Gly Ser Pro Arg Thr Ala Arg Arg Asn Leu Glu Ala Leu Val
            660                 665                 670

Ser Ala Thr Leu Glu Ala Ser Leu Leu Thr Val Asp Asp Leu Ala Asp
        675                 680                 685

Arg Ala Arg Ala Thr Gln Ile Met Ser Glu Leu Ala Gln Ile Ser Arg
    690                 695                 700
```

Arg Lys Tyr Ser Glu Leu Val His Glu Asp Pro Gly Phe Ile Pro Tyr
705 710 715 720

Phe Thr Gln Ser Thr Pro Leu Asp Glu Ile Gly Ser Leu Asn Ile Gly
725 730 735

Ser Arg Pro Thr Ala Arg Lys Gln Thr Lys Gly Val Asp Asp Leu Arg
740 745 750

Ala Ile Pro Trp Val Leu Ala Trp Ser Gln Ser Arg Val Leu Leu Pro
755 760 765

Gly Trp Phe Gly Val Gly Thr Ala Leu Ala Glu Trp Ile Gly Glu Gly
770 775 780

Glu Asp Arg Asp Glu Arg Ile Ala Glu Leu Arg Glu Leu Tyr Glu Ser
785 790 795 800

Trp Pro Phe Phe Thr Ser Ile Met Ser Asn Met Ala Gln Val Met Ser
805 810 815

Lys Ala Gly Met Asp Leu Ala Glu Leu Tyr Ala Arg Leu Ile Asp Asp
820 825 830

Arg Glu Val Ala Glu Arg Val His Gly Val Ile Thr Glu Glu Phe Glu
835 840 845

Leu Thr Arg Glu Met Phe Ser Thr Val Thr Gly Ser Ala Glu Leu Leu
850 855 860

Ala Asp Asn Pro Ala Leu Ala Arg Ser Val Arg Arg Arg Phe Pro Tyr
865 870 875 880

Leu Leu Pro Leu Asn Ile Ile Gln Leu Glu Leu Leu Arg Arg His Arg
885 890 895

Ala Gly Asp Ser Arg Arg Ala Val Ser Arg Gly Ile Gln Leu Thr Met
900 905 910

Asn Gly Leu Ala Thr Ala Leu Arg Asn Ser Gly
915 920

<210> SEQ ID NO 8
<211> LENGTH: 921
<212> TYPE: PRT
<213> ORGANISM: Corynebacterium halotolerans YIM 70093

<400> SEQUENCE: 8

Met Thr Pro Ala Asp His Leu Gln Glu Asp Ile Arg Tyr Leu Gly Arg
1 5 10 15

Val Leu Gly Arg Val Ile Ala Glu Gln Glu Gly Glu Glu Val Phe Asp
20 25 30

Leu Val Glu His Ala Arg Gln Leu Ala Phe Gly Ile Ala Lys Gly Asp
35 40 45

Thr Gly Leu Glu Ala Leu Val Glu Leu Phe Arg Asn Ile Glu Pro Ala
50 55 60

Arg Ala Thr Pro Val Ile Arg Ala Phe Ser His Phe Ala Leu Met Ala
65 70 75 80

Asn Leu Ala Glu Asp Leu His Asp Asp Phe Thr Arg Glu Arg Leu Leu
85 90 95

Asp Ala Gly Gly Pro Ala Pro Asp Ser Thr Leu Glu Thr Thr Trp Ala
100 105 110

Lys Leu Ala Gly Ala Gly Val Asp Ala Ala Thr Val Ala Glu Ala Leu
115 120 125

Asp Gly Ala Leu Val Ala Pro Val Leu Thr Ala His Pro Thr Glu Thr
130 135 140

Arg Arg Arg Thr Val Phe Asp Ala Gln Arg His Ile Thr Glu Gln Met

-continued

```
145                 150                 155                 160

Thr Val Arg His Arg Leu Leu Glu Ala Pro His Thr Ala Arg Thr Asp
                165                 170                 175

Ser Gln Leu Glu Glu Val Asp Arg Gln Ile Arg Arg Arg Leu Thr Ile
            180                 185                 190

Leu Trp Gln Thr Ala Leu Ile Arg Met Ala Arg Pro Arg Ile Glu Asp
        195                 200                 205

Glu Ile Glu Val Gly Leu Arg Tyr Tyr Lys Leu Ser Leu Leu Glu Glu
    210                 215                 220

Ile Pro Ala Leu Asn Arg Ala Val Asp Asp Arg Leu Arg Ala Asp Phe
225                 230                 235                 240

Gly Gln Gly Val Pro Thr Arg Ala Leu Val Arg Pro Gly Ser Trp Ile
                245                 250                 255

Gly Gly Asp His Asp Gly Asn Pro Phe Val Thr Ala Ala Thr Leu Asp
            260                 265                 270

Tyr Ala Thr Arg Arg Ala Ala Gln Thr Val Leu Lys His Tyr Glu Thr
        275                 280                 285

Gln Leu Leu Ala Leu Glu His Glu Leu Ser Leu Ser Asp Arg Met Thr
    290                 295                 300

Ser Val Thr Val Asp Leu Val Ala Leu Ala Lys Arg Gly Leu Asn Asp
305                 310                 315                 320

Val Pro Ser Arg Val Asp Glu Pro Tyr Arg Arg Ala Ile Arg Gly Ile
                325                 330                 335

Arg Gly Arg Leu Leu Ala Thr Thr Ala Thr Leu Ile Gly Glu Asp Ala
            340                 345                 350

Val Glu Gly Ser Trp His Arg Val His Glu Pro Tyr Ser Gly Pro Gly
        355                 360                 365

Glu Phe Asp Ala Asp Leu Ala Val Ile Asp Glu Ser Leu Arg Arg Ser
    370                 375                 380

His Asp Glu Ile Ile Ala Asp Asp Arg Leu Ala Thr Ile Arg Ala Ala
385                 390                 395                 400

Val Ala Gly Phe Gly Phe His Leu Tyr Ser Leu Asp Leu Arg Gln Asn
                405                 410                 415

Ser Glu Ser Phe Glu Ala Ile Leu Ala Glu Val Phe Ala Ala Ala Gly
            420                 425                 430

Val His Asp Asp Tyr Ala Ser Leu Gly Glu Glu Glu Arg Ile Asp Leu
        435                 440                 445

Leu Thr Arg Glu Leu Arg Thr Pro Arg Pro Leu Val Pro Arg Gly Arg
    450                 455                 460

Arg Gly Phe Ser Glu Pro Thr Gln Arg Glu Leu Asp Leu Phe Glu Gln
465                 470                 475                 480

Ala Ala Thr Ser Val Glu Arg Phe Gly Met Glu Met Ile Pro His Leu
                485                 490                 495

Ile Ile Ser Met Ala Thr Ser Val Ser Asp Ile Leu Glu Pro Met Val
            500                 505                 510

Leu Leu Lys Glu Val Gly Leu Leu His Ala Asp Gly Glu Arg Pro Thr
        515                 520                 525

Gly Ser Val Asp Val Ile Pro Leu Phe Glu Thr Ile Asp Asp Leu Ala
    530                 535                 540

Ala Gly Ala Gly Ile Leu Arg Glu Leu Trp Ala Leu Pro Leu Tyr Arg
545                 550                 555                 560

Ala Tyr Leu Ala Gln Arg Gly Asp Val Gln Glu Val Met Leu Gly Tyr
                565                 570                 575
```

```
Ser Asp Ser Asn Lys Asp Gly Gly Tyr Leu Ala Ala Asn Trp Ala Leu
            580                 585                 590

Tyr Asp Ala Glu Thr Gln Ile Val Ala Ala Gly Arg Asp His Gly Val
        595                 600                 605

Arg Leu Arg Leu Phe His Gly Arg Gly Gly Thr Val Gly Arg Gly Gly
    610                 615                 620

Gly Pro Ser Tyr Glu Ala Ile Leu Ala Gln Pro Lys Gly Ala Val Asp
625                 630                 635                 640

Gly Ser Val Arg Ile Thr Glu Gln Gly Glu Ile Ile Ser Ala Lys Tyr
                645                 650                 655

Gly Ser Gly His Thr Ala Arg Arg Asn Leu Glu Ala Leu Val Ser Ala
            660                 665                 670

Thr Leu Glu Ala Ser Leu Leu Asp Val Asp Glu Leu Val Asp Arg Glu
        675                 680                 685

Arg Ala Thr Gly Ile Met Thr Glu Ile Ala Arg Leu Ser Arg Ala Arg
    690                 695                 700

Tyr Ser Arg Leu Val His Glu Asp Pro Gly Phe Ile Pro Tyr Phe Thr
705                 710                 715                 720

Gln Ser Thr Pro Leu Asp Glu Ile Gly Ala Leu Asn Ile Gly Ser Arg
                725                 730                 735

Pro Thr Ser Arg Lys Gln Thr Asn Ser Val Ala Asp Leu Arg Ala Ile
            740                 745                 750

Pro Trp Val Leu Ala Trp Ser Gln Ser Arg Val Met Leu Pro Gly Trp
        755                 760                 765

Phe Gly Val Gly Thr Ala Leu Ala Glu Trp Ile Gly Glu Gly Asp Asp
    770                 775                 780

Ala Glu Asp Arg Cys Ala Glu Leu Arg His Leu Tyr Glu Thr Trp Pro
785                 790                 795                 800

Phe Phe Thr Ser Val Met Ser Asn Met Ala Gln Val Met Ser Lys Ala
                805                 810                 815

Gly Met Glu Leu Ala Gly Leu Tyr Ala Gly Leu Val Asp Asp Arg Glu
            820                 825                 830

Val Ala Gly Arg Ile Arg Gly Ile Ile Ser Glu Glu Phe Arg Leu Thr
        835                 840                 845

Arg Glu Met Phe Thr Lys Val Thr Gly Ser Glu Asp Leu Leu Ala Asp
    850                 855                 860

Asn Pro Met Leu Ala Arg Ser Val Arg Arg Arg Phe Pro Tyr Leu Leu
865                 870                 875                 880

Pro Leu Asn Ile Ile Gln Val Glu Leu Leu Arg Arg His Arg Ala Gly
                885                 890                 895

Asp Glu Arg Asp Ala Val Ser Arg Gly Ile Arg Leu Thr Met Asn Gly
            900                 905                 910

Leu Ala Thr Ala Leu Arg Asn Ser Gly
        915                 920


<210> SEQ ID NO 9
<211> LENGTH: 927
<212> TYPE: PRT
<213> ORGANISM: Corynebacterium deserti GIMN1.010

<400> SEQUENCE: 9

Met Glu Lys Ser Val Tyr Lys Val Met Thr Asp Phe Leu Arg Asp Asp
1               5                   10                  15

Ile Arg Phe Leu Gly Arg Ile Leu Gly Glu Val Ile Ala Glu Gln Glu
```

-continued

```
            20                  25                  30

Gly Arg Glu Val Tyr Glu Leu Val Glu Lys Ala Arg Gln Ile Ser Phe
        35                  40                  45

Glu Ile Ala Lys Gly Asn Ala Asp Met Asp Ser Leu Val Thr Val Phe
    50                  55                  60

Asp Gly Ile Ser Pro Ala Glu Ala Thr Pro Ile Ala Arg Ala Phe Thr
65                  70                  75                  80

His Phe Ala Leu Leu Ala Asn Leu Ala Glu Asp Leu His Asp Glu Gln
                85                  90                  95

Thr Arg Glu Lys Ala Leu Asp Ala Gly Glu Thr Pro Pro Asp Ser Thr
            100                 105                 110

Leu Asp Ala Thr Trp Leu Lys Leu Asn Asp Ala Asn Thr Asp Ala Gln
        115                 120                 125

Ala Val Thr Glu Phe Met Asn Asn Ala Gln Val Ala Pro Val Leu Thr
    130                 135                 140

Ala His Pro Thr Glu Thr Arg Arg Arg Thr Val Phe Asp Ala Gln Lys
145                 150                 155                 160

Trp Ile Thr Thr His Met Arg Glu Arg His Leu Ile Gln Thr Ser Thr
                165                 170                 175

Glu Thr Ala Arg Thr Gln Ala Lys Leu Asp Glu Ile Glu Arg Ser Ile
            180                 185                 190

Arg Arg Arg Ile Thr Ile Leu Trp Gln Thr Ala Leu Ile Arg Val Ala
        195                 200                 205

Arg Pro Arg Ile Glu Asp Glu Ile Glu Val Gly Leu Arg Tyr Tyr Lys
    210                 215                 220

Leu Ser Leu Leu Glu Glu Ile Pro Lys Ile Asn Arg Asp Val Asn Leu
225                 230                 235                 240

Glu Leu Arg Gln Arg Phe Gly Glu Asp Ile Pro Asn Lys Ala Val Ile
                245                 250                 255

Lys Pro Gly Ser Trp Ile Gly Gly Asp His Asp Gly Asn Pro Tyr Val
            260                 265                 270

Thr Ala Asp Thr Val Glu Tyr Ser Thr His Arg Ala Ala Gln Thr Val
        275                 280                 285

Leu Lys Tyr Tyr Thr Arg Gln Leu His Ser Leu Glu His Glu Leu Ser
    290                 295                 300

Leu Ser Asp Arg Met Asn Ala Val Thr Gln Glu Leu Ser Lys Leu Ala
305                 310                 315                 320

Asp Ala Gly Asn Asn Asp Val Pro Ser Arg Val Asp Glu Pro Tyr Arg
                325                 330                 335

Arg Ala Val His Gly Val Arg Gly Arg Ile Leu Ala Thr Thr Ala His
            340                 345                 350

Leu Ile Gly Glu Asp Ala Val Glu Gly Val Trp Phe Arg Gln Phe Glu
        355                 360                 365

Pro Tyr Thr Ser Pro Glu Glu Phe Leu Ala Asp Leu Val Thr Val Asp
    370                 375                 380

Gln Ser Leu Arg Ala Ser Asn Asp Asp Leu Ile Ala Asp Asp Arg Leu
385                 390                 395                 400

Ala Lys Leu Ile Ser Ala Val Glu Ser Phe Gly Phe Asn Leu Tyr Ser
                405                 410                 415

Leu Asp Leu Arg Gln Asn Ser Glu Ser Tyr Glu Asp Val Leu Thr Glu
            420                 425                 430

Leu Phe Gln Arg Ala Val Val Thr Asp Asn Tyr Arg Asp Met Ser Glu
        435                 440                 445
```

-continued

```
Glu Glu Lys Leu Glu Leu Leu Leu Ala Glu Leu Arg Ser Pro Arg Pro
    450                 455                 460

Leu Ile Pro His Gly Ala Glu Gly Tyr Ser Glu Pro Thr Asp Arg Glu
465                 470                 475                 480

Leu Gly Ile Phe Arg Lys Ala Ser Glu Ala Val Gln Lys Phe Gly Pro
                485                 490                 495

Arg Met Val Pro His Cys Ile Ile Ser Met Ala Ser Ser Val Thr Asp
            500                 505                 510

Val Leu Glu Pro Met Val Leu Leu Lys Glu Phe Gly Leu Ile Ala Ala
        515                 520                 525

Asn Gly Asp Ser Pro Thr Gly Thr Val Asp Val Ile Pro Leu Phe Glu
    530                 535                 540

Thr Ile Glu Asp Leu Gln Ala Gly Ser Gly Ile Leu Glu Glu Leu Trp
545                 550                 555                 560

Gly Ile Asp Leu Tyr Arg Asn Tyr Leu Glu Gln Arg Gly Met Thr Gln
                565                 570                 575

Glu Val Met Leu Gly Tyr Ser Asp Ser Asn Lys Asp Gly Gly Tyr Phe
            580                 585                 590

Ala Ala Asn Trp Ala Leu Tyr Asp Ala Glu Leu His Leu Val Glu Leu
        595                 600                 605

Cys Arg Ala Ala Gly Val Lys Leu Arg Leu Phe His Gly Arg Gly Gly
    610                 615                 620

Thr Val Gly Arg Gly Gly Gly Pro Ser Tyr Asp Ala Ile Leu Ala Gln
625                 630                 635                 640

Pro Lys Gly Ala Val Leu Gly Ser Val Arg Ile Thr Glu Gln Gly Glu
                645                 650                 655

Ile Ile Ser Ala Lys Tyr Gly Asn Pro Glu Thr Ala Arg Arg Asn Leu
            660                 665                 670

Glu Ala Leu Val Ser Ala Thr Leu Glu Ala Thr Leu Leu Asp Val Ser
        675                 680                 685

Asp Leu Ala Asp Pro Glu Arg Ala Tyr Thr Ile Met Arg Glu Ile Ser
    690                 695                 700

Glu Leu Ser Leu Lys Lys Tyr Ser Ser Leu Val His Glu Asp Pro Gly
705                 710                 715                 720

Phe Ile Ser Tyr Phe Thr Gln Ser Thr Pro Leu Arg Glu Ile Gly Ser
                725                 730                 735

Leu Asn Ile Gly Ser Arg Pro Ser Ser Arg Lys Gln Thr Ser Ser Val
            740                 745                 750

Asp Asp Leu Arg Ala Ile Pro Trp Val Leu Ser Trp Ser Gln Ser Arg
        755                 760                 765

Val Met Leu Pro Gly Trp Phe Gly Val Gly Ser Ala Leu Glu Glu Trp
    770                 775                 780

Ile Gly Ser Gly Glu Glu Ala Glu Ala Arg Ile Ala Glu Leu Gln Thr
785                 790                 795                 800

Leu Asn Glu Ser Trp Pro Phe Phe Thr Ser Val Leu Asp Asn Met Ala
                805                 810                 815

Gln Val Met Ser Lys Ala Glu Leu Arg Leu Ala Lys Leu Tyr Ala Asp
            820                 825                 830

Leu Ile Pro Asp Gln Glu Val Ala Glu Arg Ile Tyr Thr Asp Ile Phe
        835                 840                 845

Glu Glu Tyr Phe Leu Thr Lys Lys Met Phe Cys Lys Ile Thr Gly Ser
    850                 855                 860
```

Ser Asp Leu Leu Asp Asp Asn Pro Leu Leu Ala Arg Ser Val Gln Arg
865 870 875 880

Arg Tyr Pro Tyr Leu Leu Pro Leu Asn Val Ile Gln Val Glu Met Met
885 890 895

Arg Arg Phe Arg Ser Gly Asp Asp Ser Asp Gly Ile Ser Arg Asn Ile
900 905 910

Gln Leu Thr Met Asn Gly Leu Ser Thr Ala Leu Arg Asn Ser Gly
915 920 925

<210> SEQ ID NO 10
<211> LENGTH: 914
<212> TYPE: PRT
<213> ORGANISM: Corynebacterium doosanense CAU 212

<400> SEQUENCE: 10

Met Thr Glu Gln Val Arg Asp Asp Ile Arg Phe Leu Gly Arg Ile Leu
1 5 10 15

Gly Arg Val Ile Ala Glu Gln Glu Gly Glu Asp Val Phe Glu Leu Val
20 25 30

Glu Ser Thr Arg Gln Leu Ala Phe Gly Val Ala Arg Gly Asp Glu Asp
35 40 45

Ala Glu Ala Leu Leu Ala Thr Phe Arg Gly Val Asp Glu Asn Lys Ile
50 55 60

Asn Leu Val Ala Arg Ser Phe Ser His Phe Ser Leu Met Ala Asn Ile
65 70 75 80

Ala Glu Asp Leu Asp Asp Glu Ala Ala Leu Ala Ala Leu Glu Asp Glu
85 90 95

Gly Ser Gln Ala Pro Asp Ala Ser Leu Gln Gly Ala Leu Ala Lys Leu
100 105 110

Arg Ala Asp Gly Thr Val Ser Pro Gly Asp Val Ala Thr Met Leu Asp
115 120 125

Asn Ala Gln Val Ser Pro Val Phe Thr Ala His Pro Thr Glu Thr Arg
130 135 140

Arg Arg Thr Val Phe Asp Val Gln Ser Arg Ile Val Ala Leu Leu Arg
145 150 155 160

Glu Arg Arg Gly Ile Leu Ala Gln Pro Arg Thr Pro Arg Arg Asp Ala
165 170 175

Arg Leu Thr Gln Ile Glu Arg Glu Ala His Leu Arg Met Thr Leu Leu
180 185 190

Trp Gln Thr Ala Leu Ile Arg Ile Ala Arg Pro Arg Ile Glu Asp Glu
195 200 205

Val Asn Val Gly Leu Arg Tyr Phe Arg Leu Ser Leu Leu Asp Glu Val
210 215 220

Pro Ala Ile Asn Arg Asp Thr Ile Ala Gly Leu Arg Glu Leu Phe Gly
225 230 235 240

Ala Gly Val Pro Asp Arg Pro Leu Val Arg Thr Gly Ser Trp Ile Gly
245 250 255

Gly Asp His Asp Gly Asn Pro Phe Val Thr Gly Glu Thr Leu Thr Tyr
260 265 270

Ala Thr Gln Ala Ala Ala Asp Thr Val Leu Asp Tyr Tyr Asp Glu Gln
275 280 285

Leu Gly Glu Leu Glu Lys Glu Leu Ser Leu Ser Asp Arg Tyr Ser Glu
290 295 300

Cys Ser Gln Glu Leu Arg Glu Leu Ala Asp Arg Gly Asn Asn Asp Val
305 310 315 320

```
Pro Ser Arg Val Asp Glu Pro Tyr Arg Arg Ala Leu His Gly Val Leu
                325                 330                 335

Gly Arg Ile Arg Ala Thr Arg Cys Ala Leu Ala Asp Ala Pro Asp Ser
            340                 345                 350

Asp Gly Phe Asp Pro Tyr Pro Thr Pro Gln Asp Phe Ser Ala Asp Leu
        355                 360                 365

Asp Ile Ile Asp Arg Ser Leu Arg Gln Phe Asp Asp Ala Ile Ile Ala
    370                 375                 380

Asp Asp Arg Leu Leu Arg Ile Arg Ser Ala Ala Glu Thr Phe Gly Phe
385                 390                 395                 400

His Leu Asn Ser Leu Asp Leu Arg Gln Asn Ser Glu Ser Phe Glu Ala
                405                 410                 415

Val Leu Gly Glu Leu Phe Ala Ala Ala Gly Val Thr Ala Asp Tyr Ala
            420                 425                 430

Gly Leu Asp Glu Ala Ala Lys Cys Glu Leu Leu Val Ala Glu Leu Thr
        435                 440                 445

Ser Ala Arg Pro Leu Thr Phe Pro Trp Ala Glu Pro Phe Ser Glu Pro
    450                 455                 460

Thr Glu Arg Glu Leu Gly Ile Phe Arg Ala Ala Ala Gly Ala Val Asp
465                 470                 475                 480

Lys Leu Gly Pro Glu Val Ile Pro His Cys Ile Val Ser Met Thr Gly
                485                 490                 495

Thr Val Ser Asp Ile Leu Glu Pro Met Ile Leu Leu Lys Glu Phe Gly
            500                 505                 510

Leu Ile Ser Phe Asp Pro Glu Arg Gly Gln Leu Val Gly Gln Val Asp
        515                 520                 525

Ile Ala Pro Leu Phe Glu Thr Ile Asp Asp Leu Lys Ala Gly Ala Arg
    530                 535                 540

Ile Leu Glu Glu Leu Trp Asp Val Pro Val Tyr Arg Gln Tyr Leu Arg
545                 550                 555                 560

Gln Arg Asp Asp Leu Gln Glu Val Val Leu Gly Tyr Ser Asp Ser Asn
                565                 570                 575

Lys Asp Gly Gly Tyr Leu Ser Ala Asn Trp Glu Leu Tyr Asp Ala Gln
            580                 585                 590

Ile Ala Ile Val Glu Ala Cys Arg Asn His Asp Ile Arg Leu Arg Phe
        595                 600                 605

Ser His Gly Arg Gly Gly Ala Val Gly Arg Gly Gly Gly Pro Thr Tyr
    610                 615                 620

Asp Ala Ile Leu Ala Gln Pro Val Gly Ala Val Arg Gly Ser Val Arg
625                 630                 635                 640

Ile Thr Glu Gln Gly Glu Val Ile Ser Ala His Tyr Gly Thr Ala Thr
                645                 650                 655

Thr Ala Arg Arg His Leu Glu Ala Phe Val Ala Gly Thr Leu Glu Ala
            660                 665                 670

Ser Leu Leu Asp Thr Glu Ser Leu Asp Asn Pro Thr Arg Ala Tyr Glu
        675                 680                 685

Ile Met Arg Glu Ile Ala Glu Leu Ala Gly Gly Lys Tyr Gly Asp Leu
    690                 695                 700

Ile Arg Arg Asp Pro Gly Phe Ile Asp Tyr Phe Thr Gln Ser Thr Pro
705                 710                 715                 720

Leu His Glu Ile Gly Asp Leu Asn Leu Gly Ser Arg Pro Thr Ala Arg
                725                 730                 735
```

-continued

Lys Gln Thr Ser Ser Val Ser Asp Leu Arg Ala Ile Pro Trp Val Leu
740 745 750

Ser Trp Ala Gln Ser Arg Val Asn Leu Pro Gly Trp Phe Gly Val Gly
755 760 765

Thr Ala Ile Thr Cys Trp Ala Gly Asp Asp Glu Thr Arg Trp Glu Glu
770 775 780

Leu Arg Thr Leu Tyr Arg Thr Trp Ser Phe Phe Arg Ser Val Met Asp
785 790 795 800

Asn Met Ala Gln Val Met Gly Lys Ala Ser Met Asp Leu Ala Arg Ile
805 810 815

Tyr Ser Thr Leu Val Asp Asp Pro Glu Val Ser Glu Arg Val Phe Ser
820 825 830

Thr Ile Ala Asp Glu Phe Glu Leu Thr Gln Ser Val Phe His Arg Ile
835 840 845

Thr Gly His Glu Ser Leu Met Ala Gly Asn Asp Arg Leu Glu Arg Ser
850 855 860

Val Gln Arg Arg Tyr Pro Tyr Leu Leu Pro Leu Asn Ala Ile Gln Ile
865 870 875 880

Glu Leu Leu Arg Arg Tyr Arg Ser Gly Asp Asp Ser Phe Leu Val Ser
885 890 895

Lys Thr Ile Gln Val Thr Met Asn Gly Leu Ala Thr Gly Leu Arg Val
900 905 910

Ser Gly

<210> SEQ ID NO 11
<211> LENGTH: 923
<212> TYPE: PRT
<213> ORGANISM: Corynebacterium pollutisoli VDS

<400> SEQUENCE: 11

Met Thr Val Arg Asp His Leu Gln Glu Asp Ile Arg Tyr Leu Gly Arg
1 5 10 15

Ile Leu Gly Gln Val Ile Ala Glu Gln Glu Gly Glu Asp Val Phe Asn
20 25 30

Leu Val Glu His Ala Arg Gln Gln Ala Phe Glu Val Ala Lys Gly Asn
35 40 45

Ala Ser Leu Glu Val Leu Val Asp Leu Phe Arg Asn Ile Asp Pro Glu
50 55 60

Arg Ala Thr Pro Val Val Arg Ala Phe Ser His Phe Ala Leu Met Ala
65 70 75 80

Asn Leu Ala Glu Asp Ile His Asp Asp Phe Asn Arg Glu Arg Ile Leu
85 90 95

Asp Glu Gly Gly Ala Pro Asp Ser Thr Leu Glu Ala Thr Trp Glu Lys
100 105 110

Phe Asp Glu Ala Asp Val Ser Ala Gly Asp Ile Glu Thr Ser Leu Ser
115 120 125

Ala Ala Leu Val Ala Pro Val Leu Thr Ala His Pro Thr Glu Thr Arg
130 135 140

Arg Arg Thr Val Phe Asp Ala Gln Lys His Ile Thr Asp Leu Met Leu
145 150 155 160

Ala Arg His Ala Ile Leu Asp Ala Glu Glu Thr Ala Arg Thr Glu Ala
165 170 175

Arg Leu Ala Asp Val Glu Arg Asn Ile Arg Arg Arg Met Thr Ile Leu
180 185 190

-continued

```
Trp Gln Thr Ala Leu Ile Arg Gln Ala Arg Pro Arg Ile Glu Asp Glu
        195                 200                 205

Ile Glu Val Gly Leu Arg Tyr Tyr Thr Leu Ser Leu Leu Lys Glu Ile
    210                 215                 220

Pro Ala Leu Asn Arg His Val His Asp Ser Leu Thr Asp Arg Phe Gly
225                 230                 235                 240

Ala Asp Leu Gln Gly Ser Asn Gly Gln Ala Ile Val Arg Pro Gly Ser
                245                 250                 255

Trp Ile Gly Gly Asp His Asp Gly Asn Pro Phe Val Thr Ala Ala Thr
            260                 265                 270

Leu Asp Tyr Ala Ser Arg Arg Ala Ala Gln Thr Val Leu Lys Tyr Tyr
        275                 280                 285

Ala Gln Gln Leu His Ala Leu Glu His Glu Leu Ser Leu Ser Asp Arg
    290                 295                 300

Met Thr Ser Val Thr Val Glu Leu Val Ala Leu Ala Gly Lys Gly Arg
305                 310                 315                 320

Asn Asp Val Pro Ser Arg Val Asp Glu Pro Tyr Arg Arg Ala Val His
                325                 330                 335

Gly Val Arg Gly Arg Ile Leu Ala Thr Thr Ala His Leu Ile Gly Glu
            340                 345                 350

Asp Ala Val Glu Gly Thr Trp His Arg Glu His Glu Pro Tyr Ile Asp
        355                 360                 365

Pro Ser Glu Phe Asp Ala Asp Leu Lys Val Ile Asp Thr Ser Leu Arg
    370                 375                 380

Ala Ser Gln Asp Glu Ile Ile Ala Asp Asp Arg Leu Ser Thr Ile Arg
385                 390                 395                 400

Ala Ala Ile Ala Ser Phe Gly Phe His Leu Tyr Ser Ile Asp Leu Arg
                405                 410                 415

Gln Asn Ser Glu Ser Phe Glu Asn Val Leu Thr Glu Val Phe Ala Thr
            420                 425                 430

Ala His Val His Pro Asn Tyr Asp Thr Leu Arg Glu Glu Glu Lys Val
        435                 440                 445

Glu Leu Leu Val Arg Glu Leu Gln Thr Pro Arg Pro Leu Val Pro Arg
    450                 455                 460

Gly Tyr Arg Gly Phe Ser Glu Ala Thr Gln Arg Glu Leu Asp Leu Ile
465                 470                 475                 480

Thr Gln Ala Ala Val Ser Val Glu Arg Phe Gly Glu Gln Met Ile Pro
                485                 490                 495

His Gln Ile Ile Ser Met Ala Gln Ser Val Ser Asp Ile Leu Glu Pro
            500                 505                 510

Met Val Leu Leu Lys Glu Val Gly Leu Ile Arg Ala Asn Gly Glu Gly
        515                 520                 525

Pro Thr Gly Ser Val Asp Ile Ile Pro Leu Phe Glu Thr Ile Asp Asp
    530                 535                 540

Leu Gln Ala Gly Ala Gly Ile Leu Arg Lys Leu Trp Asp Leu Pro Ile
545                 550                 555                 560

Tyr Arg Ala Tyr Leu Arg Gln Arg Gly Asp Ile Gln Glu Val Met Leu
                565                 570                 575

Gly Tyr Ser Asp Ser Asn Lys Asp Gly Gly Tyr Phe Ala Ala Asn Trp
            580                 585                 590

Ala Leu Tyr Asp Ala Glu Thr Asp Leu Val Glu Val Gly Arg Glu Tyr
        595                 600                 605

Gly Val Arg Leu Arg Leu Phe His Gly Arg Gly Gly Thr Val Gly Arg
```

-continued

```
    610                 615                 620

Gly Gly Gly Pro Ser Tyr Asp Ala Ile Leu Ala Gln Pro Gln Gly Ala
625                 630                 635                 640

Val Asp Gly Ser Val Arg Ile Thr Glu Gln Gly Glu Ile Ile Ser Ala
                645                 650                 655

Lys Tyr Gly Ser Glu Arg Ala Ala Arg Arg Asn Leu Glu Ala Leu Val
            660                 665                 670

Ser Ala Thr Leu Glu Ala Ser Leu Leu Thr Val Asp Asp Leu Glu Asp
        675                 680                 685

Arg Ala Arg Ala Thr Arg Ile Met Ser Glu Leu Ser Ala Ile Ser Arg
    690                 695                 700

Arg Lys Tyr Ser Glu Leu Val His Glu Asp Pro Gly Phe Ile Pro Tyr
705                 710                 715                 720

Phe Thr Gln Ser Thr Pro Leu His Glu Ile Gly Ser Leu Asn Ile Gly
                725                 730                 735

Ser Arg Pro Thr Ser Arg Lys Gln Thr Lys Gly Val Glu Asp Leu Arg
            740                 745                 750

Ala Ile Pro Trp Val Leu Ala Trp Ser Gln Ser Arg Val Leu Leu Pro
        755                 760                 765

Gly Trp Phe Gly Val Gly Thr Ala Leu Asp Glu Trp Ile Gly Asp Gly
    770                 775                 780

Glu Asp Arg Glu Glu Arg Ile Ala Glu Leu Arg His Leu Tyr Glu Thr
785                 790                 795                 800

Trp Pro Phe Phe Ala Ser Ile Met Ser Asn Met Ala Gln Val Met Ser
                805                 810                 815

Lys Ala Gly Met Asp Leu Ala Glu Leu Tyr Ala Arg Leu Ile Asp Asp
            820                 825                 830

Arg Glu Val Ala Asp Arg Val His Gly Val Ile Thr Ala Glu Phe Glu
        835                 840                 845

Leu Thr Arg Gly Met Phe Ser Thr Val Thr Gly Ser Glu Glu Leu Leu
    850                 855                 860

Ala Asp Asn Pro Ala Leu Ala Arg Ser Val Arg Arg Arg Phe Pro Tyr
865                 870                 875                 880

Leu Leu Pro Leu Asn Ile Ile Gln Leu Glu Met Leu Arg Arg His Arg
                885                 890                 895

Ala Gly Asp Ala Arg Gln Ala Val Ser Arg Gly Ile Gln Leu Thr Met
            900                 905                 910

Asn Gly Leu Ala Thr Ala Leu Arg Asn Ser Gly
        915                 920


<210> SEQ ID NO 12
<211> LENGTH: 940
<212> TYPE: PRT
<213> ORGANISM: Arthrobacter sp. PGP41

<400> SEQUENCE: 12

Met Ala His Thr Ala Met Asn Pro Glu Thr Asp Leu Ala Ser Glu Leu
1               5                   10                  15

Arg Ala Asp Val Arg Arg Val Ser Thr Leu Leu Gly Glu Ser Leu Val
            20                  25                  30

Arg Gln His Gly Pro Glu Leu Leu Asp Leu Val Glu Gln Val Arg Leu
        35                  40                  45

Leu Thr Lys Glu Ser Lys Glu Ala Ala Arg Gly Gly Ala Asp Ala Thr
    50                  55                  60
```

-continued

```
Gly Pro Trp Ser Ala His Asp Val Val Ala Gln Val Arg Glu Leu Leu
65                  70                  75                  80

Gly Ser Leu Pro Ile Gly Gln Ala Thr Asp Leu Val Arg Ala Phe Ala
                85                  90                  95

Phe Tyr Phe His Leu Ala Asn Ala Ala Glu Gln Val His Arg Val Arg
            100                 105                 110

Gly Leu Arg Thr Arg Ala Glu Lys Asp Gly Trp Leu Ala Lys Thr Ile
        115                 120                 125

Ala Asp Ile Ala Ser Gln Ala Gly Pro Gly Val Leu Gln Glu Val Val
    130                 135                 140

Asn Gly Leu Asp Val Arg Pro Ile Phe Thr Ala His Pro Thr Glu Ala
145                 150                 155                 160

Ser Arg Arg Ser Val Leu Asp Lys Ile Arg Lys Leu Ser Asp Val Leu
                165                 170                 175

Ala Gln Pro Thr Ala Glu Gly Thr Thr Ala Arg Arg Arg Gln Asp Arg
            180                 185                 190

Gln Leu Ala Glu Ile Ile Asp Gln Met Trp Gln Thr Asp Glu Leu Arg
        195                 200                 205

Gln Val Arg Pro Thr Pro Val Asp Glu Ala Arg Asn Ala Ile Tyr Tyr
    210                 215                 220

Leu Gly Ser Ile Leu Thr Asp Ala Met Pro Glu Met Leu Thr Glu Phe
225                 230                 235                 240

Ser Asp Leu Leu Ser Glu His Gly Val Thr Leu Ala Ser Gln Asp Ala
                245                 250                 255

Pro Ile Arg Phe Gly Ser Trp Ile Gly Gly Asp Arg Asp Gly Asn Pro
            260                 265                 270

Asn Val Thr Ala Ala Val Thr Arg Glu Ile Leu Gln Ile Gln Asn Gln
        275                 280                 285

His Ala Val Arg Ile Ser Ile Gly Met Ile Asp Glu Leu Ile Ser Ile
    290                 295                 300

Leu Ser Asn Ser Thr Ala Leu Ala Gly Ala Asp Gln Glu Leu Leu Asp
305                 310                 315                 320

Ser Ile Asp Ser Asp Leu Lys Asn Leu Pro Gly Leu Asp Lys Arg Val
                325                 330                 335

Leu Glu Leu Asn Ala Gln Glu Pro Tyr Arg Leu Lys Leu Thr Cys Ile
            340                 345                 350

Lys Ala Lys Leu Ile Asn Thr Gly Lys Arg Val Ala Ala Gly Ser Asn
        355                 360                 365

His Glu His Gly Arg Asp Tyr Ser Gly Thr Asp Glu Leu Leu Ala Asp
    370                 375                 380

Leu Glu Leu Leu Glu Arg Ser Leu Arg Asn His Ser Ala Ser Leu Ala
385                 390                 395                 400

Ala Asp Gly Ala Leu Ala Arg Val Arg Arg Ala Ile Ala Ser Phe Gly
                405                 410                 415

Leu His Leu Ala Thr Leu Asp Ile Arg Glu His Ala Asp His His His
            420                 425                 430

Asp Ala Val Gly Gln Leu Met Asp Arg Leu Gly Gly Pro Gly Leu Arg
        435                 440                 445

Tyr Ala Glu Leu Ser Arg Glu Glu Arg Phe Glu Val Leu Gly Ser Glu
    450                 455                 460

Leu Ala Ser Arg Arg Pro Leu Ser Gly His Pro Ile Lys Leu Asp Gly
465                 470                 475                 480

Ala Ala Asp Gly Thr Tyr Asp Val Phe Arg Glu Ile Arg Arg Ala Leu
```

-continued

```
                485                 490                 495

Arg Thr Tyr Gly Pro Asp Val Ile Glu Thr Tyr Ile Ile Ser Met Thr
            500                 505                 510

Arg Gly Ala Asp Asp Val Leu Ala Ala Ala Val Leu Ala Arg Glu Ala
        515                 520                 525

Gly Leu Val Asn Leu Phe Gly Glu Lys Pro Tyr Ala Lys Leu Gly Phe
    530                 535                 540

Ala Pro Leu Leu Glu Thr Val Glu Glu Leu Arg Ala Ser Ala Glu Ile
545                 550                 555                 560

Val Asp Gln Leu Leu Ser Asp Pro Ser Tyr Arg Glu Leu Val Arg Leu
                565                 570                 575

Arg Gly Asp Val Gln Glu Val Met Leu Gly Tyr Ser Asp Ser Asn Lys
            580                 585                 590

Glu Ser Gly Val Met Thr Ser Gln Trp Glu Ile His Lys Thr Gln Arg
        595                 600                 605

Lys Leu Arg Asp Val Ala Ala Lys His Gly Val Arg Val Arg Leu Phe
    610                 615                 620

His Gly Arg Gly Gly Ser Val Gly Arg Gly Gly Gly Pro Thr Tyr Asp
625                 630                 635                 640

Ala Ile Leu Ala Gln Pro Asn Gly Val Leu Glu Gly Glu Ile Lys Phe
                645                 650                 655

Thr Glu Gln Gly Glu Val Ile Ser Asp Lys Tyr Ser Leu Pro Glu Leu
            660                 665                 670

Ala Arg Glu Asn Leu Glu Leu Ser Leu Ala Ala Val Leu Gln Gly Ser
        675                 680                 685

Ala Leu His Lys Asp Pro Arg Thr Ser Ala Asp Gln Arg Glu Arg Tyr
    690                 695                 700

Gly His Val Met Glu Thr Ile Ser Asp Ala Ala Phe Asp Arg Tyr Arg
705                 710                 715                 720

Asn Leu Ile Asp Asn Pro Asp Leu Pro Ala Tyr Phe Met Ala Ser Thr
                725                 730                 735

Pro Val Glu Gln Leu Gly Ser Leu Asn Ile Gly Ser Arg Pro Ser Lys
            740                 745                 750

Arg Pro Asp Ser Gly Ala Gly Leu Gly Gly Leu Arg Ala Ile Pro Trp
        755                 760                 765

Val Phe Gly Trp Thr Gln Ser Arg Gln Ile Val Pro Gly Trp Phe Gly
    770                 775                 780

Val Gly Ser Gly Leu Lys Ala Ala Arg Glu Ala Gly Asn Ala Ala Gln
785                 790                 795                 800

Leu Val Glu Met Trp Glu Asn Trp His Phe Phe Arg Ser Val Leu Ser
                805                 810                 815

Asn Val Glu Met Thr Leu Ala Lys Thr Asp Leu Asp Ile Ala Gly Tyr
            820                 825                 830

Tyr Val Ser Thr Leu Val Pro Glu Glu Leu His His Ile Phe Arg Ser
        835                 840                 845

Ile Arg Glu Glu Tyr Glu Leu Thr Val Ala Glu Val Gln Asn Leu Thr
    850                 855                 860

Gly Glu Ser Leu Leu Leu Asp Ala Gln Pro Thr Leu Lys Arg Ser Leu
865                 870                 875                 880

Glu Ile Arg Asp Gln Tyr Leu Asp Pro Ile Ser Tyr Leu Gln Val Glu
                885                 890                 895

Leu Leu Arg Arg Val Arg Ala Glu Ala Ala Asp Ala Ala Asp Gly Ile
            900                 905                 910
```

```
Ser Gly Ala Glu Ile Asp Glu Arg Leu Gln Arg Ala Met Leu Ile Thr
        915                 920                 925

Val Asn Gly Val Ala Ala Gly Leu Arg Asn Thr Gly
    930                 935                 940


<210> SEQ ID NO 13
<211> LENGTH: 883
<212> TYPE: PRT
<213> ORGANISM: Escherichia coli str. K-12 substr. DH10B

<400> SEQUENCE: 13

Met Asn Glu Gln Tyr Ser Ala Leu Arg Ser Asn Val Ser Met Leu Gly
1               5                   10                  15

Lys Val Leu Gly Glu Thr Ile Lys Asp Ala Leu Gly Glu His Ile Leu
            20                  25                  30

Glu Arg Val Glu Thr Ile Arg Lys Leu Ser Lys Ser Ser Arg Ala Gly
        35                  40                  45

Asn Asp Ala Asn Arg Gln Glu Leu Leu Thr Thr Leu Gln Asn Leu Ser
    50                  55                  60

Asn Asp Glu Leu Leu Pro Val Ala Arg Ala Phe Ser Gln Phe Leu Asn
65                  70                  75                  80

Leu Ala Asn Thr Ala Glu Gln Tyr His Ser Ile Ser Pro Lys Gly Glu
                85                  90                  95

Ala Ala Ser Asn Pro Glu Val Ile Ala Arg Thr Leu Arg Lys Leu Lys
            100                 105                 110

Asn Gln Pro Glu Leu Ser Glu Asp Thr Ile Lys Lys Ala Val Glu Ser
        115                 120                 125

Leu Ser Leu Glu Leu Val Leu Thr Ala His Pro Thr Glu Ile Thr Arg
    130                 135                 140

Arg Thr Leu Ile His Lys Met Val Glu Val Asn Ala Cys Leu Lys Gln
145                 150                 155                 160

Leu Asp Asn Lys Asp Ile Ala Asp Tyr Glu His Asn Gln Leu Met Arg
                165                 170                 175

Arg Leu Arg Gln Leu Ile Ala Gln Ser Trp His Thr Asp Glu Ile Arg
            180                 185                 190

Lys Leu Arg Pro Ser Pro Val Asp Glu Ala Lys Trp Gly Phe Ala Val
        195                 200                 205

Val Glu Asn Ser Leu Trp Gln Gly Val Pro Asn Tyr Leu Arg Glu Leu
    210                 215                 220

Asn Glu Gln Leu Glu Glu Asn Leu Gly Tyr Lys Leu Pro Val Glu Phe
225                 230                 235                 240

Val Pro Val Arg Phe Thr Ser Trp Met Gly Gly Asp Arg Asp Gly Asn
                245                 250                 255

Pro Asn Val Thr Ala Asp Ile Thr Arg His Val Leu Leu Leu Ser Arg
            260                 265                 270

Trp Lys Ala Thr Asp Leu Phe Leu Lys Asp Ile Gln Val Leu Val Ser
        275                 280                 285

Glu Leu Ser Met Val Glu Ala Thr Pro Glu Leu Leu Ala Leu Val Gly
    290                 295                 300

Glu Glu Gly Ala Ala Glu Pro Tyr Arg Tyr Leu Met Lys Asn Leu Arg
305                 310                 315                 320

Ser Arg Leu Met Ala Thr Gln Ala Trp Leu Glu Ala Arg Leu Lys Gly
                325                 330                 335

Glu Glu Leu Pro Lys Pro Glu Gly Leu Leu Thr Gln Asn Glu Glu Leu
```

-continued

```
            340                 345                 350

Trp Glu Pro Leu Tyr Ala Cys Tyr Gln Ser Leu Gln Ala Cys Gly Met
        355                 360                 365

Gly Ile Ile Ala Asn Gly Asp Leu Leu Asp Thr Leu Arg Arg Val Lys
    370                 375                 380

Cys Phe Gly Val Pro Leu Val Arg Ile Asp Ile Arg Gln Glu Ser Thr
385                 390                 395                 400

Arg His Thr Glu Ala Leu Gly Glu Leu Thr Arg Tyr Leu Gly Ile Gly
                405                 410                 415

Asp Tyr Glu Ser Trp Ser Glu Ala Asp Lys Gln Ala Phe Leu Ile Arg
            420                 425                 430

Glu Leu Asn Ser Lys Arg Pro Leu Leu Pro Arg Asn Trp Gln Pro Ser
        435                 440                 445

Ala Glu Thr Arg Glu Val Leu Asp Thr Cys Gln Val Ile Ala Glu Ala
    450                 455                 460

Pro Gln Gly Ser Ile Ala Ala Tyr Val Ile Ser Met Ala Lys Thr Pro
465                 470                 475                 480

Ser Asp Val Leu Ala Val His Leu Leu Leu Lys Glu Ala Gly Ile Gly
                485                 490                 495

Phe Ala Met Pro Val Ala Pro Leu Phe Glu Thr Leu Asp Asp Leu Asn
            500                 505                 510

Asn Ala Asn Asp Val Met Thr Gln Leu Leu Asn Ile Asp Trp Tyr Arg
        515                 520                 525

Gly Leu Ile Gln Gly Lys Gln Met Val Met Ile Gly Tyr Ser Asp Ser
    530                 535                 540

Ala Lys Asp Ala Gly Val Met Ala Ala Ser Trp Ala Gln Tyr Gln Ala
545                 550                 555                 560

Gln Asp Ala Leu Ile Lys Thr Cys Glu Lys Ala Gly Ile Glu Leu Thr
                565                 570                 575

Leu Phe His Gly Arg Gly Gly Ser Ile Gly Arg Gly Gly Ala Pro Ala
            580                 585                 590

His Ala Ala Leu Leu Ser Gln Pro Pro Gly Ser Leu Lys Gly Gly Leu
        595                 600                 605

Arg Val Thr Glu Gln Gly Glu Met Ile Arg Phe Lys Tyr Gly Leu Pro
    610                 615                 620

Glu Ile Thr Val Ser Ser Leu Ser Leu Tyr Thr Gly Ala Ile Leu Glu
625                 630                 635                 640

Ala Asn Leu Leu Pro Pro Pro Glu Pro Lys Glu Ser Trp Arg Arg Ile
                645                 650                 655

Met Asp Glu Leu Ser Val Ile Ser Cys Asp Val Tyr Arg Gly Tyr Val
            660                 665                 670

Arg Glu Asn Lys Asp Phe Val Pro Tyr Phe Arg Ser Ala Thr Pro Glu
        675                 680                 685

Gln Glu Leu Gly Lys Leu Pro Leu Gly Ser Arg Pro Ala Lys Arg Arg
    690                 695                 700

Pro Thr Gly Gly Val Glu Ser Leu Arg Ala Ile Pro Trp Ile Phe Ala
705                 710                 715                 720

Trp Thr Gln Asn Arg Leu Met Leu Pro Ala Trp Leu Gly Ala Gly Thr
                725                 730                 735

Ala Leu Gln Lys Val Val Glu Asp Gly Lys Gln Ser Glu Leu Glu Ala
            740                 745                 750

Met Cys Arg Asp Trp Pro Phe Phe Ser Thr Arg Leu Gly Met Leu Glu
        755                 760                 765
```

```
Met Val Phe Ala Lys Ala Asp Leu Trp Leu Ala Glu Tyr Tyr Asp Gln
    770                 775                 780

Arg Leu Val Asp Lys Ala Leu Trp Pro Leu Gly Lys Glu Leu Arg Asn
785                 790                 795                 800

Leu Gln Glu Glu Asp Ile Lys Val Val Leu Ala Ile Ala Asn Asp Ser
                805                 810                 815

His Leu Met Ala Asp Leu Pro Trp Ile Ala Glu Ser Ile Gln Leu Arg
            820                 825                 830

Asn Ile Tyr Thr Asp Pro Leu Asn Val Leu Gln Ala Glu Leu Leu His
        835                 840                 845

Arg Ser Arg Gln Ala Glu Lys Glu Gly Gln Glu Pro Asp Pro Arg Val
    850                 855                 860

Glu Gln Ala Leu Met Val Thr Ile Ala Gly Ile Ala Ala Gly Met Arg
865                 870                 875                 880

Asn Thr Gly
```

<210> SEQ ID NO 14
<211> LENGTH: 30
<212> TYPE: DNA
<213> ORGANISM: Artificial Sequence
<220> FEATURE:
<223> OTHER INFORMATION: PCR primer

<400> SEQUENCE: 14
ggggaagctt gacgtccaca tatacctgcc 30

<210> SEQ ID NO 15
<211> LENGTH: 24
<212> TYPE: DNA
<213> ORGANISM: Artificial Sequence
<220> FEATURE:
<223> OTHER INFORMATION: PCR primer

<400> SEQUENCE: 15
attcggatcc gtatccacct ttac 24

<210> SEQ ID NO 16
<211> LENGTH: 35
<212> TYPE: DNA
<213> ORGANISM: Artificial Sequence
<220> FEATURE:
<223> OTHER INFORMATION: PCR primer

<400> SEQUENCE: 16
gacggccagt gaatttttca tacgaccacg ggcta 35

<210> SEQ ID NO 17
<211> LENGTH: 20
<212> TYPE: DNA
<213> ORGANISM: Artificial Sequence
<220> FEATURE:
<223> OTHER INFORMATION: PCR primer

<400> SEQUENCE: 17
gacaatcttg ttaccgacgg 20

<210> SEQ ID NO 18
<211> LENGTH: 35
<212> TYPE: DNA
<213> ORGANISM: Artificial Sequence
<220> FEATURE:
<223> OTHER INFORMATION: PCR primer

<400> SEQUENCE: 18
ggtaacaaga ttgtcaccct gcgcgaaatt cagaa 35

<210> SEQ ID NO 19
<211> LENGTH: 35
<212> TYPE: DNA
<213> ORGANISM: Artificial Sequence
<220> FEATURE:
<223> OTHER INFORMATION: PCR primer

<400> SEQUENCE: 19
taccgagctc gaattgaact cactgaaaaa tgctg 35

<210> SEQ ID NO 20
<211> LENGTH: 35
<212> TYPE: DNA
<213> ORGANISM: Artificial Sequence
<220> FEATURE:
<223> OTHER INFORMATION: PCR primer

<400> SEQUENCE: 20
gacggccagt gaattgcggc ggtcaagggc atcga 35

<210> SEQ ID NO 21
<211> LENGTH: 26
<212> TYPE: DNA
<213> ORGANISM: Artificial Sequence
<220> FEATURE:
<223> OTHER INFORMATION: PCR primer

<400> SEQUENCE: 21
gctagcggca cctccagtgt cgttgt 26

<210> SEQ ID NO 22
<211> LENGTH: 35
<212> TYPE: DNA
<213> ORGANISM: Artificial Sequence
<220> FEATURE:
<223> OTHER INFORMATION: PCR primer

<400> SEQUENCE: 22
ggaggtgccg ctagctcttt aatccaagta agtac 35

<210> SEQ ID NO 23
<211> LENGTH: 35
<212> TYPE: DNA
<213> ORGANISM: Artificial Sequence
<220> FEATURE:
<223> OTHER INFORMATION: PCR primer

<400> SEQUENCE: 23
taccgagctc gaattcttca aagtagttca gggtg 35

<210> SEQ ID NO 24
<211> LENGTH: 33
<212> TYPE: DNA
<213> ORGANISM: Artificial Sequence
<220> FEATURE:
<223> OTHER INFORMATION: PCR primer

<400> SEQUENCE: 24
gacggccagt gaaaacgtta atgaggaaaa ccg 33

<210> SEQ ID NO 25

<211> LENGTH: 20
<212> TYPE: DNA
<213> ORGANISM: Artificial Sequence
<220> FEATURE:
<223> OTHER INFORMATION: PCR primer

<400> SEQUENCE: 25
aattaattgt tctgcgtagc 20

<210> SEQ ID NO 26
<211> LENGTH: 41
<212> TYPE: DNA
<213> ORGANISM: Artificial Sequence
<220> FEATURE:
<223> OTHER INFORMATION: PCR primer

<400> SEQUENCE: 26
gcagaacaat taattctcga gtcgaacata aggaatattc c 41

<210> SEQ ID NO 27
<211> LENGTH: 35
<212> TYPE: DNA
<213> ORGANISM: Artificial Sequence
<220> FEATURE:
<223> OTHER INFORMATION: PCR primer

<400> SEQUENCE: 27
taccgagctc gaattttcca ggtacggaaa gtgcc 35

<210> SEQ ID NO 28
<211> LENGTH: 35
<212> TYPE: DNA
<213> ORGANISM: Artificial Sequence
<220> FEATURE:
<223> OTHER INFORMATION: PCR primer

<400> SEQUENCE: 28
tttctacgcg gccgcaacaa caagacccat catag 35

<210> SEQ ID NO 29
<211> LENGTH: 40
<212> TYPE: DNA
<213> ORGANISM: Artificial Sequence
<220> FEATURE:
<223> OTHER INFORMATION: PCR primer

<400> SEQUENCE: 29
tcgtcgacgg taccggatcc catgcacatg cagtcatgtc 40

<210> SEQ ID NO 30
<211> LENGTH: 35
<212> TYPE: DNA
<213> ORGANISM: Artificial Sequence
<220> FEATURE:
<223> OTHER INFORMATION: PCR primer

<400> SEQUENCE: 30
gaaccgtaaa aaggcgacag taagacgggt aagcc 35

<210> SEQ ID NO 31
<211> LENGTH: 35
<212> TYPE: DNA
<213> ORGANISM: Artificial Sequence
<220> FEATURE:
<223> OTHER INFORMATION: PCR primer

<400> SEQUENCE: 31
gcggccgcgt agaaagtaac ggtgaacagt tgttc 35

<210> SEQ ID NO 32
<211> LENGTH: 39
<212> TYPE: DNA
<213> ORGANISM: Artificial Sequence
<220> FEATURE:
<223> OTHER INFORMATION: PCR primer

<400> SEQUENCE: 32
cggtaccgtc gacgatatcg aggtctgcct cgtgaagaa 39

<210> SEQ ID NO 33
<211> LENGTH: 35
<212> TYPE: DNA
<213> ORGANISM: Artificial Sequence
<220> FEATURE:
<223> OTHER INFORMATION: PCR primer

<400> SEQUENCE: 33
gcctttttac ggttcgattt attcaacaaa gccgc 35

<210> SEQ ID NO 34
<211> LENGTH: 35
<212> TYPE: DNA
<213> ORGANISM: Artificial Sequence
<220> FEATURE:
<223> OTHER INFORMATION: PCR primer

<400> SEQUENCE: 34
catgtgcatg ggatcgaaga aatttagatg attga 35

<210> SEQ ID NO 35
<211> LENGTH: 20
<212> TYPE: DNA
<213> ORGANISM: Artificial Sequence
<220> FEATURE:
<223> OTHER INFORMATION: PCR primer

<400> SEQUENCE: 35
aaatccgtta ataccaacac 20

<210> SEQ ID NO 36
<211> LENGTH: 35
<212> TYPE: DNA
<213> ORGANISM: Artificial Sequence
<220> FEATURE:
<223> OTHER INFORMATION: PCR primer

<400> SEQUENCE: 36
ggtattaacg gatttatgac tgatttttta cgcga 35

<210> SEQ ID NO 37
<211> LENGTH: 29
<212> TYPE: DNA
<213> ORGANISM: Artificial Sequence
<220> FEATURE:
<223> OTHER INFORMATION: PCR primer

<400> SEQUENCE: 37
catgcggttc gacaggctga gctcatgct 29

<210> SEQ ID NO 38
<211> LENGTH: 29
<212> TYPE: DNA

<213> ORGANISM: Artificial Sequence
<220> FEATURE:
<223> OTHER INFORMATION: PCR primer

<400> SEQUENCE: 38
ctgtcgaacc gcatgaataa ggtcacccc 29

<210> SEQ ID NO 39
<211> LENGTH: 35
<212> TYPE: DNA
<213> ORGANISM: Artificial Sequence
<220> FEATURE:
<223> OTHER INFORMATION: PCR primer

<400> SEQUENCE: 39
cgacggtacc ggatcgctgg agagtccgcc gcctt 35

<210> SEQ ID NO 40
<211> LENGTH: 22
<212> TYPE: DNA
<213> ORGANISM: Artificial Sequence
<220> FEATURE:
<223> OTHER INFORMATION: PCR primer

<400> SEQUENCE: 40
cgaggacatc acctgagcca tg 22

<210> SEQ ID NO 41
<211> LENGTH: 35
<212> TYPE: DNA
<213> ORGANISM: Artificial Sequence
<220> FEATURE:
<223> OTHER INFORMATION: PCR primer

<400> SEQUENCE: 41
caggtgatgt cctcggcaga gctgcgtttg gcaaa 35

<210> SEQ ID NO 42
<211> LENGTH: 29
<212> TYPE: DNA
<213> ORGANISM: Artificial Sequence
<220> FEATURE:
<223> OTHER INFORMATION: PCR primer

<400> SEQUENCE: 42
gccggagccg cgcagcgcag tggaaagac 29

<210> SEQ ID NO 43
<211> LENGTH: 29
<212> TYPE: DNA
<213> ORGANISM: Artificial Sequence
<220> FEATURE:
<223> OTHER INFORMATION: PCR primer

<400> SEQUENCE: 43
ctgcgcggct ccggctagtc cagccggct 29

<210> SEQ ID NO 44
<211> LENGTH: 70
<212> TYPE: DNA
<213> ORGANISM: Artificial Sequence
<220> FEATURE:
<223> OTHER INFORMATION: PCR primer

<400> SEQUENCE: 44
cgaagtacgc agtaaataaa aaatccactt aagaaggtag gtgttacatg attccgggga 60
tccgtcgacc 70

<210> SEQ ID NO 45
<211> LENGTH: 70
<212> TYPE: DNA
<213> ORGANISM: Artificial Sequence
<220> FEATURE:
<223> OTHER INFORMATION: PCR primer

<400> SEQUENCE: 45
ttttactgta cgatttcagt caaatctaat tacatagatt gagtgaaggt tgtaggctgg 60
agctgcttcg 70

<210> SEQ ID NO 46
<211> LENGTH: 70
<212> TYPE: DNA
<213> ORGANISM: Artificial Sequence
<220> FEATURE:
<223> OTHER INFORMATION: PCR primer

<400> SEQUENCE: 46
ctgccgggaa atgactgtcc gcaaggaaaa gagtgtgagg aaaaacaatg attccgggga 60
tccgtcgacc 70

<210> SEQ ID NO 47
<211> LENGTH: 70
<212> TYPE: DNA
<213> ORGANISM: Artificial Sequence
<220> FEATURE:
<223> OTHER INFORMATION: PCR primer

<400> SEQUENCE: 47
aaagaagtaa tgttttcttc atcatcacct cagaaaagat cgctacgagt tgtaggctgg 60
agctgcttcg 70

<210> SEQ ID NO 48
<211> LENGTH: 70
<212> TYPE: DNA
<213> ORGANISM: Artificial Sequence
<220> FEATURE:
<223> OTHER INFORMATION: PCR primer

<400> SEQUENCE: 48
accctgaagt acgtggctgt gggataaaaa caatctggag gaatgtcgtg attccgggga 60
tccgtcgacc 70

<210> SEQ ID NO 49
<211> LENGTH: 70
<212> TYPE: DNA
<213> ORGANISM: Artificial Sequence
<220> FEATURE:
<223> OTHER INFORMATION: PCR primer

<400> SEQUENCE: 49
gcaccacctc aattttcagg tttttcatct cagccattcg ccttctcctt tgtaggctgg 60
agctgcttcg 70

GENETICALLY MODIFIED MICROORGANISM FOR PRODUCTION OF ASPARTIC ACID AND DOWNSTREAM METABOLITES FROM ASPARTIC ACID AS TARGET SUBSTANCE, AND METHOD FOR PRODUCING TARGET SUBSTANCE USING SAME

CROSS-REFERENCE TO RELATED APPLICATION

This application is a 371 of international application of PCT application serial no. PCT/JP2019/035286, filed on Sep. 6, 2019, which claims the priority benefit of Japan application no. 2019-076629, filed on Apr. 12, 2019. The entirety of each of the above-mentioned patent applications is hereby incorporated by reference herein and made a part of this specification.

TECHNICAL FIELD

The present invention relates to a genetically modified microorganism in which predetermined enzyme activity such as lactate dehydrogenase enzyme activity, succinate dehydrogenase enzyme activity, or fumarate reductase activity is reduced or inactivated and which has modified phosphoenolpyruvate carboxylase activity showing resistance to feedback inhibition by aspartic acid, and a method for producing a substance using the same.

Incidentally, this application claims priority based on Japanese Patent Application No. 2019-76629 (JP2019-76629) filed with the Japan Patent Office on Apr. 12, 2019, the contents of which are incorporated herein for reference for all purposes.

BACKGROUND ART

In substance production techniques using microorganisms, attempts have been made to improve production efficiency of various target substances, for example, by way of enhancing the activity of metabolic enzymes, or inactivating the activity of some of the metabolic enzymes, in metabolic systems involved in production of target substances from plant-derived sugars, based on gene recombination techniques or the like. For instance, production of many amino acids using microorganisms based on such techniques has been performed on the commercial level.

Meanwhile, there have been also amino acids produced from petroleum-derived raw materials. For example, fumaric acid that is synthesized from petroleum inexpensively in large quantities, has been used as a raw material for industrial production of aspartic acid, which is widely used as a raw material or the like for medical products, food additives, aspartame used as an artificial sweetener or the like, and polyaspartic acids serving as biodegradable resins. More specifically, a technique in which ammonia is added to fumaric acid synthesized from petroleum in such a way, followed by causing aspartase enzymes produced by microorganisms to act on the resultant, thereby synthesizing aspartic acid has been employed. Currently, it has become common to perform continuous enzyme reactions by way of immobilizing *E. coli* having high aspartase activity with k-carrageenan. However, it is a current situation that, after the former Tanabe Pharma Corporation established this method in 1973, any great technical innovations have not been developed in this field.

In the meantime, currently, few reports are available on development of any technologies that enables production of aspartic acid from glucose, serving as a carbon source less expensive than fumaric acid, based on bioengineering techniques involving microbial fermentation. If forced to give examples, most of techniques are limited to methods using aspartate dehydrogenase.

For example, Patent Document 1 describes a mutant-type aspartate dehydrogenase acquiring increased enzyme activity based on introduction of a mutation into a *Bacillus subtilis*-derived aspartate dehydrogenase, and a method for producing L-aspartic acid using the same. The method for producing L-aspartic acid described in Patent Document 1 practically adopts a technique in which the mutant-type aspartate dehydrogenase expressed in *E. coli* is purified, and the purified mutant type enzyme is employed to produce aspartic acid in an in-vitro enzyme reaction system. Therefore, strictly speaking, the method described in Patent Document 1 cannot be said to be a fermentative production technique for aspartic acid.

Moreover, searching for any aspartate dehydrogenases more suitable for fermentative production has also been conducted, and for example, in Patent Document 2, aspartate dehydrogenases derived from *Pseudomonas aeruginosa* strain PA01 and *Ralstonia eutropha* strain JM134, which exhibit high catalyst activity even at ordinary temperature, have been found, and a method for producing L-aspartic acid using these aspartate dehydrogenases is disclosed. More specifically, Patent Document 2 describes that strains of *E. coli* expressing the predetermined aspartate dehydrogenases were treated with toluene to prepare an enzyme mixture, followed by production of aspartic acid based on an in-vitro enzyme method using the enzyme mixture, and also describes that aspartic acid was produced based on culture fermentation using strains of *E. coli* introduced with the predetermined aspartate dehydrogenases, and using succinic acid as a substrate. Patent Document 2 also describes that, even in the case of using citric acid or glucose instead of succinic acid as a substrate in the culture fermentation, production of aspartic acid was recognized. However, Patent Document 2 does not at all show any specific data such as conversion efficiencies into aspartic acid from those substrates, and reaction rates. therefore, it is questionable whether the technique disclosed in Patent Document 2 can be considered to be suitable for industrial production of aspartic acid.

Additionally, it is described in the section of BACKGROUND ART of Patent Document 2 that, if the aspartate dehydrogenase derived from an archaeon *Archaeoglobus fulgidus*, disclosed in Patent Document 3, is employed, aspartic acid can be obtained. However, neither of Patent Documents 2 and 3 describe that aspartic acid was actually produced using the *Archaeoglobus fulgidus*-derived aspartate dehydrogenase.

Furthermore, Patent Document 4 discloses Enterobacteriaceae bacteria which produces L-aspartic acid or metabolites derived therefrom owing introduction of aspartate dehydrogenase, and a method for producing L-aspartic acid or metabolites derived therefrom using the bacteria. The bacteria disclosed in Patent Document 4 are specifically recombinants obtained by way of introducing various heterologous aspartate dehydrogenase genes derived from *Thermotoga maritima, Corynebacterium glutamicum*, and the like into *Escherichia coli* (*E. coli*) and the like. In Patent Document 4, it is shown that L-aspartic acid and its downstream metabolites can be increased to certain extents according to strains of *E. coli* imparted with the enzyme activities based on introduction of such heterologous aspartate dehydrogenase genes.

CITATION LIST

Patent Document

Patent Document 1: JP 2006-254795 A
Patent Document 2: JP 2010-183860 A
Patent Document 3: JP 2006-254730 A
Patent Document 4: JP 2013-516958 W
Patent Document 5: JP 2007-43947 A
Patent Document 6: JP H08(1996)-70860 A
Patent Document 7: JP 2003-503064 W

Non-Patent Document

Non-Patent Document 1: Litsanov B, Kabus A, Brocker M, Bott M. Microb Biotechnol. 2012 January; 5(1): 116-28.
Non-Patent Document 2: Chen Z, Bommareddy R R, Frank D, Rappert S, Zeng A P. Appl Environ Microbiol. 2014 February; 80(4): 1388-93.
Non-Patent Document 3: Wada M, Sawada K, Ogura K, Shimono Y, Hagiwara T, Sugimoto M, Onuki A, Yokota A. J Biosci Bioeng. 2016 February; 121(2): 172-7.
Non-Patent Document 4: Yano M1, Izui K. Eur J Biochem. 1997 Jul. 1; 247(1): 74-81.

SUMMARY OF THE INVENTION

Problem to be Solved by the Invention

As described above, aspartic acid is widely used as a raw material or the like for medical products, food additives, aspartame used as an artificial sweetener, and polyaspartic acid serving as a biodegradable resin. In addition to this, aspartic acid has an important role in microorganisms as an intermediate of additional metabolites such as β-alanine and asparagine. Therefore, it can be said that enhancement in the metabolic system up to aspartic acid is also important in development of fermentative production techniques for metabolites derived from aspartic acid.

However, in the current situation, the current industrial production of aspartic acid employs fumaric acid synthesized from petroleum inexpensively in large amounts, as a raw material, and any industrial production of aspartic acid based on fermentation techniques using biomass-derived sugars as raw materials has not yet been realized.

The reason why any industrial production of aspartic acid has not yet been realized as described above is considered as follows: there are problems in which, for example, even when microorganisms, such as *E. coli* or coryneform bacteria, which have industrially widely been used, are used as hosts for preparation of aspartic acid-producing strains, expression of an aspartate dehydrogenase gene would be deficient, and thus, an intended metabolic pathway cannot be constructed in microbial cells, since the aspartate dehydrogenase gene is an exogenous gene with respect to the hosts. Also in research and development conducted by the present Applicant, employment of aspartate dehydrogenase has actually been studied, but even when the enzyme protein coding gene was introduced into *E. coli* or coryneform bacteria, any strains producing aspartic acid in the microbial cells as intended could not be prepared. In fact, as described above, few reports are available on techniques for fermentative production of aspartic acid using aspartate dehydrogenase, there is no technique realizing production efficiency that is sufficiently applicable to industrial production, and there is also no report that such a technique is actually industrialized.

Thus, an object of the invention is to provide, instead of the conventional methods using aspartate dehydrogenase, a technique capable of producing aspartic acid or a metabolite derived therefrom from a sugar source by direct fermentation by microorganisms and capable of realizing production efficiency that is sufficiently applicable to industrial production.

In addition, Patent Document 4 describes the method for producing L-aspartic acid or its downstream metabolites using *E. coli* or the like modified to have various heterologous aspartate dehydrogenases, and, additionally describes inactivation of some metabolic enzymes such as α-ketoglutarate dehydrogenase and enhancement of some metabolic enzymes such as phosphoenolpyruvate carboxylase. However, since the technique disclosed in Patent Document 4 is a technique originally depending on the expression of various heterologous aspartate dehydrogenases in *E. coli* or the like, it is considered that sufficient amounts of heterologous enzyme protein expressed in the microbial cells is difficult to realize in such a technique. Therefore, Patent Document 4 neither describes nor suggests any insights on aspartic-acid or relevant-metabolite fermentative production that is applicable to industrial production.

Patent Document 5 discloses a method for producing amino acids using a coryneform bacterium in which lactate dehydrogenase is inactivated. However, Patent Document 5 is originally a technique focusing on production of all amino acids, and neither describes nor suggests any insights on aspartic-acid or relevant-metabolite fermentative production that is applicable to industrial production.

Patent Document 6 discloses that *E. coli* and *Corynebacterium glutamicum* each incorporated with a mutant-type *Escherichia coli*-derived phosphoenolpyruvate carboxylase having a mutation that cancels feedback inhibition by aspartic acid against phosphoenolpyruvate carboxylase were prepared, and further discloses that various amino acids were produced by use of these microbes. However, in fact, Patent Document 6 only describes that glutamic acid and lysine were produced by use of the microbes, and thus, Patent Document 6 neither describes nor suggests any insights on aspartic-acid or relevant-metabolite fermentative production that is applicable to industrial production.

Patent Document 7 discloses a recombinant bacterium, such as *Corynebacterium glutamicum*, incorporated with a modified phosphoenolpyruvate carboxylase gene that is derived from alfalfa, that does not require acetyl CoA as a coenzyme, and that is imparted with a property of hyposensitized feedback inhibition by aspartic acid, and also, formally describes a method for producing an amino acid using the recombinant bacterium. However, Patent Document 7 only describes that lysine was actually produced, and thus, neither describes nor suggests any insights on aspartic-acid or relevant-metabolite fermentative production that is applicable to industrial production.

Non-Patent Document 1 describes that, when predetermined metabolic enzymes such as succinate dehydrogenase (SDH) and pyruvate: quinone oxidoreductase (PQO) were inactivated, and a mutant-type pyruvate carboxylase having a predetermined single amino acid substitution, and wild-type phosphoenolpyruvate carboxylase were overexpressed, in *Corynebacterium glutamicum*, a yield of succinic acid was improved. Non-Patent Document 1 is a document that discloses a technique focusing on production of succinic acid, and thus, the document neither describes nor suggests any insights on aspartic-acid or relevant-metabolite fermentative production that is applicable to industrial production.

Non-Patent Document 2 shows that, when the *Corynebacterium glutamicum*-derived phosphoenolpyruvate carboxylase was subjected to a predetermined single amino acid substitution such as N917G, the resulting enzyme will retain the enzyme activity while having reduced feedback inhibition by aspartic acid or the like as compared to the wild type enzyme, and further shows that a yield of lysine will be improved in *Corynebacterium glutamicum* incorporated with a mutant-type ppc with the above single amino acid mutation. Since Non-Patent Document 2 only shows the production of lysine merely using the mutant-type ppc, Non-Patent Document 2 neither describes nor suggests any insights on aspartic-acid or relevant-metabolite fermentative production that is applicable to industrial production.

Non-Patent Document 3 shows that, when the *Corynebacterium glutamicum*-derived phosphoenolpyruvate carboxylase was subjected to a predetermined single amino acid substitution such as D299N, the resulting enzyme will retain the enzyme activity while having reduced feedback inhibition by aspartic acid, α-ketoglutaric acid or the like as compared to the wild type enzyme, and further shows that a yield of glutamic acid or aspartic acid will be improved in *Corynebacterium glutamicum* incorporated with a mutant-type ppc with the above single amino acid mutation. However, when the present inventor carried out a reproduction test for confirmation, a sufficient yield of aspartic acid could not be realized in *Corynebacterium glutamicum* incorporated with the mutant-type ppc described in Non-Patent Document 3 (for example, see the section of EXAMPLES described below). Therefore, Non-Patent Document 3 is not a document that describes any insights on aspartic-acid or relevant-metabolite fermentative production that is applicable to industrial production.

Non-Patent Document 4 describes that a mutant-type enzyme of *Escherichia coli*-derived phosphoenolpyruvate carboxylase, in which the 620th lysine is substituted with serine, shows a property of reduced feedback inhibition by aspartic acid and malic acid. Non-Patent Document 4 is merely an academic article in which, with respect to *Escherichia coli*-derived phosphoenolpyruvate carboxylase, influences of amino acid mutations on the aforementioned feedback inhibition were studied based on in-vitro assays using purified recombinant enzymes from the viewpoint of enzyme kinetics. Therefore, Non-Patent Document 4 is not a document that describes any insights on aspartic-acid or relevant-metabolite fermentative production that is applicable to industrial production.

Means for Solving Problem

The present inventor has conducted intensive studies in order to solve the aforementioned object, and, as a result, has found that, when predetermined enzyme activity such as succinate dehydrogenase activity, fumarate reductase activity or lactate dehydrogenase activity is inactivated in microorganisms, and also, modified phosphoenolpyruvate carboxylase activity exhibiting resistance to feedback inhibition by aspartic acid is imparted to the microorganisms, the production efficiency of aspartic acid or its relevant metabolites are improved. The invention has been achieved on the basis of such findings.

That is, according to the invention, the followings are provided.

[1] A genetically modified microorganism satisfying at least one of the following Conditions (I), (II), and (IV) and satisfying the following Condition (III):

Condition (I): succinate dehydrogenase activity or fumarate reductase activity is reduced or inactivated relative to a wild-type microorganism corresponding to the genetically modified microorganism;

Condition (II): lactate dehydrogenase activity is reduced or inactivated relative to the wild-type microorganism;

Condition (III): the genetically modified microorganism has modified phosphoenolpyruvate carboxylase activity showing resistance to feedback inhibition by aspartic acid in wild-type phosphoenolpyruvate carboxylase activity or exogenous phosphoenolpyruvate carboxylase activity having higher resistance to feedback inhibition by aspartic acid than that of the wild-type phosphoenolpyruvate carboxylase activity shown by the wild-type microorganism; and Condition (IV): pyruvate:quinone oxidoreductase activity is reduced or inactivated relative to the wild-type microorganism.

Herein, in some embodiments, the genetically modified microorganism may satisfy at least two of Conditions (I), (II), and (IV), and in a specific embodiment, the genetically modified microorganism may satisfy both of Conditions (I) and (II), both of Conditions (I) and (IV), or both of Conditions (II) and (IV).

[2] A genetically modified microorganism satisfying all of the following Conditions (I) to (III):

Condition (I): succinate dehydrogenase activity or fumarate reductase activity is reduced or inactivated relative to a wild-type microorganism corresponding to the genetically modified microorganism;

Condition (II): lactate dehydrogenase activity is reduced or inactivated relative to the wild-type microorganism; and Condition (III): the genetically modified microorganism has modified phosphoenolpyruvate carboxylase activity showing resistance to feedback inhibition by aspartic acid in wild-type phosphoenolpyruvate carboxylase activity or exogenous phosphoenolpyruvate carboxylase activity having higher resistance to feedback inhibition by aspartic acid than that of the wild-type phosphoenolpyruvate carboxylase activity shown by the wild-type microorganism.

[3] The genetically modified microorganism according to [2], further satisfying Condition (IV): pyruvate:quinone oxidoreductase is reduced or inactivated relative to the wild-type microorganism.

[4] The genetically modified microorganism according to any one of [1] to [3] into which a nucleic acid coding for a bacteria-derived mutant-type phosphoenolpyruvate carboxylase is introduced in a form capable of expressing the mutant-type phosphoenolpyruvate carboxylase, wherein the mutant-type phosphoenolpyruvate carboxylase has at least one amino acid mutation causing the genetically modified microorganism to satisfy Condition (IV).

Meanwhile, other embodiments for which the "nucleic acid coding for a bacteria-derived mutant-type phosphoenolpyruvate carboxylase" is replaced with a "nucleic acid coding for a microorganism-derived, plant-derived, prokaryote-derived or bacteria-derived exogenous phosphoenolpyruvate carboxylase" in [4] can also be adopted in the present invention.

[5] The genetically modified microorganism according to [4], in which the mutant-type phosphoenolpyruvate carboxylase is derived from a coryneform bacterium.

[6] The genetically modified microorganism according to [4] or [5], wherein the mutant-type phosphoenolpyruvate carboxylase is derived from a bacterium belonging to the genus *Corynebacterium.*

[7] The genetically modified microorganism according to any one of [4] to [6], wherein the at least one amino acid mutation in the mutant-type phosphoenolpyruvate carboxylase includes at least one selected from the group consisting of amino acid substitutions shown in the following (a) to (f) based on the amino acid sequence set forth in SEQ ID NO: 2:

(a) an amino acid substitution of an amino acid corresponding to the 299th aspartic acid with a predetermined amino acid, wherein the substituted amino acid is not aspartic acid, and the substitution is preferably an amino acid substitution with alanine, asparagine, glycine, or serine;

(b) an amino acid substitution of an amino acid corresponding to the 653rd lysine with a predetermined amino acid, wherein the substituted amino acid is not lysine, and the substitution is preferably an amino acid substitution with alanine, asparagine, or serine;

(c) an amino acid substitution of an amino acid corresponding to the 813th lysine with a predetermined amino acid, wherein the substituted amino acid is not lysine, and the substitution is preferably an amino acid substitution with alanine, asparagine, glycine, or serine;

(d) an amino acid substitution of an amino acid corresponding to the 869th serine with a predetermined amino acid, wherein the substituted amino acid is not serine, and the substitution is preferably an amino acid substitution with alanine, asparagine, or glycine;

(e) an amino acid substitution of an amino acid corresponding to the 873rd arginine with a predetermined amino acid, wherein the substituted amino acid is not arginine, and the substitution is preferably an amino acid substitution with alanine, asparagine, glycine, or serine; and (f) an amino acid substitution of an amino acid corresponding to the 917th asparagine with a predetermined amino acid, wherein the substituted amino acid is not asparagine, and the substitution is preferably an amino acid substitution with alanine, phenylalanine, glycine, or serine, wherein the amino acid before substitution and the substituted amino acid are different from each other in (a) to (f) above.

[8] The genetically modified microorganism according to any one of [4] to [7], wherein the at least one amino acid mutation in the mutant-type phosphoenolpyruvate carboxylase includes at least one selected from the group consisting of amino acid substitutions shown in the following (g) to (l) based on the amino acid sequence set forth in SEQ ID NO: 2:

(g) an amino acid substitution of an amino acid corresponding to the 299th aspartic acid with asparagine;

(h) an amino acid substitution of an amino acid corresponding to the 653rd lysine with serine;

(i) an amino acid substitution of an amino acid corresponding to the 813th lysine with a predetermined amino acid, wherein the substituted amino acid is not lysine, and the substitution is preferably an amino acid substitution with glycine or serine;

(j) an amino acid substitution of an amino acid corresponding to the 869th serine with glycine;

(k) an amino acid substitution of an amino acid corresponding to the 873rd arginine with glycine; and (l) an amino acid substitution of an amino acid corresponding to the 917th asparagine with a predetermined amino acid, wherein the substituted amino acid is not asparagine, and the substitution is preferably an amino acid substitution with alanine, phenylalanine, glycine, or serine.

[9] The genetically modified microorganism according to [8], wherein the at least one amino acid mutation in the mutant-type phosphoenolpyruvate carboxylase includes the amino acid substitution shown in (g) above and at least one of the amino acid substitutions shown in (h) to (l) above.

[10] The genetically modified microorganism according to [8] or [9], wherein the at least one amino acid mutation in the mutant-type phosphoenolpyruvate carboxylase includes the amino acid substitution shown in (g) above and amino acid substitution shown in (i) or (l) above.

[11] The genetically modified microorganism according to any one of [4] to [10], in which the mutant-type phosphoenolpyruvate carboxylase has an amino acid sequence set forth in any one of the following (A), (B), and (C):

(A) an amino acid sequence obtained by introducing the at least one amino acid substitution into an amino acid sequence set forth in any one of SEQ ID NOs: 2 to 13, preferably SEQ ID NOs: 2 to 12, more preferably SEQ ID NOs: 2 to 11;

(B) an amino acid sequence having deletion, substitution, and/or addition of one or more amino acids in the amino acid sequence defined in (A) above, wherein the at least one amino acid substitution has been maintained; and (C) an amino acid sequence having a sequence identity of at least 60% to the amino acid sequence defined in (A) above, wherein the at least one amino acid substitution has been maintained.

[12] The genetically modified microorganism according to [11], wherein the amino acid sequence defined in (A) above is an amino acid sequence obtained by introducing the at least one amino acid substitution into the amino acid sequence set forth in SEQ ID NO: 2. [13] The genetically modified microorganism according to any one of [4] to [12], wherein the mutant-type phosphoenolpyruvate carboxylase has an amino acid sequence obtained by introducing the at least one amino acid substitution into the amino acid sequence set forth in SEQ ID NO: 2.

[14] A mutant-type phosphoenolpyruvate carboxylase comprising an amino acid mutation with respect to an amino acid sequence of a wild-type phosphoenolpyruvate carboxylase of a microorganism belonging to coryneform bacteria, the amino acid mutation being capable of reducing feedback inhibition by aspartic acid in the wild-type phosphoenolpyruvate carboxylase activity, wherein the amino acid mutation at least includes: based on the amino acid sequence set forth in SEQ ID NO: 2, (g) an amino acid substitution of an amino acid corresponding to the 299th aspartic acid with asparagine;

(i) an amino acid substitution of an amino acid corresponding to the 813th lysine with a predetermined amino acid, wherein the substituted amino acid is not lysine; or (l) an amino acid substitution of an amino acid corresponding to the 917th asparagine with a predetermined amino acid, wherein the substituted amino acid is not asparagine, wherein the mutant-type phosphoenolpyruvate carboxylase has higher resistance to feedback inhibition by aspartic acid than that of a protein having only the amino acid substitution defined in (g), (i), or (l) above.

In the mutant-type phosphoenolpyruvate carboxylase according to [14], in (i) above, the amino acid corresponding to the 813th lysine is substituted preferably with alanine, asparagine, glycine or serine, more preferably with glycine or serine, and most preferably with serine. Furthermore, in (l) above, the amino acid corresponding to the 917th asparagine is substituted preferably with alanine, phenylalanine, glycine or serine and more preferably with phenylalanine or glycine.

[15] The mutant-type phosphoenolpyruvate carboxylase according to [14], wherein the mutant-type phosphoenolpyruvate carboxylase has an amino acid mutation with respect to an amino acid sequence of a wild-type phosphoenolpyruvate carboxylase of a microorganism belonging to the genus *Corynebacterium.*

[16] The mutant-type phosphoenolpyruvate carboxylase according to [14] or [15], wherein the mutant-type phosphoenolpyruvate carboxylase has an amino acid sequence set forth in any one of the following (J), (K), and (L):

(J) an amino acid sequence obtained by introducing the amino acid substitution into an amino acid sequence set forth in in any one of SEQ ID NOs: 2 to 13, preferably SEQ ID NOs: 2 to 12, more preferably SEQ ID NOs: 2 to 11;

(K) an amino acid sequence having deletion, substitution, and/or addition of one or more amino acids in the amino acid sequence defined in (J) above, wherein the above amino acid substitution has been maintained; and (L) an amino acid sequence having a sequence identity of at least 60% to the amino acid sequence defined in (J) above, wherein the above amino acid substitution has been maintained.

[17] The mutant-type phosphoenolpyruvate carboxylase according to [16], wherein the amino acid sequence defined in (J) above is an amino acid sequence obtained by introducing the amino acid substitution into the amino acid sequence set forth in SEQ ID NO: 2.

[18] The mutant-type phosphoenolpyruvate carboxylase according to any one of [14] to [17], wherein the mutant-type phosphoenolpyruvate carboxylase has an amino acid sequence obtained by introducing the amino acid substitution into the amino acid sequence set forth in any one of SEQ ID NOs: 2 to 13, preferably SEQ ID NOs: 2 to 12, more preferably SEQ ID NOs: 2 to 11.

[19] A nucleic acid coding for the mutant-type phosphoenolpyruvate carboxylase according to any one of [14] to [18].

[20] The nucleic acid according to [19], wherein the nucleic acid is a DNA fragment.

[21] A genetically modified microorganism into which the nucleic acid according to [19] or [20] is introduced.

[22] The genetically modified microorganism described in [21], satisfying the following Condition (I) or (II) and satisfying Condition (III):

Condition (I): succinate dehydrogenase activity or fumarate reductase activity is reduced or inactivated relative to a wild-type microorganism corresponding to the genetically modified microorganism;

Condition (II): lactate dehydrogenase activity is reduced or inactivated relative to the wild-type microorganism; and Condition (III): the genetically modified microorganism has modified phosphoenolpyruvate carboxylase activity showing resistance to feedback inhibition by aspartic acid in wild-type phosphoenolpyruvate carboxylase activity, or exogenous phosphoenolpyruvate carboxylase activity having higher resistance to feedback inhibition by aspartic acid than that of the wild-type phosphoenolpyruvate carboxylase activity shown by the wild-type microorganism.

[23] The genetically modified microorganism according to [22], satisfying both of Conditions (I) and (II).

[24] The genetically modified microorganism according to [22] or [23], satisfying all of Conditions (I) to (III).

[25] The genetically modified microorganism according to any one of [1] to [13] and [21] to [24], further satisfying Condition (IV): pyruvate:quinone oxidoreductase is reduced or inactivated relative to the wild-type microorganism corresponding to the genetically modified microorganism.

[26] The genetically modified microorganism according to any one of [1] to [13] and [21] to [25], wherein the genetically modified microorganism is a genetically modified microorganism belonging to bacteria.

[27] The genetically modified microorganism according to any one of [1] to [13] and [21] to [26], wherein the genetically modified microorganism is a genetically modified microorganism belonging to Gram-positive bacteria.

[28] The genetically modified microorganism according to [27], wherein the genetically modified microorganism is a genetically modified microorganism belonging to coryneform bacteria.

[29] The genetically modified microorganism according to [28], wherein the genetically modified microorganism is a genetically modified microorganism belonging to the genus *Corynebacterium.*

[30] The genetically modified microorganism d according to [29], wherein the genetically modified microorganism is a genetically modified strain of *Corynebacterium glutamicum.*

[31] The genetically modified microorganism according to any one of [1] to [13] and [21] to [26], wherein the genetically modified microorganism is a genetically modified microorganism belonging to Gram-negative bacteria.

[32] The genetically modified microorganism according to [31], wherein the genetically modified microorganism is a genetically modified microorganism belonging to the genus *Escherichia.*

[33] The genetically modified microorganism according to [32], wherein the genetically modified microorganism is a genetically modified microorganism of *Escherichia coli.*

[34] The genetically modified microorganism according to any one of [31] to [33], further satisfying Condition (V): pyruvate formate-lyase activity is reduced or inactivated relative to the wild-type microorganism.

[35] The genetically modified microorganism according to any one of claims [1] to [13] and [21] to [34], wherein satisfaction of Condition (I) and/or Condition (II) and/or Condition (IV) and/or Condition (V) in the genetically modified microorganism is realized by complete or partial disruption of a coding region for a succinate dehydrogenase gene or a fumarate reductase gene, and/or a coding region for a lactate dehydrogenase gene, and/or a coding region for a pyruvate:quinone oxidoreductase gene, and/or a coding region for a pyruvate formate-lyase gene in chromosomal DNA of the genetically modified microorganism.

[36] The genetically modified microorganism according to any one of claims [1] to [13] and [21] to [35], wherein Condition (I) and/or Condition (II) and/or Condition (IV), and/or Condition (V) in the genetically modified microorganism are each realized by complete or partial disruption of a gene expression regulation region existing upstream of each of coding regions for a succinate dehydrogenase gene or a fumarate reductase gene, and/or a lactate dehydrogenase gene, and/or a pyruvate:quinone oxidoreductase gene, and/ or a pyruvate formate-lyase gene in chromosomal DNA of the genetically modified microorganism.

[37] A method for producing a target substance, the method including:

(p) producing a target substance using cells of the genetically modified microorganism according to any one of [1] to [13] and [21] to [36] or a treated cell product thereof; and (q) recovering the target substance.

[38] The method according to [37], wherein, in Step (p), the target substance is produced by reacting the cells of the genetically modified microorganism or the treated cell product thereof in a reaction medium (X) under reducing conditions where the genetically modified microorganism does not substantially proliferate.

[39] The method according to [38], wherein an oxidation-reduction potential of the reaction medium (X) is a predetermined value within the range of −200 mV to −500 mV.

[40] The method d according to [38] or [39], wherein the reaction medium (X) includes a sugar.

[41] The method according to any one of [38] to [40], wherein the reaction medium (X) includes glucose.

[42] The method according to any one of [37] to [41], further including, before Step (p), (p') culturing and proliferating the genetically modified microorganism under aerobic conditions in a predetermined culture medium (Y), wherein cells of the genetically modified microorganism proliferated in Step (p') or a treated cell product thereof are subjected to the step (p).

[43] The method according to any one of [37] to [42], wherein the target substance is oxaloacetic acid, malic acid, or a metabolite produced via these compounds in a biosynthetic pathway.

[44] The method according to any one of [37] to [43], wherein the target substance is aspartic acid or a metabolite derived therefrom.

[45] The method according to any one of [37] to [44], wherein the target substance is aspartic acid, beta alanine, or asparagine.

Effect of the Invention

According to the invention, the production efficiency of aspartic acid or a metabolite produced in a metabolic pathway derived therefrom will be improved, and, as a result, the yield of a target substance can be improved. In addition, according to the invention, the conversion efficiency of a starting substrate such as a sugar into a target substance will be improved, and, as a result, energy saving, cost reduction, and efficient substance production in bioprocesses can be realized.

Hereinafter, embodiments and modifications that can be further adopted in aspects of the invention will be exemplified, and also, advantages and effects of the invention will be described.

BRIEF DESCRIPTION OF DRAWINGS

FIG. 3A is a diagram showing a part of results obtained by subjecting various wild-type phosphoenolpyruvate carboxylase protein sequences to multiple alignment analysis.

FIG. 3B is a diagram showing another part of results obtained by the multiple alignment analysis in FIG. 3A.

FIG. 3C is a diagram showing still another part of results obtained by the multiple alignment analysis in FIG. 3A.

MODE(S) FOR CARRYING OUT THE INVENTION

<Genetically Modified Microorganism>

Figure 1:
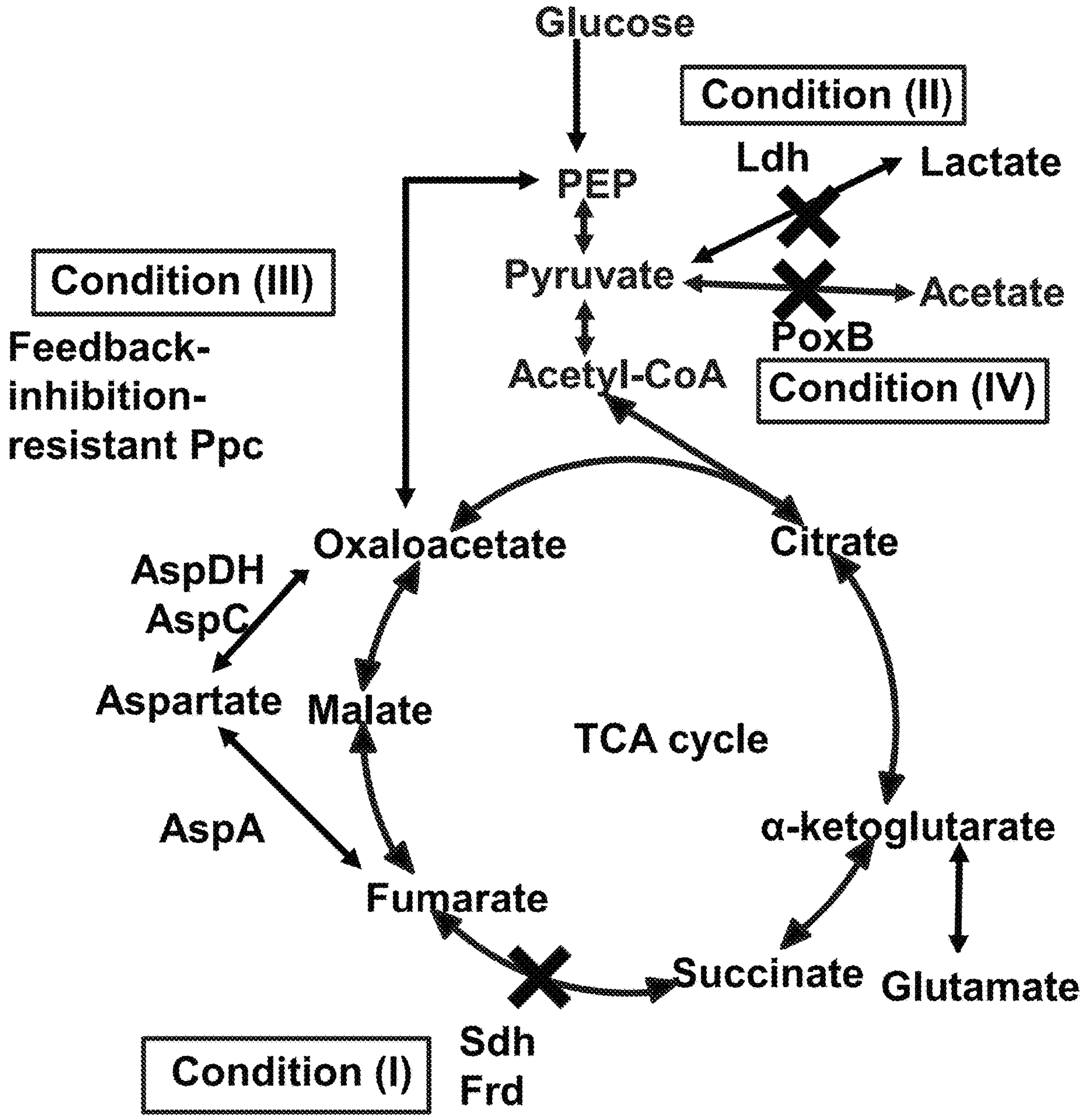
FIG. 1 is a diagram showing a metabolic pathway which can be adopted in some embodiments of the invention.

According to a first aspect of the invention, provided is the following genetically modified microorganism.

A genetically modified microorganism satisfying at least one of the following Conditions (I), (II), and (IV) and satisfying the following Condition (III):

Condition (I): succinate dehydrogenase activity or fumarate reductase activity is reduced or inactivated relative to a wild-type microorganism corresponding to the genetically modified microorganism;

Condition (II): lactate dehydrogenase activity is reduced or inactivated relative to the wild-type microorganism;

Condition (III): the genetically modified microorganism has modified phosphoenolpyruvate carboxylase activity showing resistance to feedback inhibition by aspartic acid in wild-type phosphoenolpyruvate carboxylase activity or exogenous phosphoenolpyruvate carboxylase activity having higher resistance to feedback inhibition by aspartic acid than that of the wild-type phosphoenolpyruvate carboxylase activity shown by the wild-type microorganism; and Condition (IV): pyruvate:quinone oxidoreductase activity is reduced or inactivated relative to the wild-type microorganism.

Furthermore, according to a second aspect of the invention, provided is the following genetically modified microorganism.

A genetically modified microorganism satisfying all of the following Conditions (I) to (III):

Condition (I): succinate dehydrogenase activity or fumarate reductase activity is reduced or inactivated relative to a wild-type microorganism corresponding to the genetically modified microorganism;

Condition (II): lactate dehydrogenase activity is reduced or inactivated relative to the wild-type microorganism; and Condition (III): the genetically modified microorganism has modified phosphoenolpyruvate carboxylase activity showing resistance to feedback inhibition by aspartic acid in wild-type phosphoenolpyruvate carboxylase activity or exogenous phosphoenolpyruvate carboxylase activity having higher resistance to feedback inhibition by aspartic acid than that of the wild-type phosphoenolpyruvate carboxylase activity shown by the wild-type microorganism.

In addition, hereinafter, the genetically modified microorganism according to the first aspect of the invention and the genetically modified microorganism according to the second aspect of the invention may be collectively referred to as "the genetically modified microorganism of the invention" or "the genetically modified microorganism according to the invention."

In the invention, the "genetically modified microorganism" is sufficient to be literally understood, and thus, is sufficient to be understood that the genetically modified microorganism is a microorganism which has been subjected to any gene modifications. More specifically, such a genetic modifications may be those that realize a predetermined combination of Conditions (I) to (IV) above within the realm defined for each of the genetically modified microorganisms according to the first and second aspects of the invention.

In the invention, the "microorganism" is sufficient to be literally understood. More specifically, the "microorganism" and "genetically modified microorganism" in the invention may be fungi, or prokaryotes such as archaea, cyanobacteria and bacteria. In the invention, the "microorganism" and the "genetically modified microorganism" are preferably fungi or bacteria, and more preferably bacteria.

Examples of fungi include yeasts of the genus *Saccharomyces* (e.g., *Saccharomyces cerevisiae*), yeasts of the genus *Schizosaccharomyces* (e.g., *Schizosaccharomyces pombe*), yeasts of the genus *Pichia* (e.g., *Pichia pastoris*), yeasts of the genus *Kluyveromyces* (*Kluyveromyces lactis*), *Hansenula polymorpha*, yeasts of the genus *Yarrowia* (e.g., *Yarrowia lipolytica*), fungi of the genus *Cryptococcus* (e.g., *Cryptococcus* sp. S-2), fungi of the genus *Aspergillus* (e.g., *Aspergillus oryzae*), and fungi of the genus *Pseudozyma* (e.g., *Pseudozyma antarctica*). *Saccharomyces cerevisiae, Schizosaccharomyces pombe, Pichia pastoris*, and the like can be conveniently used in the invention since gene manipulation techniques or heterologous protein expression systems therefor are established.

Examples of the bacteria include the genus *Escherichia* (e.g., *Escherichia coli*), the genus *Bacillus* (e.g., *Bacillus subtilis*), the genus *Lactobacillus* (e.g., *Lactobacillus acidophilus*), the genus *Clostridium* (e.g., *Clostridium thermocellum* and *Clostridium acetobutylicum*), the genus *Rhodopseudomonas* (e.g., *Rhodopseudomonas palustris*), the genus *Rhodobacter* (*Rhodobacter capsulatus*), and bacteria belonging to coryneform bacteria specifically described below. The "microorganism" and "genetically modified microorganism" in the invention are preferably the genus *Escherichia* or coryneform bacteria, more preferably *Escherichia coli* or coryneform bacteria, most preferably the genus *Corynebacterium*, for which genetic manipulation techniques or protein expression systems have already been established and which enable substance production under reducing conditions where the bacterial cells do not substantially proliferate.

Moreover, in some embodiments, the genetically modified microorganism according to the invention is a microorganism belonging to Gram-positive bacteria (e.g., actinomycetes). Furthermore, in other some embodiments, the genetically modified microorganism according to the invention may be a microorganism belonging to Gram-negative bacteria. The Gram-negative bacteria specifically are microorganisms belonging to the phylum Proteobacteria, and more particularly include microorganisms belonging to the class Alpha-, Beta-, Gamma-, Delta-, Epsilon-, or Zeta-proteobacteria, and microorganisms belonging to the class Oligoflexia. Examples of the Gram-negative bacteria which can be preferably used in the invention include microorganisms belonging to the family Enterobacteriaceae, the family Vibrionaceae, or the family Pseudomonadaceae.

Herein, the "coryneform bacteria" refer to a group of microorganisms defined in Bargey's Manual of Determinative Bacteriology (8th Ed., p. 599, 1974).

More particularly, examples of coryneform bacteria include the genus *Corynebacterium*, the genus *Brevibacterium*, the genus *Arthrobacter*, the genus *Mycobacterium*, the genus *Micrococcus*, and the genus *Microbacterium.*

Examples of the genus *Corynebacterium* include species and strains as described below: *Corynebacterium glutamicum* (e.g., strains FERM P-18976, ATCC13032, ATCC31831 strain, ATCC13058, ATCC13059, ATCC13060, ATCC13232, ATCC13286, ATCC13287, ATCC13655, ATCC13745, ATCC13746, ATCC13761, and ATCC14020);

*Corynebacterium acetoglutamicum* (e.g., strain ATCC15806);

*Corynebacterium acetoacidophilum* (e.g., strain ATCC13870);

*Corynebacterium melassecola* (e.g., strain ATCC17965);

*Corynebacterium efficiens* (e.g., strain YS-314, strain YS-314$^T$ (strain NBRC100395$^T$));

*Corynebacterium alkanolyticum* (e.g., strain ATCC21511);

*Corynebacterium callunae* (e.g., strains ATCC15991, NBRC15359 strain, and DSM20147);

*Corynebacterium lilium* (e.g., strain ATCC15990);

*Corynebacterium thermoaminogenes* (*Corynebacterium efficiens*) (e.g., strains AJ12340 and FERM BP1539);

*Corynebacterium herculis* (e.g., strain ATCC13868);

*Corynebacterium ammoniagenes* (*Brevibacterium ammoniagenes*) (e.g., strains ATCC6871, ATCC6872, DSM20306, NBRC12071$^T$, NBRC12072, and NBRC12612$^T$);

*Corynebacterium pollutisoli;*

*Corynebacterium marinum* (e.g., strain DSM44953);

*Corynebacterium humireducens* (e.g., strain NBRC106098);

*Corynebacterium halotolerans* (e.g., strain YIM70093);

*Corynebacterium deserti* (e.g., strain GIMN1.010);

*Corynebacterium doosanense* (e.g., strains CAU212, and DSM45436); and

*Corynebacterium maris* (e.g., strain DSM45190).

Specific examples of the genus *Brevibacterium* include the following species and strains: *Brevibacterium divaricatum* (e.g., strain ATCC14020);

*Brevibacterium flavum* [e.g., strains MJ-233 (FERM BP-1497), MJ-233AB-41 (FERM BP-1498), ATCC13826, ATCC14067, and ATCC13826];

*Brevibacterium immariophilum* (e.g., strain ATCC14068);

*Brevibacterium lactofermentum* (*Corynebacterium glutamicum*) (e.g., strain ATCC13869);

*Brevibacterium roseum* (e.g., strain ATCC13825);

*Brevibacterium saccharolyticum* (e.g., strain ATCC14066);

*Brevibacterium thiogenitalis* (e.g., strain ATCC19240);

*Brevibacterium album* (e.g., strain ATCC15111); and

*Brevibacterium cerinum* (e.g., strain ATCC15112).

Specific examples of the genus *Arthrobacter* include species and strains as described below: *Arthrobacter globiformis* (e.g., strains ATCC8010, ATCC4336, ATCC21056, ATCC31250, ATCC31738, ATCC35698, NBRC3062, and NBRC12137T).

Specific examples of the genus *Micrococcus* include *Micrococcus freudenreichii* [e.g., strain No. 239 (FERM P-13221)]; *Micrococcus luteus* [e.g., strain NCTC2665, No. 240 (FERM P-13222)]; *Micrococcus ureae* (e.g., strain IAM1010); and *Micrococcus roseus* (e.g., strain IFO3764).

Specific examples of the genus *Microbacterium* include *Microbacterium ammoniaphilum* (e.g., strain ATCC15354).

Additionally, for example, in the case of ATCC strains among the above-described strains of coryneform bacteria, the strains are available from American Type Culture Collection (P.O. Box 1549 Manassas, VA 20108 USA) that provides those strains. Other strains would also be available from respective microbial culture collections that provide those strains.

The genetically modified microorganism according to the invention can be prepared by subjecting the microorganism exemplified above to a predetermined gene manipulation.

[Conditions (I), (II), (IV), and (V)]

At first, Conditions (I), (II), and (IV) will be described.

The expression "succinate dehydrogenase activity or fumarate reductase activity is reduced or inactivated relative to a wild-type microorganism corresponding to the genetically modified microorganism" in Condition (I) means that a succinate dehydrogenase or fumarate reductase activity is significantly reduced or completely inactivated relative to a wild-type microorganism that is used as a starting material for preparation of the genetically modified microorganism according to the invention. Additionally, some of bacteria such as the genus *Corynebacterium* do not have fumarate reductase, and succinate dehydrogenase catalyzes this reaction. However, some of bacteria such as *E. coli* have both enzymes of succinate dehydrogenase and fumarate reductase, and the fumarate reductase mainly catalyzes the above reaction.

Moreover, the expression "lactate dehydrogenase activity is reduced or inactivated relative to the wild-type microorganism" in Condition (II) means that lactate dehydrogenase activity is significantly reduced or completely inactivated relative to the wild-type microorganism that is used as a starting material for preparation of the genetically modified microorganism according to the invention.

Furthermore, the expression "pyruvate:quinone oxidoreductase activity is reduced or inactivated relative to the wild-type microorganism" in Condition (IV) means that pyruvate:quinone oxidoreductase activity is significantly reduced or completely inactivated relative to the wild-type microorganism used as a starting material for preparation of the genetically modified microorganism according to the invention.

More specifically, Conditions (I), (II), and (IV) mean that, in the metabolic pathway of the microorganism as shown in FIG. 1, the metabolization from succinic acid to fumaric acid or the reverse metabolization thereof (e.g., SdhCAB/FrdDCBA), the metabolization from pyruvic acid to lactic acid (Ldh), and the metabolization from pyruvic acid to acetic acid (PoxB; Pro), respectively, are significantly suppressed or inactivated.

Meanwhile, in microorganisms capable of proliferating under aerobic conditions but incapable of proliferating under reducing conditions (anaerobic conditions), generally, metabolism in the TCA cycle (citric acid cycle) shown in FIG. 1 proceeds clockwise under aerobic conditions, while, on the other hand, metabolism in the TCA cycle proceeds counterclockwise under reducing conditions or anaerobic conditions.

That is, in the case of adopting an embodiment satisfying Condition (I) in the invention, since conversion from succinic acid to fumaric acid is suppressed under aerobic conditions, a larger amount of citric acid, cis-aconitic acid, D-isocitric acid, α-ketoglutaric acid, succinyl CoA, succinic acid, or additional metabolites derived therefrom can efficiently be produced, while, on the other hand, under reducing conditions or anaerobic conditions, a larger amount of oxaloacetic acid, L-malic acid, fumaric acid, or additional metabolites derived therefrom can efficiently be produced. In that case, in the genetically modified microorganism of the invention satisfying Condition (I), the above additional metabolites derived from the above metabolites of the TCA cycle may be biosynthesized via metabolic systems that the corresponding wild-type microorganism inherently possesses, or may even be biosynthesized via new metabolic systems constructed by introduction of a predetermined gene.

Next, in the case of adopting an embodiment satisfying Condition (II) in the invention, since conversion from pyruvic acid to lactic acid is suppressed, the metabolic pathway from pyruvic acid to oxaloacetic acid efficiently proceeds. As a result, according to such an embodiment, the production of oxaloacetic acid, L-malic acid, fumaric acid, or additional metabolites derived therefrom can efficiently be performed.

Furthermore, in the case of adopting an embodiment satisfying Condition (IV) in the invention, since conversion from pyruvic acid to acetic acid is suppressed, similarly to the embodiment satisfying Condition (II), the metabolic pathway from pyruvic acid to oxaloacetic acid efficiently proceeds. As a result, according to such an embodiment, the production of oxaloacetic acid, L-malic acid, fumaric acid, or additional metabolites derived therefrom can efficiently be performed. Therefore, an embodiment satisfying both Conditions (II) and (IV) can preferably be adopted in the invention since the production efficiency of oxaloacetic acid, L-malic acid, fumaric acid, or additional metabolites derived therefrom can be further improved in such an embodiment.

In a specific embodiment, the genetically modified microorganism according to the invention satisfies at least two conditions of Conditions (I), (II), and (IV). In this case, the genetically modified microorganism according to the invention preferably satisfies both of Conditions (I) and (II), both of Conditions (I) and (IV), or Conditions (II) and (IV), and more preferably satisfies all of Conditions (I), (II), and (IV).

The reason for this is explained as follows. In such embodiments, the metabolic pathway from pyruvic acid to the TCA cycle and the metabolism of the TCA cycle efficiently proceed, and therefore, efficient production of oxaloacetic acid, L-malic acid or fumaric acid in the TCA cycle, or a metabolite derived therefrom, or even a downstream metabolite (e.g., citric acid, cis-aconitic acid, D-isocitric acid, α-ketoglutaric acid, succinyl CoA, succinic acid) can be realized. Thus, production of these metabolites or even substances derived therefrom through another metabolization can be efficiently achieved.

More specifically, for example, in the embodiment shown in FIG. 1, a downstream metabolite such as succinic acid or a metabolite derived therefrom (e.g., glutamic acid or a metabolite derived from glutamic acid) can efficiently be produced under aerobic conditions, while, a downstream metabolite such as fumaric acid or a metabolite derived therefrom (for example, aspartic acid or a metabolite derived from aspartic acid) can efficiently be produced under a reducing condition.

Next, Condition (V) will be described.

The genetically modified microorganism according to the invention additionally satisfies the following Condition (V)

in a specific embodiment, although it is not indispensable to satisfy Condition (V) in the invention.

Condition (V): pyruvate formate-lyase activity is reduced or inactivated relative to the wild-type microorganism.

Herein, the expression "pyruvate formate-lyase activity is reduced or inactivated relative to the wild-type microorganism" in Condition (V) means that pyruvate formate-lyase activity is significantly reduced or completely inactivated relative to the wild-type microorganism used as a starting material for preparation of the genetically modified microorganism according to the invention.

In particular, in a case where the genetically modified microorganism according to the invention is a microorganism belonging to gram-negative bacteria, the genetically modified microorganism preferably satisfies Condition (V). The reason for this is as follows. A wild-type microorganism belonging to gram-negative bacteria expresses pyruvate formate-lyase activity that is not usually found in gram-positive bacteria. As described below, the pyruvate formate-lyase activity creates a secondary biosynthetic pathway for synthesis of organic acids such as formic acid and acetic acid from pyruvic acid. That is, when such pyruvate formate-lyase activity is reduced or inactivated, the secondary biosynthetic pathway can be blocked, and thus, the metabolic flux to a target substance is made to be stronger, thereby realizing more efficient production of a target substance.

In the meantime, the succinate dehydrogenase activity or fumarate reductase activity in Condition (I), the lactate dehydrogenase activity in Condition (II), the pyruvate:quinone oxidoreductase activity in Condition (IV), and the pyruvate formate-lyase activity in Condition (V) are respective enzyme activities that can inherently be shown by a wild-type microorganism used as a starting material for preparation of the genetically modified microorganism according to the invention. More specifically, the enzyme activities can be described by the EC numbers, which have been recognized as the international enzyme classification based on systematic taxonomy and categories of reactions according to types of reactions between substrates and enzymes, and the enzyme activities in the respective conditions include the enzyme activities shown in Table 1 below.

TABLE 1

| Conditions | Nomenclature of enzymes | EC numbers | Major possible reactions catalyzed by respective enzymes |
|---|---|---|---|
| (I) | Succinate dehydrogenase Fumarate reductase | 1.3.5.1 | Quinone + Succinate ↔ Hydroquinone + Fumarate |
| | | 1.3.5.4 | Same as above (reverse reaction) |
| | | 1.3.1.6 | Succinate + $NAD^+$ ↔ Fumarate + NADH |
| (II) | Lactate dehydrogenase | 1.1.5.12 | (R)-lactate + Quinone ↔ Pyruvate + Quinol |
| | | 1.1.1.27 | (S)-lactate + $NAD^+$ ↔ Pyruvate + NADH + $H^+$ |
| | | 1.1.1.28 | (R)-lactate + $NAD^+$ ↔ Pyruvate + NADH + $H^+$ |
| | | 1.1.2.4 | (R)-lactate + 2[Fe(III)cytochrome c] ↔ 2[Fe(II)cytochrome c] + $2H^+$ + Pyruvate |
| | | 1.1.2.3 | (S)-lactate + 2[Fe(III) cytochrome c] ↔ [Fe(II)cytochrome c] + $2H^+$ + Pyruvate |
| (IV) | Pyruvate:quinone oxidoreductase (Pyruvate dehydrogenase (quinone)) | 1.2.5.1 | Pyruvate + ubiquinone + $H_2O$ ↔ Acetate + $CO_2$ + ubiquinol |
| (V) | Pyruvate Formate-Lyase (Formate acetyltransferase) | 2.3.1.54 | Acetyl-CoA + Formate ↔ CoA + Pyruvate |

Herein, fulfillment of Conditions (I) and/or (II) and/or (IV) and/or (V) may be realized using various techniques for genetic engineering and molecular biology. For example, with respect to succinate dehydrogenase genes or fumarate reductase genes, lactate dehydrogenase genes, pyruvate: quinone oxidoreductase genes, and pyruvate formate-lyase genes (formate acetyltransferase genes), which are found in microorganisms exemplified in Tables 2 to 10 below, a technique based on gene disruption or mutation introduction that targets the genes on genome, a technique based on antisense inhibition (antisense RNA) on the mRNA expression level, and the like can be applied. Alternatively, a genetically modified microorganism subjected to genetic manipulation to express a peptide or protein inhibiting each of the enzyme activities is also encompassed by the invention. Furthermore, alternatively, in a case where an enzyme protein that can cause each enzyme activity requires an activation process by a predetermined endogenous activator to express the enzyme activity in the microorganism, fulfillment of each condition may be realized by way of inactivation of the endogenous activator to thereby suppress the expression of the enzyme activity.

However, a technique for gene disruption or mutation introduction is preferably employed because such a technique make it possible to relatively simply and more reliably realize reduction or inactivation of the respective enzyme activities in the above conditions. More specifically, any of embodiments (I) to (IV) is preferably adopted:

(I) an embodiment in which an enzyme gene coding region that can cause each enzyme activity has completely or partially been disrupted in the genome (chromosomal DNA) of the genetically modified microorganism to fulfill Conditions (I) and/or (II) and/or (IV) and/or (V);

(II) an embodiment in which a gene expression regulation region (e.g., a promoter region) that exists upstream of an enzyme gene coding region causing each enzyme activity has been completely or partially disrupted in the genome of the genetically modified microorganism to fulfill Conditions (I) and/or (II) and/or (IV) and/or (V);

(III) an embodiment in which a nucleotide mutation inducing one or more amino acid mutations has been introduced into an enzyme gene coding region that can cause each enzyme activity, in the genome of the genetically modified microorganism, to fulfill Conditions (I) and/or (II) and/or (IV) and/or (V), wherein the "one or more amino acid mutations" mean amino acid mutations causing reduction or inactivation of each enzyme activity;

(IV) an embodiment in which an endogenous activator that activates enzyme activity of an enzyme protein causing each enzyme activity has been inactivated based on the methods mentioned in Embodiments (I) to (III) above, to fulfill Conditions (I) and/or (II) and/or (IV) and/or (V).

Additionally, needless to say, Embodiments (I) to (IV) above may be each independently adopted to realize the reduction or inactivation of each enzyme activity defined in each condition. In addition, in order to satisfy one condition, at least two embodiments of Embodiments (I) to (IV) may be adopted particularly within the range that does not cause any inconsistency. For example, in order to satisfy Condition (I), both Embodiments (I) and (II) may be adopted, and, more specifically, both of the coding region and the gene expression regulation region for each gene may be disrupted in the genome of the microorganism. In addition, for example, both of Embodiments (I) and (II) may be adopted in order to satisfy Condition (I), and Embodiment (III) may be adopted in order to satisfy Condition (II).

Herein, the disruption of the gene coding region or the gene expression regulation region (target region) in the genetically modified microorganism can be realized, for example, based on techniques such as a homologous recombination method, a genome-editing technique (CRISPR/CAS system), a transposon method, and a mutation introduction method. Among these techniques, from the viewpoint that the disruption of the target region can comparatively inexpensively and efficiently be achieved, it a homologous recombination method is conveniently employed. Hereinafter, an example of a gene disruption method based on homologous recombination will be described. However, it should be noted that the method for preparing the genetically modified microorganism according to the invention is not limited to the method described below, and any method can be adopted.

[Gene Disruption Method Based on Homologous Recombination]

(1) Determination of Target Region to be Disrupted and Cloning of Same Region

Regarding a number of bacteria such as the genera *Escherichia, Bacillus* and *Clostridium*, and various fungi such as *Saccharomyces cerevisiae* and *Yarrowia lipolytica*, their whole genome sequences have been determined, and also, their nucleotide sequences, and amino acid sequences of proteins encoded by respective genes have already been known.

For example, speaking of *Corynebacterium glutamicum*, which is one of microorganisms that can preferably be used in the invention, whole genome sequences of many strains such as strain ATCC13032, strain R, strain ATCC21831, and strain ATCC14067 have been determined, and also, their nucleotide sequences and the like have already been known. Moreover, whole genome sequences have already been determined for strains of the genus *Corynebacterium* such as *Corynebacterium efficiens* strain YS-314; *Corynebacterium callunae* strain DSM20147; *Corynebacterium ammoniagenes* strain DSM20306; *Corynebacterium marinum* strain DSM44953; *Corynebacterium humireducens* strain NBRC106098 (DSM45392); *Corynebacterium halotolerans* strain YIM70093 (DSM44683); *Corynebacterium deserti* strain GIMN1.010; *Corynebacterium maris* strain DSM45190; and *Corynebacterium doosanense* strain CAU212 (DSM45436), and thus, their nucleotide sequences and the like have already been known. Furthermore, there are also microorganisms of which nucleotide sequences of the respective enzyme genes causing the respective enzyme activities in Conditions (I), (II), (IV), and (V), and amino acid sequences of the enzymes have already been known, although their whole genome sequences have not yet been determined.

Such known nucleotide sequences and amino acid sequences are easily available from various databases such as database (URL: https://www.nebi.nlm.nih.gov/) posted on the Internet by National Center for Biotechnology Information Support Center (NCBI) (8600 Bethesda Rockville Pike, Maryland, USA).

With regard to microorganisms serving as starting materials for preparation of the genetically modified microorganisms according to the invention, Tables 2 to 10 below shows examples of information on genes that may be subjected to disruption or the like to reduce or inactivate the enzyme activities in Conditions (I) and/or (II) and/or (IV) and/or (V), etc. In addition, needless to say, information and the like on microorganisms that may be used in the invention, and the respective genes that may be targeted to reduce or inactivate the respective enzyme activities are not limited to those shown in the following tables.

TABLE 2

| Microorganism (Scientific names) | Gene symbols (homologue gene) | Gene ID | GenBankID (NCBI) Information |
|---|---|---|---|
| *Corynebacterium glutamicum* ATCC13032 (Genome sequence ID: NC_003450.3) | sdhC (Cgl0370) | 1021096 | Coding region: 392705-393478 protein_id: NP_599618.1 |
| | sdhA (Cgl0371) | 1021051 | Coding region: 393495-395516 protein id: NP 599619.1 |
| | sdhB (Cgl0372) | 1021416 | Coding region: 395516-396265 protein id: NP 599620.1 |
| | ldh (Cgl2911) | 1020853 | Coding region: complement (3112447-3113391) protein id: NP 602100.1 |
| | poxB (pqo) (Cgl2610) | 1020557 | Coding region: complement (2776766-2778505) protein id: NP 601811.1 |

TABLE 2-continued

| | | | |
|---|---|---|---|
| *Escherichia coli* str. K-12 substr. MG1655 (Genome sequence ID: NC_000913.3) | sdhC | 945316 | Coding region: 755177..755566 protein_id: NP_415249.1 |
| | sdhD | 945322 | Coding region: 755560..755907 protein_id: NP_415250.1 |
| | sdhA | 945402 | Coding region: 755907..757673 protein_id: NP_415251.1 |
| | sdhB | 945300 | Coding region: 757689..758405 protein_id: NP_415252.1 |
| | ldhA | 946315 | Coding region: complement (1441854..1442843) protein_id: NP_ 415898.1 EC number=1.1.1.28 |
| | dld | 946653 | Coding region: 2222185..2223900 protein_id: NP_416637.1 EC number=1.1.5.12 |
| | lldD | 948121 | Coding region: 3779827..3781017 protein id: NP 418062.1 |
| | poxB | 946132 | Coding region: complement (909331..911049) protein_id: NP_415392.1 |
| | frdD (ECK4147) | 948668 | Coding region: complement (4379007..4379366) product: fumarate reductase membrane protein FrdD protein_id: NP_418575.1 EC number:1.3.5.4 |
| | frdC (ECK4148) | 948680 | Coding region: complement (4379377..4379772) Product: fumarate reductase membrane protein FrdC protein_id: NP_418576.1 EC number=1.3.5.4 |
| | frdB (ECK4149) | 948666 | Coding region: complement (4379783..4380517) Product: fumarate reductase iron-sulfur protein protein_id:NP_418577.1 EC number:1.3.5.4 |
| | frdA (ECK4150) | 948667 | Coding region: complement (4380510..4382318) product: fumarate reductase flavoprotein subunit protein_id: NP_418578.1 EC number:1.3.5.4 |
| | pflB (ECK0894; pfl) | 945514 | Coding region: complement (951272..953554) product: pyruvate formate-lyase protein_id: NP_415423.1 EC number:2.3.1.54 |
| | ybiW (ECK0813; pflF) | 945444 | Coding region: complement (860174..862606) product: putative pyruvate formate lyase protein id: NP_415344.1 |
| | pflD (ECK3942; yijL) | 948454 | Coding region: 4143995..4146292 product: putative formate acetyltransferase 2 protein_id: NP_418386.1 |
| | tdcE (ECK3103; yhaS) | 947623 | Coding region: complement (3260124..3262418) product: 2-ketobutyrate formate-lyase/pyruvate formate-lyase 4 protein_id: YP_026205.1 EC number:2.3.1.54 |
| | pflA (act; ECK0893) | 945517 | Coding region: complement (950340..951080) product: pyruvate formate-lyase activating enzyme protein_id: NP_415422.1 EC number:1.97.1.4 |
| | pflC (ECK3943; yijM) | 948453 | Coding region: 4146258..4147136 product: putative pyruvate formate-lyase 2 activating enzyme PflC protein_id: NP_418387.3 |

TABLE 2-continued

| | | | |
|---|---|---|---|
| *Bacillus subtilis* ATCC 13952 (Genome sequence ID:NZ_CP009748.1) | sdhC | — | complement (2665158..2665766)<br>protein_id: WP_003152571.1 |
| | sdhA | — | complement (2663364..2665124)<br>protein_id: WP_013353100.1 |
| | sdhB | — | complement (2662603..2663361)<br>protein_id: WP_013353099.1 |
| | KS08_RS01490 | — | 282196..283149<br>protein_id: WP_014471413.1<br>L-lactate dehydrogenase |

TABLE 4

| Microorganism (Scientific names) | Gene symbols (homologue gene) | Gene ID | GenBankID (NCBI) Information |
|---|---|---|---|
| *Saccharomyces cerevisiae* S288C | SDH1 | 853709 | Chromosome XI<br>Genome sequence ID: NC_001136.10<br>complement (<169207..>171129)<br>transcript_id: NM_001179714.1<br>protein_id: NP_012774.1<br>Flavoprotein subunit |
| | SDH2 | 850685 | Chromosome XII<br>Genome sequence ID: NC_001144.5<br>complement (<53131..>53931)<br>transcript_id: NM_001181861.1<br>protein_id: NP_013059.1<br>Iron-sulfur protein subunit |
| | SDH3 | 853716 | Chromosome XI<br>Genome sequence ID: NC_001143.9<br><179667..>180263<br>transcript_id:NM_001179707.1<br>protein_id: NP_012781.1<br>Cytochrome b subunit |
| | SDH4 | 851758 | Chromosome IV<br>Genome sequence ID: NC_001136.10<br><817950..>818495<br>transcript_id: NM_001180485.1<br>protein_id: NP_010463.1<br>Membrane anchor subunit |
| | SDH5 | 854083 | Chromosome XV<br>Genome sequence ID: NC_001147.6<br><196507..>196995<br>transcript_id: NM_001183326.1<br>protein_id: NP_014570.1<br>Protein required for flavinylation of Sdh1p (This protein binds to Sdh1p and promotes FAD cofactor attachment, which is necessary for assembly of succinate dehydrogenase (SDH) and expression of activity.) |
| | SDH6 | 851986 | Chromosome IV<br>Genome sequence ID: NC_001136.10<br>complement (1233278..1233517)<br>transcript_id: NM_001184471.3<br>protein_id: NP_076888.3<br>Mitochondrial protein involved in assembly of SDH (involved in maturation of the Sdh2p subunit). |
| | SDH7 | 852123 | Chromosome IV<br>Genome sequence ID: NC_001136.10<br><1470017..>1470418<br>transcript_id: NM_001180819.3<br>protein_id: NP_010799.3<br>Mitochondrial protein involved in assembly of SDH (involved in maturation of the Sdh2p subunit) |
| | SDH8 | 852572 | Chromosome II<br>Genome sequence ID: NC_001134.8<br>complement (<742160..>742576)<br>transcript_id: NM_001178617.1<br>protein_id: NP_009828.2<br>Protein required for assembly of SDH |

TABLE 4-continued

| | | | |
|---|---|---|---|
| | DLD1 | 851380 | Chromosome IV<br>Genome sequence ID:<br>NC_001136.10<br>complement (<145826..>147589)<br>transcript_id: NM_001180234.1<br>protein_id: NP_010107.1<br>Major D-lactate dehydrogenase |
| | DLD2 | 851376 | Chromosome IV<br>Genome sequence ID:<br>NC_001136.10<br>transcript_id: NM_001180238.1<br>protein_id: NP_010103.1<br>Minor d-lactate dehydrogenase |
| | DLD3 | 856638 | Chromosome V<br>Genome sequence ID: NC_001137.3<br><16355..>17845<br>transcript_id: NM_001178886.1<br>protein_id: NP_010843.1<br>Minor D-lactate dehydrogenase |

TABLE 6

| Microorganism (Scientific names) | Gene symbols (homologue gene) | GenBankID (NCBI) information |
|---|---|---|
| *Yarrowia lipolytica* CLIB89 (W29) | SDH1 | Chromosome 1D<br>Genome sequence ID: CP017556.1<br>complement (1423938..1426073)<br>protein_id: AOW03921.1<br>Flavoprotein subunit 2 |
| | SDH2 | Chromosome 1D<br>Genome sequence ID: CP017556.1<br>3025537..3026343<br>protein_id: AOW04521.1<br>Iron-sulfur protein subunit |
| | SDH3 | Chromosome lE<br>Genome sequence ID: CP017557.1<br>3508208..3509167<br>mRNA:join(3508208..3508241,3508686..3509167)<br>protein_id: AOW06147.1 |
| | SDH4 | Chromosome lA<br>Genome sequence ID: CP017553.1<br>complement (1471620..1472117)<br>protein_id: AOW00655.1<br>SDH2P membrane anchor subunit |
| | SDH5 | Chromosome 1F<br>Genome sequence ID: CP017558.1<br>1579326..1579763<br>protein_id: AOW07023.1<br>Flavinator of SDH |
| | DLD1 | Chromosome lE<br>Genome sequence ID: CP017557.1<br>complement (385330..387066)<br>protein id: AOW04885.1 |
| | YALI1_E25400g | Chromosome lE<br>Genome sequence ID: CP017557.1<br>2540045..2541166<br>protein_id: AOW05746.1<br>Putative lactate dehydrogenase cytochrome b |

Furthermore, with respect to a variety of the genus *Corynebacterium* of which whole genome sequences have been specified, information such as GenBlank ID accession numbers for homologous genes of sdhCABD gene, ldh gene, and poxB gene are shown in Tables 7 to 10.

TABLE 7

| Coryneform bacterial species (Scientific names) | Gene symbols (homologue gene) | GenBankID (NCBI) information |
|---|---|---|
| *Corynebacterium efficiens* YS-314 | sdhC | Genome sequence ID: NC_004369.1<br>Coding region: 420459-421232<br>protein_id: WP_011074957.1 |

TABLE 7-continued

| | | |
|---|---|---|
| | sdhA | Genome sequence ID: NC_004369.1<br>Coding region: 421253-423265<br>protein_id: WP_006770371.1 |
| | sdhB | Genome sequence ID: NC_004369.1<br>Coding region: 423265-424014<br>protein_id: WP_006770370.1 |
| | ldh | Genome sequence ID: NC_004369.1<br>Coding region: complement (2936722-2937675)<br>protein_id: WP_035109376.1 |
| | poxB | Unknown |
| *Corynebacterium callunae* DSM20147 | sdhC | Genome sequence ID: CP004354.1<br>Coding region: 374848-375621<br>protein_id: AGG65781.1 |
| | sdhA | Genome sequence ID: CP004354.1<br>Coding region: 375641-377653<br>protein_id: AGG65782.1 |
| | sdhB | Genome sequence ID: CP004354.1<br>Coding region: 377653-378402<br>protein_id: AGG65783.1 |
| | ldh | Genome sequence ID: CP004354.1<br>Coding region: 2672590-2673537<br>protein_id: AGG67879.1 |
| | poxB | Genome sequence ID: CP004354.1<br>Coding region: complement (2370666-2372405)<br>protein_id: AGG67621.1 |
| *Corynebacterium ammoniagenes* DSM20306 | sdhC | Genome sequence ID: CP009244.1<br>Coding region: 370172-370927<br>protein_id: APT81721.1 |
| | sdhA | Genome sequence ID: CP009244.1<br>Coding region: 370962-37297<br>protein_id: APT81722.1 |
| | sdhB | Genome sequence ID: CP009244.1<br>Coding region: 372977-373726<br>protein_id: APT81723.1 |
| | ldh | Genome sequence ID: CP009244.1<br>Coding region: complement (2614468-2615415)<br>protein_id: APT83593.1 |
| | poxB | Genome sequence ID: CP009244.1<br>Coding region: complement (2383050-2384801)<br>protein_id: APT83404.1 |

TABLE 8

| Coryneform bacterial species (Scientific names) | Gene symbols (homologue gene) | GenBankID (NCBI) information |
|---|---|---|
| *Corynebacterium marinum* DSM 44953 | sdhC | Genome sequence ID: NZ_CP007790.1<br>Coding region: 279105-279860<br>protein_id: WP_042620633.1 |
| | sdhA | Genome sequence ID: NZ_CP007790.1<br>Coding region: 279887-281896<br>protein_id: WP_042620634.1 |
| | sdhB | Genome sequence ID: NZ_CP007790.1<br>Coding region: 281896-282645<br>protein id: WP_042620635.1 |
| | ldh | Genome sequence ID: NZ_CP007790.1<br>Coding region: complement (2470158-2471123)<br>WP_042622762.1 |
| | poxB | Genome sequence ID: NZ_CP007790.1<br>Coding region: complement (2227741-2229486)<br>protein_id: WP_042622095.1 |
| *Corynebacterium humireducens* NBRC 106098 (DSM 45392) | sdhC | Genome sequence ID: CP005286.1<br>Coding region: 269560-270315<br>protein_id: AJE32111.1 |
| | sdhA | Genome sequence ID: CP005286.1<br>Coding region: 270342-272351<br>protein_id: AJE32112.1 |
| | sdhB | Genome sequence ID: CP005286.1<br>Coding region: 272351-273100<br>protein_id: AJE32113.1 |

TABLE 8-continued

| | | |
|---|---|---|
| | ldh | Genome sequence ID: CP005286.1<br>Coding region: complement (2555308-2556261)<br>protein_id: AJE34285.1 |
| | poxB | Genome sequence ID: CP005286.1<br>Coding region: complement (2270826-2272571)<br>protein_id: AJE34046.1 |
| *Corynebacterium halotolerans* YIM 70093 (DSM 44683) | sdhC | Genome sequence ID: NC_020302.1<br>Coding region: 413293-414048<br>protein_id: WP_015399818.1 |
| | sdhA | Genome sequence ID: NC_020302.1<br>Coding region: 414079-416088<br>protein_id: WP_015399819.1 |
| | sdhB | Genome sequence ID: NC_020302.1<br>Coding region: 416088-416837<br>protein_id: WP_015399820.1 |
| | ldh | Genome sequence ID: NC_020302.1<br>Coding region: complement (2953144-2954118)<br>protein_id: WP_015402062.1 |
| | poxB | Genome sequence ID: NC_020302.1<br>Coding region: complement (2649819-2651555)<br>protein_id: WP_015401811.1 |

TABLE 9

| Coryneform bacterial species (Scientific names) | Gene symbols (homologue gene) | GenBankID (NCBI) information |
|---|---|---|
| *Corynebacterium deserti* GIMN1.010 | sdhC | Genome sequence ID: NZ_CP009220.1<br>Coding region: 422535-423308<br>protein_id: WP_053544030.1 |
| | sdhA | Genome sequence ID: NZ_CP009220.1<br>Coding region: 423330-425354<br>protein_id: WP 053544031.1 |
| | sdhB | Genome sequence ID: NZ_CP009220.1<br>Coding region: 425354-426103<br>protein_id: WP_053544032.1 |
| | ldh | Genome sequence ID: NZ_CP009220.1<br>Coding region: complement (2773439-2774383)<br>protein_id: WP_053545854.1 |
| | poxB | Genome sequence ID: NZ_CP009220.1<br>Coding region: complement (2464577-2466316)<br>protein_id: WP_053545632.1 |
| *Corynebacterium doosanense* CAU 212 (DSM 45436) | sdhC | Genome sequence ID: NZ_CP006764.1<br>Coding region: 406322-407077<br>protein_id: WP_026159285.1 |
| | sdhA | Genome sequence ID: NZ_CP006764.1<br>Coding region: 407089-409191<br>protein_id: WP_018021407.1 |
| | sdhB | Genome sequence ID: NZ_CP006764.1<br>Coding region: 409191-409940<br>protein_id: WP_018021406.1 |
| | ldh | Genome sequence ID: NZ_CP006764.1<br>Coding region: 1783629-1784582<br>protein_id: WP_018020959.1 |
| | poxB | Genome sequence ID: NZ_CP006764.1<br>Coding region: complement (2289478-2291241)<br>protein_id: WP_018022699.1 |
| *Arthrobacter* sp. PGP41 | sdhB (Iron-sulfur subunit) | Genome sequence ID: NZ_CP026514.1<br>Coding region: complement (1210020-1210802)<br>protein_id: WP_104997174.1 |
| | sdhA (Flavoprotein subunit) | Genome sequence ID: NZ_CP026514.1<br>Coding region: complement (1210805-1212604)<br>protein_id: WP_104997175.1 |
| | sdhD (Subunit D) | Genome sequence ID: NZ_CP026514.1<br>Coding region: complement (1212713-1213204)<br>protein_id: WP_104997176.1 |

TABLE 9-continued

| | | |
|---|---|---|
| | sdhC (Cytochrome b556 subunit) | Genome sequence ID: NZ_CP026514.1<br>Coding region: complement (1213208-1213588)<br>protein_id: WP_104997177.1 |
| | ldh | Genome sequence ID: NZ_CP026514.1<br>Coding region: 4105995-4106942<br>protein_id: WP_104999408.1 |
| | poxB | Unknown |

TABLE 10

| Coryneform bacterial species (Scientific names) | Gene symbols (homologue gene) | GenBankID (NCBI) information |
|---|---|---|
| *Micrococcus luteus* NCTC 2665 | sdhB (Iron-sulfur subunit) | Genome sequence ID: NC_012803.1<br>Coding region: complement 4528020-528811)<br>protein_id: WP_010079347.1 |
| | sdhA (Flavoprotein subunit) | Genome sequence ID: NC_012803.1<br>Coding region: complement (528811-530598)<br>protein_id: WP_010079346.1 |
| | sdhD (Subunit D) | Genome sequence ID: NC_012803.1<br>Coding region: complement (530676-531155)<br>protein_id: WP_010079345.1 |
| | sdhC (Cytochrome b556 subunit) | Genome sequence ID: NC_012803.1<br>Coding region: complement (531159-531563)<br>protein_id: WP_010079344.1 |
| | ldh | Genome sequence ID: NC_012803.1<br>Coding region: 2304603-2305589<br>protein_id: WP_010079965.1 |
| | poxB | Genome sequence ID: NC_012803.1<br>Coding region: complement (293132-294847)<br>protein_id: WP_010079539.1 |

As for the respective enzyme genes possessed by bacteria, the succinate dehydrogenase activity, the fumarate reductase activity, the lactate dehydrogenase activity, the pyruvate: quinone oxidoreductase activity, and the pyruvate formate-lyase activity are enzyme activities shown by succinate dehydrogenase (Sdh), fumarate reductase (Frd), lactate dehydrogenase (Ldh), pyruvate:quinone oxidoreductase (Pox or Pqo), and pyruvate formate-lyase (Pfl) which are found in wild-type strains, respectively. The proteins of these enzymes can be encoded by genes or the like represented as sdhCAB (or sdhCABD depending on bacterial species); ldhA, dld, lldD, etc. (gene coding for an enzyme protein showing lactate dehydrogenase activity), poxfl (pqo), and pflABCD (see Tables 2 to 10).

In addition, in bacteria, succinate dehydrogenase (Sdh), is a complex composed of three subunit proteins of a transmembrane protein (subunit C) encoded by sdhC gene, a flavoprotein subunit (subunit A) encoded by sdhA gene, and Fe—S protein (subunit B) encoded by sdhfl gene, and, in some cases, SdhD (subunit D). In cases of prokaryotes, the genes each encoding these subunits form an operon in the bacterial genomes (for example, see FIG. 2B). Additionally, the fumarate reductase (Frd) is a complex composed of subunits D, C, B, and A in bacteria such as *Escherichia coli*, and is encoded by frdDCBA gene (operon). Furthermore, the pyruvate formate-lyase (Pfl) is a complex composed of the subunits A, B, C, and D in bacteria such as *Escherichia coli*, and is encoded by pflABCD gene (operon).

Microorganisms for which nucleotide sequences and protein sequences of coding regions of the respective enzyme genes in Conditions (I), (II), (IV), and (V) as described above, as well as peripheral regions thereof have already been known would conveniently be employed. This is because genome regions to be disrupted can easily be specified by reference to the known sequences. However, needless to say, microorganisms that can be used as starting materials for preparation of genetically modified microorganism according to the invention are not limited to the microorganisms for which genomic nucleotide sequences or the like have already been known as described above, and even any microorganisms for which the enzyme protein coding regions or peripheral regions thereto are unknown can also be employed.

In such cases where microorganisms for which enzyme protein coding regions or peripheral regions thereof have not been known are employed, for example, the coding regions for enzyme genes are appropriately cloned by any types of genetic engineering techniques, and the nucleotide sequences thereof may be determined as needed, thus identifying and cloning regions to be disrupted. For example, when alignment analysis is carried out for known amino acid sequences of the homologue enzyme proteins (Tables 2 to 10), a plurality of certain amino acid conservative regions are found. Therefore, degenerate primers can be designed within the amino acid conservative regions each found at the N-terminal side and the C-terminal side of the enzyme proteins, the degenerate PCR method may be performed using as a template the genomic DNA of a cloning target of microorganism, and using a pair of the above degenerate primers, thus amplifying and cloning parts of the coding regions for the target enzyme genes. Then, nucleotide sequences of the partial coding regions may be appropriately determined, and the cloned partial coding regions may be targeted for gene disruption based on the method for preparing a gene-disrupted strain described below, or the like, thereby preparing a genetically modified microorganism according to the invention satisfying Conditions (I), (II), (IV), and (V). In the meantime, when it is required to prepare a genetically modified microorganism in which full-length coding regions for the target enzyme genes, or entire regions of gene expression regulation regions present peripheral to the enzyme genes have been disrupted, pairs of primers may appropriately be designed to the opposite direction within the partial internal coding regions of the enzyme genes, for which nucleotide sequences have been determined in the above way, and then, the full-length coding regions for the target enzyme genes, or the peripheral regions thereof may be cloned using technique such as the inverse PCR method, and also, nucleotide sequences of these regions may be determined. Such a cloning technique based on PCR is convenient since the genome regions to be disrupted can easily be cloned. However, as for alternative techniques, a gene library of a target microorganism may be prepared, suitable probes may be designed, and then, the enzyme genes and the peripheral regions thereof, serving as targets for disruption, may be cloned by various hybridization methods, and also, nucleotide sequences thereof may be determined. Furthermore, with regard to any microbial species for which any homologous gene sequences are unavailable, in accordance with conventional methods, the target enzymes may be identified based on combination of protein purification techniques and enzyme activity measurement techniques. Then, for example, peptide sequences thereof may be partially determined, and, subsequently, the target enzyme genes may be cloned by the various genetic engineering techniques.

(2) Preparation of Plasmid Vector for Gene Disruption, and Disruption of Gene (Coding Region/Expression Regulation Region Etc.) by Homologous Recombination Next, with regard to disruption of the enzyme genes in Conditions (I), (II), (IV) and (V), a method for preparing a gene-disrupted strain based on a homologous recombination technique will be described.

At first, it is required that a plasmid vector for gene disruption that causes homologous recombination with respect to a region to be disrupted in the genome is prepared.

As an example of such a plasmid vector for gene disruption, a gene disrupting plasmid vector obtained by inserting a drug-resistant gene, e.g., a kanamycin-resistance gene, into the inside of the region to be disrupted in a plasmid vector that has been obtained by cloning the region to be disrupted in the microorganism genome, can be mentioned. In such a gene disrupting plasmid vector, regions to each homologous to the region to be disrupted in the microorganism genome exist at both sides of the drug-resistant gene. Therefore, since homologous recombination occurs between the microorganism genome and the gene disrupting plasmid in a manner that the drug-resistant gene is inserted into the region to be disrupted in the microorganism genome, this makes it possible to realize disruption of a target enzyme gene. In addition, by way of adding a drug relating to the drug-resistant gene to the culture media, a gene-disrupted strain can also be efficiently selected.

As another example of the plasmid vector for gene disruption, a plasmid vector including a fragment in which regions located at both sides of the part to be disrupted in the microorganism genome (i.e., regions each located 5' upstream and 3' downstream of the part to be removed from the genome) are linked to one another in tandem, can also be employed. Such a plasmid for disruption can be obtained, for example, as follows: regions present 5' upstream and 3' downstream of the disruption-target enzyme gene are each amplified based on the PCR method, and the amplified fragments are then inserted into a predetermined site, such as a multiple cloning site, of a plasmid vector in a manner that the amplified fragments are linked to one another in tandem. Alternatively, the whole region from the 5' upstream region to the 3' downstream region around the enzyme gene to be disrupted may be amplified based on the PCR method; the amplified product may be cloned with a variety of plasmid vectors; primers may subsequently be designed to the opposite direction inside the cloned region; and a plasmid vector for gene disruption into which a deletion mutation of the enzyme gene is introduced may be prepared based on the inverse PCR method with the primers.

In the plasmid for gene disruption, the sequence length of a region homologous to a microorganism genome sequence that is a target for gene disruption is not limited as long as it can cause the homologous recombination. However, the sequence length may generally be about 500 bp or more, and preferably be around 1000 bp. Moreover, for the plasmid for gene disruption, a plasmid having a replication origin of *E. coli* is convenient since such a plasmid makes it possible to plasmid construction using *E. coli* for cloning, thus simplifying the construction operations. Furthermore, the plasmid for gene disruption preferably have no replication origin causing its autonomous replication in a microorganism that is employed as a target for gene disruption. If any replication origins of the microorganism exist in the plasmid for gene disruption, it is recommended that the replication origins are removed therefrom based on restriction enzyme treatments or the like, followed by introduction thereof into a coryneform bacterium. Additionally, for the plasmid for gene disruption, a combination of a drug-resistant gene enabling drug-based selection, and a lethal gene enabling positive selection, e.g., SacB gene which can produce a toxin inhibiting the growth of Gram-negative bacteria in the presence of sucrose, may be used. When such a plasmid for gene disruption is employed, strains that have undergone the homologous recombination can be isolated based on the selection using a drug, and then, gene-disrupted strains from which the vector portion has been eliminated through second homologous recombination can be isolated by way of carrying out selection based on cultivation in a culture medium containing sucrose, thereby realizing efficient acquisition of gene-disrupted strains.

For introduction of the plasmid vector for gene disruption into microorganisms, any transformation methods that have been established according to types of microorganisms may be employed, although there are no particular limitations. For example, as for coryneform bacteria, which are preferably adopted in the invention, the introduction would be performed conveniently using the electroporation method (e.g., the technique described in Van der Rest et al. Appl. Microbiol Biotechnol 52, pp 541-545, 1999). This is because the electroporation method enables efficient introduction of nucleic acids into cells of coryneform bacteria.

In addition, confirmation of disruption of the target regions in the genome of the genetically modified microorganism can be carried out based on the PCR method, the Southern hybridization method, various enzyme activity measurement methods, and the like.

By using the aforementioned gene disruption techniques, a genetically modified microorganism having reduced or inactivated enzyme activity in Conditions (I) and/or (II) and/or (IV) and/or (V) can be comparatively easily prepared.

[Condition (III)]

The genetically modified microorganism according to the invention may further satisfy Condition (III): "the genetically modified microorganism has modified phosphoenolpyruvate carboxylase activity showing resistance to feedback inhibition by aspartic acid in wild-type phosphoenolpyruvate carboxylase activity, or exogenous phosphoenolpyruvate carboxylase activity having higher resistance to feedback inhibition by aspartic acid than that of the wild-type phosphoenolpyruvate carboxylase activity shown by the wild-type microorganism."

The meaning of "resistance to feedback inhibition by aspartic acid in wild-type phosphoenolpyruvate carboxylase activity" in Condition (III) is described as follows.

At first, in the invention, specifically, the "phosphoenolpyruvate carboxylase activity" refers to enzyme activity that catalyzes the reaction defined in EC4.1.1.31, and is enzyme activity exerted by phosphoenolpyruvate carboxylases (PEPCs), which are widely possessed by a number of different plants and microorganisms. The metabolic reaction catalyzed by PEPCs is shown below.

[Chem. 1]

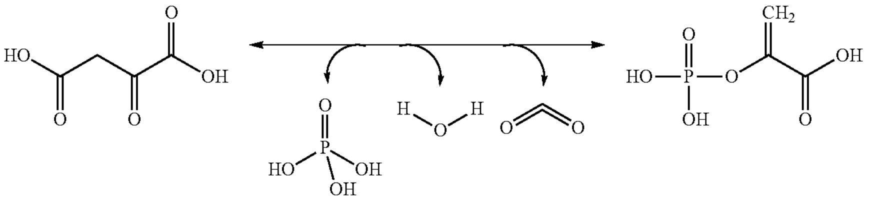

Oxaloacetate + orthophosphoric acid ⟺ $H_2O$ + phosphoenolpyruvate + $CO_2$

In the meantime, it has been known that a wild-type phosphoenolpyruvate carboxylase is allosterically affected by a metabolite such as aspartic acid, malic acid, or α-ketoglutaric acid (2-oxoglutaric acid), and thus the enzyme activity is inhibited. Such a inhibition of the enzyme activity is called "feedback inhibition" (Non-Patent Documents 2 to 4). That is, the "modified phosphoenolpyruvate carboxylase activity" in the invention is defined by an enzymatic property in which the feedback inhibition by aspartic acid in the enzyme activity is significantly reduced relative to the corresponding wild-type microorganism and the wild-type phosphoenolpyruvate carboxylase possessed by the microorganism, while the genetically modified microorganism according to the invention exhibits phosphoenolpyruvate carboxylase activity.

Next, the meaning of the term "exogenous phosphoenolpyruvate carboxylase activity having higher resistance to feedback inhibition by aspartic acid than that of the wild-type phosphoenolpyruvate carboxylase activity shown by the wild-type microorganism" is explained as follows.

That is, the above-described term means exogenous phosphoenolpyruvate carboxylase activity having higher resistance to feedback inhibition by aspartic acid, relative to "resistance to feedback inhibition by aspartic acid" exhibited by a wild-type microorganism that corresponds to the spices to which the genetically modified microorganism according to the invention belongs, or a wild-type phosphoenolpyruvate carboxylase possessed by the wild-type microorganism used as a starting material for preparation of the genetically modified microorganism according to the invention. Specifically, such exogenous phosphoenolpyruvate carboxylase activity may be produced by a heterologous phosphoenolpyruvate carboxylase of a "strain lineages or organism species different from the corresponding wild-type host microorganism." In this case, the "organism species different from the wild-type host microorganism" include microorganisms (e.g., fungi, prokaryotes such as archaea and bacteria), and various organism species of plants, animals such as mammals, and the like. Furthermore, realization of the "exogenous phosphoenolpyruvate carboxylase activity" in the genetically modified microorganism according to the invention can be realized more specifically by introduction of a nucleic acid coding for a PEPC gene isolated from the "strain lineage or organism species different from the wild-type host microorganisms."

Additionally, for example, based on the measurement methods described in Non-Patent Documents 2 to 4, the measurement method described in Yoshinaga, T. Izui, K and Katsuki, H J. Biochem, 68, 747-750 (1970), or the like, it can be formed that the "modified phosphoenolpyruvate carboxylase (activity) shows resistance to feedback inhibition by aspartic acid in wild-type phosphoenolpyruvate carboxylase activity", and that the "exogenous phosphoenolpyruvate carboxylase (activity) shows higher resistance to feedback inhibition by aspartic acid than that of the wild-type phosphoenolpyruvate carboxylase activity shown by the wild-type microorganism."

In addition, "phosphoenolpyruvate carboxylase" would be represented as "PEPC" or "ppc" somewhere in the present specification.

More particularly, fulfillment of Condition (III) can be realized in the manner described below in the genetically modified microorganism according to the invention, although there are no particular limitations. That is, by way of introducing amino acid mutations into protein sequences of wild-type phosphoenolpyruvate carboxylases of various species of microorganisms based on genetic engineering techniques, a gene coding for a mutant-type enzyme acquiring "resistance to feedback inhibition by aspartic acid in the wild-type phosphoenolpyruvate carboxylase activity" while retaining the "phosphoenolpyruvate carboxylase activity" may artificially be produced. For example, any base substitution techniques such as the random mutagenesis based on the error-prone PCR, and the site specific mutagenesis based on PCR using mutagenic primers may be employed therefor. Alternatively, a more advantageous mutant-type PEPC may be produced by applying a molecular evolution technique such as DNA shuffling to DNAs coding for multiple types of wild-type PEPCs.

By way of introducing a nucleic acid coding for a mutant-type PEPC obtained in the above way into a species of microorganism, a genetically modified microorganism satisfying (III) can be prepared. More specifically, the nucleic acid coding for the mutant-type PEPC may be introduce into the species of microorganism in a form that makes it possible to express the mutant-type PEPC. In the related art, a large number of microbial species including coryneform bacteria, gene expression systems suitable for the respective microbial species have already been established. With respect to microorganisms for which any techniques according to the known gene expression systems have been available, such known techniques may be employed for introduction of the mutant-type PEPC into the microorganisms. However, needless to say, any gene manipulation techniques or gene expression systems may uniquely be developed, and such techniques may be employed for introduction of the mutant-type PEPC into microorganisms.

In the genetically modified microorganism according to the invention, the mutant-type PEPC satisfying (III) is preferably a mutant-type enzyme obtained by introducing a predetermined mutation into a bacteria-derived wild-type PEPC, although it is not particularly limited. Furthermore, such a mutant-type PEPC is a mutant-type enzyme obtained by introducing a predetermined mutation into a wild-type PEPC derived preferably from a coryneform bacterium, more preferably from a bacterium of the genus *Corynebacterium.*

In Table 11 below, examples of bacteria-derived PEPCs that may preferably be employed in the invention are mentioned.

TABLE 11

| Source (bacterial species) | GenBankID (NCBI) information | SEQ ID Nos: (Protein sequence) |
|---|---|---|
| *Corynebacterium glutamicum* ATCC13032 | GeneID: 101955<br>Genome sequence ID: NC_003450.3<br>Coding region: complement (1677384-1680143)<br>Gene symbol: Cgl1585<br>protein_id: NP_600799.1 | 2 |
| *Corynebacterium efficiens* YS-314 | Genome sequence ID: NC_004369.1<br>Coding region: complement (1792342-1795101)<br>locus_tag: CE_RS08485<br>protein_id: WP_006767704.1 | 3 |
| *Corynebacterium callunae* DSM20147 | Genome sequence ID: CP004354<br>Coding region: complement (11594895-1597654)<br>protein_id: AGG66941.1 | 4 |
| *Corynebacterium ammoniagenes* DSM 20306 | Genome sequence ID: CP009244.1<br>Coding region: complement (486124-488886)<br>protein_id: APT81814.1 | 5 |
| *Corynebacterium marinum* DSM 44953 | Genome sequence ID: NZ_CP007790.1<br>Coding region: complement (1359285-1362056)<br>protein_id: WP_042621481.1 | 6 |
| *Corynebacterium humireducens* NBRC 106098 = DSM 45392 | Genome sequence ID: CP005286.1<br>Coding region: complement (1428883-1431654)<br>protein_id: AJE33253.1 | 7 |
| *Corynebacterium* halotolerans YIM 70093 = DSM 44683 | Genome sequence ID: NC_020302.1<br>Coding region: complement (1664275-1667040)<br>protein_id: WP_015400953.1 | 8 |
| *Corynebacterium deserti* GIMN1.010 | Genome sequence ID: NZ_CP009220.1<br>Coding region: complement (1613811-1616594)<br>protein_id: WP_082353424.1 | 9 |
| *Corynebacterium doosanense* CAU 212 = DSM 45436 | Genome sequence ID: NZ_CP006764.1<br>Coding region: complement (263722-266466)<br>protein_id: WP_018021559.1 | 10 |
| *Corynebacterium pollutisoli* VDS | Genome sequence ID: FXAR01000006.1<br>Coding region: complement (149213-151984)<br>protein_id: SMG31000.1 | 11 |
| *Arthrobacter* sp. PGP41 | Genome sequence ID: NZ_CP026514.1<br>Coding region: 621955-624777<br>protein_id: WP_104996751.1 | 12 |
| *Escherichia coli* str. K-12 substr. DH10B | Genome sequence ID: NC_010473.1<br>Coding region: complement (4248167-4250818)<br>protein_id: WP_001005586.1 | 13 |

More specifically, as examples of specific structures of the mutant-type PEPC satisfying Condition (III), the following embodiments (i) and (ii) may be considered.

(i) a mutant-type PEPC having deletion, substitution or addition of one or more amino acids in an amino acid sequence of a wild-type PEPC. In this case, the range of “one or more” may be, e.g., from 1 to 100, from 1 to 50, or from 1 to 30, preferably at least 2 or more, or from 2 to 20, more preferably from 2 to 10, still more preferably from 2 to 5, and particularly preferably from 2 to 4, or from 2 to 3, for example, 2.

(ii) a chimeric PEPC including a combination of parts of amino acid sequences of two or more wild-type PEPCs.

Into the genetically modified microorganisms according to some embodiments, nucleic acids coding for bacteria-derived mutant-type phosphoenolpyruvate carboxylases have been introduced in forms capable of expressing the mutant-type phosphoenolpyruvate carboxylases, and the mutant-type phosphoenolpyruvate carboxylases have at least one amino acid mutation causing the genetically modified microorganisms to satisfy Condition (III). In this case, the mutant-type phosphoenolpyruvate carboxylases are preferably mutant-type PEPCs derived from coryneform bacteria, the genus *Corynebacterium*, or the genus *Escherichia*, more preferably mutant-type PEPCs derived from the genus *Corynebacterium*, and particularly preferably mutant-type PEPCs derived from *Corynebacterium glutamicum.*

Furthermore, in specific embodiments, the at least one amino acid mutation in the mutant-type phosphoenolpyruvate carboxylases includes at least one selected from the group consisting of amino acid substitutions shown in the following (a) to (f): based on the amino acid sequence set forth in SEQ ID NO: 2, (a) an amino acid substitution of an amino acid corresponding to the 299th aspartic acid with a predetermined amino acid, wherein the substituted amino acid is not aspartic acid, and the amino acid substitution is preferably an amino acid substitution with alanine, asparagine, glycine, or serine;

(b) an amino acid substitution of an amino acid corresponding to the 653rd lysine with a predetermined amino acid, wherein the substituted amino acid is not lysine, and the amino acid substitution is preferably an amino acid substitution with alanine, asparagine, or serine;

(c) an amino acid substitution of an amino acid corresponding to the 813th lysine with a predetermined amino acid, wherein the substituted amino acid is not lysine, and the amino acid substitution is preferably an amino acid substitution with alanine, asparagine, glycine, or serine;

(d) an amino acid substitution of an amino acid corresponding to the 869th serine with a predetermined amino acid, wherein the substituted amino acid is not serine, and the amino acid substitution is preferably an amino acid substitution with alanine, asparagine, or glycine;

(e) an amino acid substitution of an amino acid corresponding to the 873rd arginine with a predetermined amino acid, wherein the substituted amino acid is not arginine, and the amino acid substitution is preferably an amino acid substitution with alanine, asparagine, glycine, or serine; and (f) an amino acid substitution of an amino acid corresponding to the 917th asparagine with a predetermined amino acid, wherein the substituted amino acid is not asparagine, and the amino acid substitution is preferably an amino acid substitution with alanine, phenylalanine, glycine, or serine, wherein the amino acid before substitution and the substituted amino acid are different from each other in (a) to (f) above.

That is to say, the purpose of the amino acids shown in (a) to (f) above is identification of amino acid substitution sites in the PEPC amino acid sequence that serves as a target for mutagenesis on the basis of amino acids included in the amino acid sequence set forth in SEQ ID NO: 2. In other words, more specifically, the "amino acids corresponding to" in (a) to (f) above refer to amino acids that are aligned one-to-one with the amino acids of SEQ ID NO: 2 shown in (a) to (g) above, when the one-to-one alignment (pairwise alignment) is performed on the basis of the identity of the PEPC amino acid sequence (i.e., a target for mutagenesis) to the amino acid sequence shown in SEQ ID NO: 2, using a technique such as ClustalW or ClustalX (Bioinformatics, Volume 23, Issue 21, 1 Nov. 2007, pp 2947-2948).

FIGS. 3A and 3B shows an example of identification of amino acids to be substituted in (a) to (f) above with respect to wild-type PEPC protein sequences (SEQ ID NOs: 3 to 13), from other 11 species of the genus *Corynebacterium* shown in Table 11, by way of performing the multiple alignment analysis for the protein sequences, based on ClustalW, against the wild-type PEPC amino acid sequence (SEQ ID NO: 2) derived from *Corynebacterium glutamicum* strain ATCC13032.

As shown in FIG. 3A, the "amino acid corresponding to the 299th aspartic acid" in (a) above is aspartic acid (d) in each of the nine types of wild-type PEPCs belonging to the genus *Corynebacterium*, is threonine (T) in the wild-type PEPC of *Arthrobacter globiformis* strain NBRC12137, which is a species of coryneform bacteria, and is glutamic acid (E) in the wild-type PEPC of *Escherichia coli* strain K-12. Moreover, as shown in FIG. 3B, with regard to the nine types of wild-type PEPCs belonging to the genus *Corynebacterium*, the "amino acid corresponding to the 653rd lysine" in (b) above is arginine (R) in *C. ammoniagenes*, and is histidine (H) in *C. doosanense*, while the amino acid is identical to lysine (K) of the base sequence, in each of the other bacterial species. Furthermore, as shown in FIG. 3C, the "amino acid corresponding to the 813th lysine" in (c) above is identical to lysine (K) of the base sequence, in each of all the bacterial species. Furthermore, as shown in FIG. 3C, the "amino acid corresponding to the 869th serine" in (d) above is identical to serine (S) of the base sequence, in each of all the bacterial species. Furthermore, as shown in FIG. 3C, the "amino acid corresponding to the 873rd arginine" in (e) above is identical to arginine (R) of the base sequence, in each of all the bacterial species. Furthermore, as shown in FIG. 3C, the "amino acid corresponding to the 917th asparagine" in (f) above is "threonine" in *C. ammoniagenes*, is valine (V) in *C. doosanense*, and is identical to asparagine (N) of the base sequence, in each of the other bacterial species.

In addition, for example, "the 299th aspartic acid" may be described as "D299" using a single character code for amino acids, and "the amino acid substitution of the 299th aspartic acid with asparagine" may be described as "D299N." Other amino acids and amino acid substitutions may be described in the same manner.

In a more preferred embodiment, the at least one amino acid mutation in the mutant-type phosphoenolpyruvate carboxylase includes at least one selected from the group consisting of amino acid substitutions shown in the following (g) to (l): based on the amino acid sequence set forth in SEQ ID NO: 2, (g) an amino acid substitution of an amino acid corresponding to the 299th aspartic acid with asparagine;

(h) an amino acid substitution of an amino acid corresponding to the 653rd lysine with serine;

(i) an amino acid substitution of an amino acid corresponding to the 813th lysine with a predetermined amino acid, wherein the substituted amino acid is not lysine, and the amino acid substitution is preferably an amino acid substitution with glycine or serine;

(j) an amino acid substitution of an amino acid corresponding to the 869th serine with glycine;

(k) an amino acid substitution of an amino acid corresponding to the 873rd arginine with glycine; and (l) an amino acid substitution of an amino acid corresponding to the 917th asparagine with a predetermined amino acid, wherein the substituted amino acid is not asparagine and the amino acid substitution is preferably an amino acid substitution with alanine, phenylalanine, glycine, or serine.

In a still more preferred embodiment, the at least one amino acid mutation in the mutant-type phosphoenolpyruvate carboxylase includes the amino acid substitution shown in (g) above, and at least one of the amino acid substitutions shown in (h) to (l) above.

Furthermore, in another preferred embodiment, the at least one amino acid mutation in the mutant-type phosphoenolpyruvate carboxylase includes the amino acid substitution shown in (g) above, and at least one of the amino acid substitutions shown in (i) to (l) above.

In addition, in a particularly preferred embodiment, the at least one amino acid mutation in the mutant-type phosphoenolpyruvate carboxylase includes the amino acid substitution shown in (g) above, and the amino acid substitution shown in (i) or (l) above.

Furthermore, in another embodiment, the mutant-type phosphoenolpyruvate carboxylase may be a mutant-type PEPC having an amino acid sequence set forth in any one of the following (A) to (C):

(A) an amino acid sequence obtained by introducing at least one selected from the group consisting of the amino acid substitutions shown in the above (a) to (l) into the amino acid sequence shown in any one of SEQ ID NOs: 2 to 13 (preferably SEQ ID NOs: 2 to 12, more preferably SEQ ID NOs: 2 to 11), wherein the amino acid before substitution and the substituted amino acid are different from each other;

(B) an amino acid sequence having deletion, substitution, and/or addition of one or more amino acids in the amino acid sequence defined in (A) above, wherein the at least one amino acid substitution has been maintained; and (C) an amino acid sequence having a sequence identity of at least 60% to the amino acid sequence defined in (A) above, wherein the at least one amino acid substitution has been maintained.

Furthermore, in still another embodiment, the mutant-type phosphoenolpyruvate carboxylase may be a mutant-type PEPC having an amino acid sequence shown in any one of the following (D) to (F):

(D) an amino acid sequence obtained by introducing the amino acid substitution shown in (g) above, and at least one of the amino acid substitutions shown in (h) to (l) above into the amino acid sequence set forth in any one of SEQ ID NOs: 2 to 13 (preferably SEQ ID NOs: 2 to 12, more preferably SEQ ID NOs: 2 to 11), wherein the amino acid before substitution and the substituted amino acid are different from each other;

(E) an amino acid sequence having deletion, substitution, and/or addition of one or more amino acids in the amino acid sequence defined in (D) above, wherein the above amino acid substitutions have been maintained; and (F) an amino acid sequence having a sequence identity of at least 60% to the amino acid sequence defined in (D) above, wherein the above amino acid substitutions have been maintained.

Furthermore, in still another embodiment, the mutant-type phosphoenolpyruvate carboxylase may be a mutant-type PEPC having an amino acid sequence shown in any one of the following (G) to (I):

(G) an amino acid sequence obtained by introducing the amino acid substitution shown in (g) above, and at least one of the amino acid substitutions shown in (i) to (l) above into the amino acid sequence set forth in any one of SEQ ID NOs: 2 to 13 (preferably SEQ ID NOs: 2 to 12, more preferably SEQ ID NOs: 2 to 11), wherein the amino acid before substitution and the substituted amino acid are different from each other;

(H) an amino acid sequence having deletion, substitution, and/or addition of one or more amino acids in the amino acid sequence defined in (G) above, wherein the above amino acid substitutions have been maintained; and (I) an amino acid sequence having a sequence identity of at least 60% to the amino acid sequence defined in (G) above, wherein the above amino acid substitutions have been maintained.

Furthermore, in still another embodiment, the mutant-type phosphoenolpyruvate carboxylase may be a mutant-type PEPC having an amino acid sequence shown in any one of the following (J) to (L):

(J) an amino acid sequence obtained by introducing the amino acid substitution shown in (g) above, and the amino acid substitution shown in the above (i) or (l) into the amino acid sequence set forth in any one of SEQ ID NOs: 2 to 13 (preferably SEQ ID NOs: 2 to 12, more preferably SEQ ID NOs: 2 to 11), wherein the amino acid before substitution and the substituted amino acid are different from each other;

(K) an amino acid sequence having deletion, substitution, and/or addition of one or more amino acids in the amino acid sequence defined in (J) above, wherein the above amino acid substitutions have been maintained; and (L) an amino acid sequence having a sequence identity of at least 60% to the amino acid sequence defined in (J) above, wherein the above amino acid substitutions have been maintained.

In the meantime, in (B), (E), (H) and (K) above, the range of "one or more" is, for example, from 1 to 100, from 1 to 50, or from 1 to 30, preferably from 1 to 20, from 1 to 15, or from 1 to 10, and more preferably from 1 to 9, from 1 to 8, from 1 to 7, from 1 to 6, from 1 to 5, from 1 to 4, from 1 to 3, or from 1 to 2.

In addition, in (C), (F), (I) and (L) above, "at least 60%" may be replaced with preferably at least 70%, more preferably at least 80%, and still more preferably at least 85%, 90%, 91%, 92%, 93%, 94%, 95%, 96%, 97%, 98% or 99%.

Moreover, an embodiment in which "the amino acid sequence set forth in any one of SEQ ID NOs: 2 to 13 (preferably, SEQ ID NOs: 2 to 12, more preferably SEQ ID NOs: 2 to 11)" is replaced with "the amino acid sequence set forth in SEQ ID NO: 2" (that is, the wild-type PEPC amino acid sequence of *Corynebacterium glutamicum* strain ATCC13032) is particularly preferred.

In addition, in the above-described embodiments, the meaning remains that the mutant-type PEPC having the amino acid sequence defined in any of (A) to (L) above retains phosphoenolpyruvate carboxylase activity, and satisfies Condition (III).

Furthermore, in a specific embodiment, in the genetically modified microorganism according to the invention, for example, aspartate dehydrogenase (AspDH, EC 1.4.1.21), aspartate aminotransferase (AspC, EC2.6.1.1), and the aspartate ammonia-lyase (AspA, EC4.3.1.1,) (see FIG. 1) may be enhanced. More specifically, genes coding for these enzymes may additionally be introduced thereto for enhancement of these enzyme activities. As examples of the enzyme genes to be introduced into the recombinant coryneform bacteria of the invention, enzyme genes disclosed in Patent Documents 2, JP 2016-516435 A, and the like can be mentioned. The contents disclosed in these conventional art documents are also incorporated by reference into the present specification.

According to genetically modified microorganisms appropriately adopting each embodiment mentioned above, a starting substrate such as a sugar can more efficiently be employed for production of a target substance, and thus, a significant improvement in production efficiency of a target substance such as aspartic acid or a metabolite derived therefrom can be expected.

<Method for Producing Target Substance>

According to a third aspect of the invention, there is provided the following method for producing a target substance.

A method for producing a target substance, the method including: (p) producing a target substance using cells of the genetically modified microorganism according to the invention, or a treated cell product thereof; and (q) recovering the target substance.

In some embodiments, in Step (p), the target substance may be produced by culturing the genetically modified microorganism according to the invention under aerobic conditions where the genetically modified microorganism can substantially proliferate. The metabolism in the TCA cycle shown in FIG. 1 proceeds clockwise in coryneform bacteria under aerobic conditions. Therefore, in cases where an embodiment for the substance production under aerobic conditions is considered suitable for a type of the target substance, which is desired to be produced as a target, in consideration of the above-mentioned metabolism, such an embodiment may be selected.

On the other hand, in a culture medium or reaction solution under reducing conditions, microorganisms such as the genus *Escherichia* such as *E. coli* and coryneform bacteria do not substantially proliferate but cause unique metabolic systems under reducing conditions to function. Therefore, when coryneform bacteria according to the invention or a treated cell product thereof is reacted in a culture medium or a reaction solution under reducing conditions in the above way, it becomes possible to eliminate waste of nutrient sources due to proliferation and division of the bacterial cells, and thus, the conversion efficiency of the nutrient sources into the target substance can be improved. In addition, the genetically modified microorganism according to the invention is expected to remarkably significantly improve the conversion efficiency of nutrient sources into the target substance since the genetically modified microorganism has one or more reduced or inactivated enzyme activities in Conditions (I), (II), and (IV), and has phosphoenolpyruvate carboxylase activity showing resistance to feedback inhibition by a metabolite. Furthermore, according to such an embodiment in which reactions proceeds under reducing conditions where the microorganism does not substantially proliferate, as compared to the bioprocess under aerobic conditions involving division/proliferation of the cells, generation of fermentation heat can be prevented, and also, it is not required that sufficient aeration is secured during the course of the cultivation. Therefore, simplification of facilities required for the bioprocess, and energy reductions can be achieved, and thus, such an embodiment will be friendly to the global environment, and will result in cost reductions.

Therefore, it is preferable that, in Step (p), the cells of the genetically modified microorganism or a treated cell product thereof are reacted in a reaction medium (X) under reducing conditions where the genetically modified microorganism does not substantially proliferate, to produce the target substance.

Step (p')

Furthermore, in a more preferred embodiment, the method according to the invention further includes, before Step (p), (p') preliminarily culturing and proliferating the genetically modified microorganism under aerobic conditions in a predetermined culture medium (Y), wherein cells of the genetically modified microorganism proliferated in Step (p') or a treated cell product thereof are subjected to Step (p).

Although such an embodiment in which the method of the invention includes Step (p') would be involved also in the embodiment for the substance production under aerobic conditions, the embodiment is particularly preferably applied to a case where the substance production is performed in a reaction medium (X) under reducing conditions where the genetically modified microorganism does not substantially proliferate. The reason for this is explained as follows. In Step (p'), in cases where the genetically modified microorganism is caused to proliferate to a certain degree in advance under aerobic conditions, and then, in Step (p), the substance production is caused to proceed with a sufficient amount of the proliferated genetically modified microorganism in a reaction medium (X) where the genetically modified microorganism does not substantially proliferate, it becomes possible to perform efficient substance production using the genetically modified microorganism as if using a chemical catalyst. Furthermore, in some cases, the genetically modified microorganism may be recovered from the reaction medium (X) after the substance production in the reaction medium (X), and then, can be reused in a reaction in Step (p) of second or any subsequent cycles.

Hereinafter, specific configurations and elements which may be adopted in Step (p'), Step (p) and Step (q) will be described in detail in this order.

[Base Medium Constituting Culture Medium (Y)]

The culture medium (Y) is not particularly limited, and a suitable culture medium may be selected and employed depending on a type of genetically modified microorganism to be used in the method. Specifically, as the culture medium (Y), a natural or synthetic culture medium containing a carbon source, a nitrogen source, inorganic salts, other nutritional substances, and the like can be used. For example, ingredients contained in the culture medium are explained as follows.

For the carbon source, carbohydrate, more specifically, carbon-containing substances such as sugars including polysaccharides or monosaccharides, various materials including such substances, and the like can be mentioned, and the following ingredients can be mentioned as examples:

monosaccharides such as glucose, fructose, mannose, xylose, arabinose, and galactose; disaccharides such as sucrose, maltose, lactose, cellobiose, xylobiose, and trehalose; polysaccharides such as cellulose, starch, glycogen, agarose, pectin, and alginic acid; molasses and the like; non-edible agricultural wastes or non-edible biomass (resources including non-edible herbaceous or woody plants as raw materials) such as rice straws, forest residual materials, bagasse, and corn stover; saccharified solutions containing a plurality of sugars such as glucose and xylose, obtained by saccharifying energy crops, e.g., switchgrass, napier grass, and *Miscanthus*, with a diastatic enzyme or the like; sugar alcohols such as mannitol, sorbitol, xylitol, and glycerin; organic acids such as acetic acid, citric acid, lactic acid, fumaric acid, maleic acid, and gluconic acid; alcohols such as ethanol, propanol, and butanol; and hydrocarbons such as normal paraffin.

In addition, a single type of the carbon source can be used alone, or a mixture of two or more types thereof can be used.

For the nitrogen source, inorganic or organic ammonium compounds such as ammonium carbonate ($(NH_4)_2CO_3$), ammonium chloride, ammonium sulfate, ammonium nitrate, and ammonium acetate; urea, aqueous ammonia, sodium nitrate, potassium nitrate, or the like can be used. Furthermore, corn steep liquor, meat extracts, protein hydrolysates (e.g., casamino acid, tryptone, peptone, NZ-amine), nitrogen-containing organic compounds such as amino acid, or the like can also be used.

In addition, a single type of the nitrogen source can be used alone, or a combination of two or more types thereof can be used. The concentration of the nitrogen source in the culture medium may appropriately be adjusted depending on conditions such as a type or property of the genetically modified microorganism to be adopted, and the type of nitrogen compounds, and is not particularly limited. For example, the concentration may be set to about 0.1 to about 10 w/v %.

As examples of the inorganic salts, monopotassium phosphate, dipotassium phosphate, magnesium sulfate (hydrate), sodium chloride, iron(II) sulfate heptahydrate, iron(II) nitrate, manganese sulfate, zinc sulfate, cobalt sulfate, and calcium carbonate can be mentioned.

Additionally, a single type of inorganic salt may be used alone, or a mixture of two or more types thereof may be used. The concentration of the inorganic salt in the culture medium may be appropriately adjusted depending on conditions such as a type or property of the genetically modified microorganism to be adopted, and a type of inorganic salt, and is not particularly limited. For example, the concentration may be set to about 0.01 to about 1 (w/v %).

Furthermore, examples of the other nutritional substances include meat extracts, peptone, polypeptone, yeast extracts, dry yeasts, corn steep liquor, skim milk powder, hydrochloric acid hydrolysates of defatted soybean, extracts from animals, plants or microorganism cells, and degradation products thereof. The concentration of the other nutritional substances in the culture medium may be appropriately adjusted depending on conditions such as a type or property of the genetically modified microorganism to be adopted, and a type of nutritional substance, and is not particularly limited. For example, the concentration may be set to about 0.1 to about 10 (w/v %).

In addition, as needed, vitamins can also be added to the culture medium (Y). Examples of vitamins include biotin, thiamine, (vitamin B1), pyridoxine (vitamin B6), pantothenic acid, and inositol.

Moreover, as needed, an antifoaming agent such as a silicone-based antifoaming agent or a polyether-based antifoaming agent may be added. Since various antifoaming agents for bacterial culture media are commercially available, such antifoaming agents may be employed.

In addition, the pH of the culture medium (Y) is not particularly limited as long as it causes the genetically modified microorganism to be adopted to grow, and the pH thereof is preferably about 6 to about 8.

Furthermore, when the genetically modified microorganism to be adopted is a microorganism belonging to coryneform bacteria, the "A medium" [Inui, M. et al., Metabolic analysis of *Corynebacterium glutamicum* during lactate and succinate productions under oxygen deprivation conditions. J. Mol. Microbiol. Biotechnol. 7:182-196 (2004)], the "BT medium" [Omumasaba, C. A. et al., *Corynebacterium glutamicum* glyceraldehyde-3-phosphate dehydrogenase isoforms with opposite, ATP-dependent regulation. J. Mol. Microbiol. Biotechnol. 8:91-103 (2004)], the "NA medium" described in Examples of the present specification, and the like can preferably be employed as the culture medium (Y).

Microbial cells obtained by way of culturing and proliferating the genetically modified microorganism of the invention in the culture medium (Y) as described above or a treated cell product thereof may be subjected to Step (p).

In that case, it is only sufficient to appropriately set conditions for culturing the genetically modified microorganism, such that the genetically modified microorganism sufficiently proliferates to obtain a sufficient amount of the microbial cells or the treated cell product thereof. Specifically, the culturing temperature can be set to about 25° C. to 38° C. under aerobic conditions, and the culturing time can be set to about 12 hours to about 48 hours. Moreover, with regard to microbial cell stocks based on lyophilization or freeze storage, the microbial cell stocks can be inoculated on a solid medium at first, and then, colonies or the like, which would be confirmed to have grown on the solid culture medium, can be further inoculated into the aforementioned culture medium (Y), thus preparing the genetically modified microorganism to be subjected to Step (p).

Furthermore, a specific form of the "cells or the treated cell product thereof" is only sufficient to be in a state where the target substance can be produced, and is not particularly limited.

In some embodiments, as described above, the genetically modified microorganism is cultured and proliferated in the culture medium (Y) in Step (p'), and then, the culture medium (Y) containing the genetically modified microorganism may be subjected directly to Step (p) without recovering or separating the genetically modified microorganism from the culture medium (Y), to thus produce the target substance using cells of the genetically modified microorganism. Furthermore, as needed, prior to Step (p), a carbon source (sugars), a nitrogen source, inorganic salts, vitamins, a reducing agent, etc. that can be ingredients for the reaction medium (X) described later may be added to the culture medium (Y) containing the genetically modified microorganism obtained in the step (p'), and then, the resulting culture medium (Y) may be subjected to a reaction for production of the target substance in Step (p).

In another embodiment, cells obtained by separating and recovering from the culture medium (Y) the genetically modified microorganism, which has been cultured and proliferated in the culture medium (Y) in Step (p'), or a treated cell product obtained by subjecting the above separated/recovered cells to a predetermined physical or chemical treatment may be subjected to Step (p). Examples of techniques for separating and recovering the genetically modified microorganism from the culture medium (Y) include centrifugal separation, separation based on various filters, and decantation. In addition, the "treated cell product" in the invention is not particularly limited as long as the reaction for production of a target substance in Step (p) can be realized. More particularly, examples thereof include products obtained by subjecting the recovered microbial cells to various chemical treatments, and microbial cells immobilized on a carrier such as acrylamide, carrageenan, or other suitable polymers.

[Composition of Reaction Medium (X)]

A composition of the reaction medium (X) in the invention is not particularly limited as long as it realizes the reaction medium (X) under reducing conditions that cause the genetically modified microorganism not to substantially proliferate, while causing the reaction for production of a target substance by the genetically modified microorganism to proceed. The reaction medium (X) may contain a carbon source, a nitrogen source, inorganic salts, etc., and may be a natural medium derived from organisms, or may be an artificially synthesized medium. Examples of ingredients contained in the reaction medium (X) are described below.

For the carbon source, carbohydrate, more specifically, carbon-containing substances such as sugars including polysaccharides or monosaccharides, various materials including such substances, and the like can be mentioned, and the following ingredients can be mentioned as examples:

monosaccharides such as glucose, fructose, mannose, xylose, arabinose, and galactose; disaccharides such as sucrose, maltose, lactose, cellobiose, xylobiose, and trehalose; polysaccharides such as cellulose, starch, glycogen, agarose, pectin, and alginic acid; molasses and the like; non-edible agricultural wastes or non-edible biomass (resources including non-edible herbaceous or woody plants as raw materials) such as rice straws, forest residual materials, bagasse, and corn stover; saccharified solutions containing a plurality of sugars such as glucose and xylose, obtained by saccharifying energy crops, e.g., switchgrass, napier grass, and *Miscanthus*, with a diastatic enzyme or the like; sugar alcohols such as mannitol, sorbitol, xylitol, and glycerin; organic acids such as acetic acid, citric acid, lactic acid, fumaric acid, maleic acid, and gluconic acid; alcohols such as ethanol, propanol, and butanol; and hydrocarbons such as normal paraffin.

Among these, monosaccharides are preferable, and glucose is more preferable. Moreover, sugars including glucose (disaccharides, oligosaccharides, and polysaccharides) are also preferable. Furthermore, a single type of the carbon source can be used alone, or a combination of two or more types thereof can be used. In addition, the concentration of the carbon source in the reaction medium (X) is preferably about 1 to about 20 (w/v %), more preferably about 2 to about 10 (w/v %), and still more preferably about 2 to about 5 (w/v %). Additionally, the concentration of the sugar in the reaction medium (X) is, for example, about 1 to about 20 (w/v %), more preferably about 2 to 10 about (w/v %), and still more preferably about 2 to about 5 (w/v %).

For the nitrogen source, inorganic or organic ammonium compounds such as ammonium carbonate ($(NH_4)_2CO_3$), ammonium chloride, ammonium sulfate, ammonium nitrate, and ammonium acetate; urea, aqueous ammonia, sodium nitrate, potassium nitrate, or the like can be used. Furthermore, corn steep liquor, meat extracts, peptone, NZ-amine, protein hydrolysates, nitrogen-containing organic compounds such as amino acid, or the like can also be used.

In addition, a single type of the nitrogen source can be used alone, or a combination of two or more types thereof can be used. The concentration of the nitrogen source in the culture medium may appropriately be adjusted depending on conditions such as a type or property of the genetically modified microorganism to be adopted, and the type of nitrogen compounds, and is not particularly limited. For example, the concentration may be set to about 0.1 to about 10 w/v %.

As examples of the inorganic salts, monopotassium phosphate, dipotassium phosphate, magnesium sulfate (hydrate), sodium chloride, iron(II) sulfate heptahydrate, iron(II) nitrate, manganese sulfate, zinc sulfate, cobalt sulfate, and calcium carbonate can be mentioned.

Additionally, a single type of inorganic salt may be used alone, or a mixture of two or more types thereof may be used. The concentration of the inorganic salt in the culture medium may be appropriately adjusted depending on conditions such as a type or property of the genetically modified microorganism to be adopted, and a type of inorganic salt, and is not particularly limited. For example, the concentration may be set to about 0.01 to about 1 (w/v %).

In addition, as needed, vitamins can also be added to the reaction medium (X). Examples of vitamins include biotin, thiamine, (vitamin B1), pyridoxine (vitamin B6), pantothenic acid, and inositol.

In addition, the pH of the reaction medium (X) is not particularly limited as long as it is within the range that causes the reaction for production of a desired target substance to proceed. In general, the pH thereof is preferably about 6.0 to about 8.0, more preferably 6.5 to 8.0, and, for example, around 7.5.

In addition, for a specific preferable basic composition of the reaction medium (X), the aforementioned BT culture medium or the like can be mentioned, and, by way of appropriately adjusting the concentration of the carbon source (sugars), the concentration (xn) of at least one of nicotinic acid and a derivative thereof, the concentration (xb) of biotin, etc. in the above-described manners, on the basis of the composition of these culture media, a reaction medium (X) may be prepared.

[Reducing Conditions]

The reducing conditions where the coryneform bacteria do not substantially proliferate means that the reaction medium is in a reducing state to the extent that the genetically modified microorganism does not substantially proliferate, as it is literally interpreted. More specifically, such reducing conditions can be defined based on an oxidation-reduction potential of the reaction medium. The oxidation-reduction potential of the reaction medium (X) is preferably from about −200 mV to about −500 mV, and more preferably from about −250 mV to about −500 mV.

In addition, the oxidation-reduction potential of the reaction medium (X) can be measured using an oxidation-reduction potentiometer. Since there are also commercial products of oxidation-reduction potentiometers, such commercial products may be used for measurement of the oxidation-reduction potential of the reaction medium (X) in the invention.

The reducing state of the reaction medium can simply be estimated using a resazurin indicator (decolorization from blue to colorlessness will occur in a reducing state). However, for more precise control, the reducing state may be measured using an oxidation-reduction potentiometer (e.g., ORP Electrodes manufactured by Broadley-James Corporation).

For a method for preparing the reaction medium (X) in reducing conditions, various methods can be used without any particular limitations. For example, the following known methods for preparing an aqueous solution for the reaction can be used.

That is, an aqueous solution for the reaction may be used instead of distilled water or the like as a solvent for the reaction medium, and, as references for the method for preparing an aqueous solution for the reaction, for example, a method for preparing a culture solution for obligatory anaerobic microorganisms such as sulfate-reducing microorganisms (Pfennig, N. et al., (1981): The dissimilatory sulfate-reducing bacteria, In The Prokaryotes, A Handbook on Habitats Isolation and Identification of Bacteria, Ed. by Starr, M. P. et al., p 926-940, Berlin, Springer Verlag.), "Nogeikagaku Jikkensho (Agricultural Chemistry Experiments Book) Vol. 3, Ed. by Agricultural Chemistry Classroom in Kyoto University, 1990, Issue 26, published by Sangyo Tosho Publishing Co., Ltd." and the like may be used to thereby obtain an aqueous solution under desired reducing conditions.

Specifically, by way of subjecting distilled water or the like to a heat treatment or depressurization to remove a dissolved gas, an aqueous solution for the reaction in reducing conditions can be obtained. In this case, by way of treating distilled water or the like under a reduced pressure of about 10 mmHg or less, preferably about 5 mmHg or less, more preferably about 3 mmHg or less, for about 1 to about 60 minutes, preferably about 5 to about 40 minutes, a dissolved gas, particularly dissolved oxygen, is removed therefrom, thereby preparing an aqueous solution for the reaction in reducing conditions (anaerobic conditions).

Furthermore, also by way of adding a suitable reducing agent (e.g., thioglycolic acid, ascorbic acid, cysteine hydrochloride, mercaptoacetic acid, thiolacetic acid, glutathione, sodium sulfide) to distilled water or the like, thereby preparing an aqueous solution for the reaction in reducing conditions.

As needed, combination of the above-mentioned methods may also serve as a method for preparing an effective aqueous solution for the reaction in reducing conditions.

Additionally, it is preferable that the reducing conditions of the reaction medium (X) is maintained during the reaction. In order to continuously maintain the reducing conditions of the reaction medium (X) during the reaction, it is desirable to prevent oxygen from mixing into the reaction medium (X) from the outside of the reaction system as much as possible, and specifically, a method of shielding the reaction system with an inert gas such as a nitrogen gas, carbon dioxide gas, or the like can be mentioned therefor. As for a method of more effectively preventing the oxygen contamination, although there may be a case where it is required to appropriately add, to a reaction medium, a solution for adjusting and maintaining the pH of the reaction system, or a solution containing various nutrients dissolved therein, during the course of reaction, in order to allow metabolic functions inside cells of aerobic bacteria of the invention to work efficiently, it will be effective to remove oxygen from the solution to be added to the reaction medium, in advance.

In addition, in a case where the method of the invention includes Step (p'), the resulting culture medium (Y), in which a predetermined genetically modified microorganism of the invention has proliferated through Step (p'), may be adjusted so as to fulfill reducing conditions where the genetically modified microorganism does not substantially proliferate, for example, by way of: carrying out a predetermined operation with respect to the culture medium (Y); and/or adding a reducing agent to the culture medium (Y), and then, the culture medium (Y) may be used as the reaction medium (X) in Step (p).

[Reaction Conditions]

It is only sufficient that the reaction temperature in Step (p) is within the range where a desired target substance is produced. The reaction temperature may appropriately be set depending on properties or the like of a genetically modified microorganism to be adopted, and is not particularly limited. The reaction temperature is typically from about 20 to about 50° C., preferably from about 25 to about 47° C., and more preferably from about 27 to about 37° C., and, within such temperature ranges, a target substance can efficiently be produced.

It is only sufficient that the reaction time is appropriately adjusted so as to obtain a desired target substance, and is not particularly limited. For example, the reaction time may be from about 1 hour to about 7 days. In terms of efficient acquisition of a target substance, the reaction time may preferably be set to from about 1 hour to about 3 days, and, for example, from about 1 hour to 48 hours.

The reaction may be any of a batch type, fed-batch type, and continuous type. Among these, a batch type is preferred.

After completion of the reaction in Step (p), the genetically modified microorganism, the treated cell product thereof, or the like may be recovered from the reaction medium (X) based on a suitable operation such as centrifugal separation, and then, Step (p) may be repeated multiple times reusing the recovered genetically modified microorganism. Since the configuration in which Step (p) is repeated multiple times reusing the genetically modified microorganism in this manner results in reductions in production costs, thereby realizing efficient production of a target substance, the configuration is a preferred embodiment of the invention.

Step (q)

After a target substance is produced in Step (p), the target substance is recovered in Step (q). Herein, the term "recovering the target substance" in Step (q) refers to an idea encompassing recovering the target substance by way of harvesting a genetically modified microorganism and/or a culture solution or a reaction medium containing the target substance.

Although, as mentioned above, by way of harvesting the genetically modified microorganism and/or the culture solution or the reaction medium containing the target substance, the target substance may be recovered in Step (q), the target substance may also be recovered by way of, for example, separating and/or purifying the target substance from the culture solution, the reaction medium, the genetically modified microorganism cells, or the treated cell product thereof containing the target substance.

In an embodiment adopting such a process for separation and/or purification of the target substance, suitable separation/purification techniques may be adopted for the separation and purification processes, according to required purity or the like, in consideration of the type or purpose of the target substance. Although it is not particularly limited, the target substance can be recovered, as necessary, by combining, for example, any types of crystallization methods; any types of filtration techniques such as ultrafiltration; any types of chromatography techniques such as ion-exchange chromatography, affinity chromatography, hydrophobic chromatography and reversed-phase chromatography; concentration techniques; dialysis; and activated carbon adsorption techniques. Various types of these substance separation/purification techniques have been known, and therefore, such known techniques may appropriately be employed.

Furthermore, the method of the invention may further optionally include a step of washing, drying, crushing, pulverizing or granulating, and/or packaging the target substance.

<Type of Target Substance>

According to the method of the invention, various target substances can be produced using the genetically modified microorganism according to the invention with excellent yields. Although types of target substances would vary with a type of the genetically modified microorganism to be adopted, specific examples thereof include nucleic acid-related compounds (e.g., adenine, guanine, cytosine, thymine, uracil, 5'-guanylic acid, adenosine, ATP, and CDP-choline); various physiologically active substances such as hormone substances; carbohydrates or sugars; vitamin-related substances and coenzymes (e.g., vitamin C, vitamins B2 and B12, sorbose, NAD, FAD, and coenzyme A); proteins, peptides, amino acids; amino-acid derivatives such as L-3,4-dihydroxyphenylalanine (L-DOAP), 5-hydroxytryptophan, and pyrrolidone carboxylate; alcohols such as ethanol, butanol, and isopropanol; and various organic compounds such as phenol, catechol, 4-hydroxybenzoic acid, 4-aminobenzoic acid, anthranilic acid, gallic acid, succinic acid, fumaric acid, malic acid, shikimic acid, 3-dehydroshikimic acid, 3-dehydroquinic acid, protocatechuic acid, and chorismic acid.

In a specific embodiment, the target substance is at least one selected from the group consisting of an amino acid, an alcohol, an aromatic compound, and an organic acid.

Furthermore, in the invention, the target substance is preferably an L-amino acid or a derivative thereof. Specific examples of the amino acid include valine, leucine, isoleucine, glutamine, aspartic acid, glutamic acid, arginine, alanine, proline, cysteine, lysine, threonine, asparagine, phenylalanine, serine, methionine, glycine, tyrosine, histidine, tryptophan, cystine, and theanine.

Moreover, the derivative of L-amino acid may specifically be a metabolite derived from an L-amino acid in the metabolic system of the genetically modified microorganism.

Furthermore, in the invention, the target substance is preferably L-aspartic acid or a metabolite derived therefrom. The metabolite derived from L-aspartic acid includes amino acids or amino acid derivatives such as L-threonine, L-lysine, L-arginine, and L-homoserine.

In a specific embodiment, the target substance is citric acid, cis-aconitic acid, D-isocitric acid, α-ketoglutaric acid, succinyl CoA, succinic acid, or additional metabolites derived therefrom. These metabolites can efficiently be produced by culturing or reacting the genetically modified microorganism according to the invention under aerobic conditions (FIG. 1). In another embodiment, the target substance is oxaloacetic acid, L-malic acid, fumaric acid, or metabolites derived therefrom. These metabolites can efficiently be produced by reacting the genetically modified microorganism according to the invention under reducing conditions where the genetically modified microorganism does not substantially proliferate (FIG. 1).

In still another embodiment, the target substance is oxaloacetic acid, malic acid, or a metabolite produced via these compounds in a biosynthetic pathway.

In a preferred embodiment, the target substance is aspartic acid or a metabolite derived therefrom. In a more preferred embodiment, the target substance is aspartic acid, beta alanine, or asparagine.

The target substance may be produced, under predetermined conditions in the invention, through a metabolic system that the genetically modified microorganism inherited from the wild type microorganism, or may be produced through an additional metabolic system created artificially based on gene manipulations, mutation treatments, or the like, or may be produced by a combination of both of the above metabolic systems. Moreover, in the method for producing a target substance according to the invention, an embodiment further including a step of synthesizing the final target substance from a substance produced by the genetically modified microorganism, based on a chemical synthesis process or a cell-free system of enzymatic metabolism-based bioprocess is also encompassed.

In addition, although applications of the target substances produced in the invention are not limited at all, examples thereof include pharmaceutical application, food application, industrial application, fuel application, and cosmetic application. In addition, the target substance produced in the invention may be a substance employed directly for any types of applications, or may serve as an intermediate raw material employed for production of a final product.

<Mutant-Type PEPC>

According to a fourth aspect of the invention, there is provided the following mutant-type phosphoenolpyruvate carboxylase.

A mutant-type phosphoenolpyruvate carboxylase including an amino acid mutation with respect to an amino acid sequence of a wild-type phosphoenolpyruvate carboxylase of a microorganism belonging to coryneform bacteria, the amino acid mutation being capable of reducing feedback inhibition by aspartic acid in the wild-type phosphoenolpyruvate carboxylase activity, wherein the amino acid mutation at least includes: based on the amino acid sequence set forth in SEQ ID NO: 2, (g) an amino acid substitution of an amino acid corresponding to the 299th aspartic acid with asparagine;

(i) an amino acid substitution of an amino acid corresponding to the 813th lysine with a predetermined amino acid, wherein the substituted amino acid is not lysine; or (l) an amino acid substitution of an amino acid corresponding to the 917th asparagine with a predetermined amino acid, wherein the substituted amino acid is not asparagine, wherein the mutant-type phosphoenolpyruvate carboxylase has higher resistance to feedback inhibition by aspartic acid than that of a protein having only the amino acid substitution defined in (g), (i), or (l) above with respect to the amino acid sequence of the wild-type phosphoenolpyruvate carboxylase.

In a preferred embodiment, the mutant-type phosphoenolpyruvate carboxylase is a mutant-type PEPC having an amino acid sequence shown in any one of the following (J) to (L):

(J) an amino acid sequence obtained by introducing the amino acid substitution set forth in (g) above and the amino acid substitution set forth in (i) or (l) above into the amino acid sequence set forth in any one of SEQ ID NOs: 2 to 13 (preferably SEQ ID NOs: 2 to 12, more preferably SEQ ID NOs: 2 to 11);

(K) an amino acid sequence having deletion, substitution, and/or addition of one or more amino acids in the amino acid sequence defined in (J) above, wherein each of the above amino acid substitutions has been maintained; and (L) an amino acid sequence having a sequence identity of at least 60% to the amino acid sequence defined in (J) above, wherein each of the above amino acid substitutions has been maintained.

Herein, in (K) above, the range of "one or more" is, for example, from 1 to 100, from 1 to 50, or from 1 to 30, preferably from 1 to 20, from 1 to 15, or from 1 to 10, and more preferably from 1 to 9, from 1 to 8, from 1 to 7, from 1 to 6, from 1 to 5, from 1 to 4, from 1 to 3, or from 1 to 2.

In addition, in (L) above, "at least 60%" may be replaced with preferably at least 70%, more preferably at least 80%, and still more preferably at least 85%, 90%, 91%, 92%, 93%, 94%, 95%, 96%, 97%, 98% or 99%.

Moreover, in (J) above, an embodiment in which "the amino acid sequence set forth in any one of SEQ ID NOs: 2 to 13 (preferably, SEQ ID NOs: 2 to 12, more preferably SEQ ID NOs: 2 to 11)" is replaced with "the amino acid sequence set forth in SEQ ID NO: 2" (that is, the wild-type PEPC amino acid sequence of *Corynebacterium glutamicum* strain ATCC13032) is particularly preferred.

<Nucleic Acid Encoding Mutant-Type PEPC>

According to a fifth aspect of the invention, there is provided a nucleic acid coding for the mutant-type phosphoenolpyruvate carboxylase according to the fourth aspect.

In the invention, the "nucleic acid" may be provided in any of forms of deoxyribonucleic acid (DNA) and ribonucleic acid (RNA). Furthermore, the nucleic acid according to the invention may be in the form of a single strand or a double strand. Additionally, the nucleic acid is specifically an isolated nucleic acid, cDNA, or cRNA. Taking is into consideration that, for example, DNA is more chemically stable than RNA, the nucleic acid of the invention is preferably provided in the form of DNA. In addition, the nucleic acid may be chemically modified, e.g., methylated, in the invention.

Moreover, the nucleic acid according to the invention may include a replication origin or the like enabling autonomous replication in cells of a specific microorganism, and may be provided in the form of a plasmid, although these conditions are not necessarily essential. Furthermore, the nucleic acid according to the invention may include, in addition to the mutant-type PEPC coding sequence, a gene regulation sequence, such as a promoter sequence or Shine-Dalgarno sequence, such that the mutant-type PEPC according to the invention can be expressed in cells of microorganisms. The nucleic acid according to the invention may include the mutant-type PEPC coding region.

Furthermore, needless to say, a genetically modified microorganism into which the nucleic acid according to the invention has been introduced is encompassed by the invention as a part of the genetically modified microorganism in the first or second aspect of the invention. Additionally, needless to say, the method for producing a target substance using the genetically modified microorganism into which the nucleic acid according to the invention has been introduced is also encompassed by the invention as a part of the method for producing a target substance according to the third embodiment of the invention.

Hereinbefore, the specific embodiments of the invention have been described in detail, but the invention is not limited to the aforementioned embodiments. With respect to the configurations, the elements, and the features, various modifications, corrections, and combinations can be made without departing from the scope of the invention.

In addition, with regard to the terms "contain" and "have" in the invention, unless otherwise specified, existence of elements other than elements referred to as objects by these terms are not excluded, and these terms may mixedly be used herein. Moreover, besides the contents of Japanese Patent Application No. JP2019-76629, based on which this application claims priority, the contents of the documents mentioned in the present specification are incorporated by reference herein in their entirety.

EXAMPLES

<Example Using *Corynebacterium glutamicum*>

Using *Corynebacterium glutamicum* strain ATCC13032 as a starting material, recombinant coryneform bacteria in which predetermined enzyme activities were inactivated by a gene disruption technique, and into which a mutant-type phosphoenolpyruvate carboxylase gene having a predetermined amino acid substitution was introduced were prepared. Hereinafter, the procedures therefor are shown.

(1) Preparation of Gene-Deficient Strain (*Corynebacterium glutamicum* Strain ATCC13032 ΔldhΔsdhΔpoxB)

At first, a SacB gene fragment was amplified by the PCR method using plasmid pNIC-Bsa4 (Source BioScience) serving as a template, and a pair of primers shown in Table 12 below.

TABLE 12

| Primer name | Sequence and description | SEQ ID NO: |
|---|---|---|
| Primer F1 | 5'-GGGGAAGCTTGACGTCCACATATACCTGCC-3' Underlined part: HindIII-recognition site | 14 |
| Primer R1 | 5'-ATTCGGATCCGTATCCACCTTTAC-3' Underlined part: BamHI-recognition site | 15 |

The amplified DNA fragment and plasmid pHSG299 (Takara Bio Inc.) were subjected to a restriction enzyme treatment with BamHI and HindIII, and then, the resulting fragments were ligated using DNA ligation Kit Ver. 2 (Takara Bio Inc.), thereby obtaining plasmid pGE015.

Furthermore, a region with a size of about 1000 bp, present upstream of the ldh gene coding region, and a region with a size of about 1000 bp, downstream of the ldh gene coding region were each amplified through PCRs using, as a template, a genomic DNA of *Corynebacterium glutamicum* strain ATCC13032.

In addition, in the PCRs, a pair of Primers F2 and R2 were used for the upstream region, and Primers F3 and R3 were used for the downstream region (Table 13).

Figure 2A:
FIG. 2A is a diagram schematically showing a positional relationship between PCR primers used in Examples and a gene.

Additionally, in FIG. 2A, a positional relationship between each of the primers and a gene coding region is schematically shown.

TABLE 13

| Primer name | Sequence | SEQ ID NO: |
|---|---|---|
| Primer F2 | 5'-GACGGCCAGTGAATTTTTCATAC GACCACGGGCTA-3' | 16 |
| Primer R2 | 5'-GACAATCTTGTTACCGACGG-3' | 17 |
| Primer F3 | 5'-GGTAACAAGATTGTCACCCTGCG CGAAATTCAGAA-3' | 18 |
| Primer R3 | 5'-TACCGAGCTCGAATTGAACTCAC TGAAAAATGCTG-3' | 19 |

In addition, in the above procedures, for the PCRs, a thermal cycler T100™ (Bio-Rad Laboratories, Inc.) was used, and PrimeStar MAX (Takara Bio Inc.) was used as a PCR enzyme reagent. The same applies to PCRs in procedures described below unless otherwise specified.

With the In-Fusion cloning kit (Takara Bio Inc.), the amplified DNA fragments upstream and downstream of the ldh gene were ligated to the pGE15 vector that had been linearized by a restriction enzyme treatment with EcoRI, and thus, were cloned therein. The plasmid obtained in this way was named pGE033.

In the plasmid pGE33, the fragments of regions upstream and downstream of the ldh gene were inserted into the multiple cloning site in a state where the fragments were tandem-ligated. However, the coding region of the ldh gene was deficient therein. In addition, pGE33 can be replicated in *E. coli*, but is a plasmid that cannot be replicated in cells of coryneform bacteria. The plasmid pGE33 was introduced into *Corynebacterium glutamicum* strain ATCC13032 based on electroporation (2500 V, 25 μF, 200Ω; Van der Rest et al. Appl. Microbiol Biotechnol 52, pp 541-545, 1999). The sample after the electroporation was applied to an "A agar medium" (a composition for 1 L of the medium: 2 g of urea, 7 g of $(NH_4)_2SO_4$, 0.5 g of $KH_2PO_4$, 0.5 g of $K_2HPO_4$, 0.5 g of $MgSO_4 \cdot 7H_2O$, 6 mg of $FeSO_4 \cdot 7H_2O$, 4.2 mg of $MnSO_4 \cdot nH_2O$, 200 μg of D-biotin, 200 μg of thiamine hydrochloride, 2 g of yeast extract, 7 g of casamino acid, 20 g of glucose, and 16 g of agar, dissolved in 1000 mL of distilled water (pH 6.6)) containing 25 μg/ml of kanamycin, and culturing was carried out by an ordinary method.

In the meantime, since pGE33 has a kanamycin-resistance gene as a drug-resistance marker, growing strains that had proliferated on the A agar medium containing kanamycin, were strains into which the entire plasmids of pGE33 were incorporated into the genomic DNAs through occurrence of one-site homologous recombination between the plasmid and the wild-type ldh gene in the chromosome, as described above.

The growing strains obtained in this way were applied to LB agar media (composition for 1 L of the medium: 10 g of bactopeptone, 5 g of yeast extract, 10 g of sodium chloride, and 16 g of agar) added with 10% sucrose, and were cultured based on an ordinary method. In this case, any transformants retaining the SacB genes derived from pGE33 cannot be survived on the culture media added with sucrose, since a toxic substance is produced in transformants. On the other hand, any transformants from which plasmid-derived regions including the SacB gene are omitted through second homologous recombination can survive even on the culture media added with sucrose, and thus, the transformants, from which the plasmid-derived regions were omitted and which lacked the ldh genes, were obtained as growing strains. In addition, those from which the entire plasmid regions in the intact forms of pGE33 were omitted during the second homologous recombination return to the trait of the wild-type strain ATCC13032 retaining the intact ldh gene.

The microbial cell colonies obtained as growing strains on the LB agar media as described above were screened based on the colony PCR method using a pair of Primers F2 and R3, to obtain the ldh gene-deficient strains.

Since Primers F2 and R3 were primers designed at the 5'-terminal of the region with a size of about 1000 bp, present upstream of the ldh gene, and at the 3'-terminal of the region with a size of about 1000 bp, present downstream of the gene, respectively, it was supposed that DNA fragments with size of about 2 kb were produced in cases of ldh gene-deficient strains. The products obtained by the colony PCR were subjected to agarose electrophoresis (Molecular Cloning, Sambrook et al., 1989 Cold Spring Harbor Laboratory Press) based on the above-mentioned size of fragments serving as an indicator, and thus, microbial cells of colonies for which losses of the ldh genes had been confirmed were obtained as ldh gene-deficient strains (GES168).

Next, the sdhCAB genes were further deleted from the ldh gene-deficient strains (strains ATCC13032Δldh) (GES168), in the same manner as the above-described method of obtaining ldh gene-deficient strains.

That is, a region with a size of about 1000 bp, present upstream of the sdhCAB gene coding region, and a region with a size of about 1000 bp, present downstream of the gene coding region were each amplified using as a template the genomic DNA of *Corynebacterium glutamicum* strain ATCC13032.

Figure 2B:
FIG. 2B is a diagram schematically showing a positional relationship between PCR primers used in Examples and genes.

In addition, in the PCRs, a pair of Primers F4 and R4 were used for the upstream region, while Primers F5 and R5 were used for the downstream region (Table 14). Additionally, as mentioned above, the sdhCAB forms an operon including the sdhC coding region, the sdhA coding region, and the sdhB coding region, in the genome. A positional relationship between each of the primers and each of the coding region is shown in FIG. 2B.

TABLE 14

| Primer name | Sequence | SEQ ID NO: |
|---|---|---|
| Primer F4 | 5'-GACGGCCAGTGAATTGCGGCGGT CAAGGGCATCGA-3' | 20 |
| Primer R4 | 5'-GCTAGCGGCACCTCCAGTGTCGT TGT-3' | 21 |
| Primer F5 | 5'-GGAGGTGCCGCTAGCTCTTTAAT CCAAGTAAGTAC-3' | 22 |
| Primer R5 | 5'-TACCGAGCTCGAATTCTTCAAAG TAGTTCAGGGTG-3' | 23 |

Using the In-Fusion cloning kit (Takara Bio Inc.), the above-amplified DNA fragments corresponding to regions present upstream and downstream, respectively, of the SdhCAB gene, were ligated to a pGE15 vector that had been linearized by a restriction enzyme treatment with EcoRI, and thus, were cloned therein. The plasmid obtained in this way was named pGE020.

The plasmid pGE020 was introduced into the strain ATCC13032Δldh (GES168) based on the aforementioned electroporation, and thus, a strain ATCC13032ΔldhΔsdh (GES439) was obtained by way of selection with kanamycin-containing culture media and sucrose-containing culture media, as well as screening based on the colony PCR, in the same manner as the above acquisition of the strain ATCC13032Δldh (GES168).

Furthermore, the poxB gene was further deleted from the ATCC13032ΔldhΔsdh strain (GES439) according to the method of obtaining the gene-deficient strain.

That is, a region with a size of about 1000 bp, present upstream of the poxB gene coding region, and a region with a size of about 1000 bp, present downstream of the gene coding region, were each amplified using, as a template, a genomic DNA of *Corynebacterium glutamicum* strain ATCC13032.

In addition, in the PCRs, a pair of Primers F6 and R6 were used for the upstream region, and Primers F7 and R7 were used for the downstream region (Table 15).

Figure 2C:
FIG. 2C is a diagram schematically showing a positional relationship between PCR primers used in Examples and a gene.

Additionally, in FIG. 2C, a positional relationship between each of the primers and the gene coding region is schematically shown.

TABLE 15

| Primer name | Sequence | SEQ ID NO: |
|---|---|---|
| Primer F6 | 5'-GACGGCCAGTGAAAACGTTAATG AGGAAAACCG-3' | 24 |

TABLE 15-continued

| Primer name | Sequence | SEQ ID NO: |
|---|---|---|
| Primer R6 | 5'-AATTAATTGTTCTGCGTAGC-3' | 25 |
| Primer F7 | 5'-GCAGAACAATTAATTCTCGAGTC GAACATAAGGAATATTCC-3' | 26 |
| Primer R7 | 5'-TACCGAGCTCGAATTTTCCAGGT ACGGAAAGTGCC-3' | 27 |

Using the In-Fusion cloning kit (Takara Bio Inc.), the above-amplified DNA fragments corresponding to the regions present upstream and downstream, respectively, of the poxB gene were ligated to a pGE15 vector that had been linearized by a restriction enzyme treatment with EcoRI, and thus, were cloned therein. The plasmid obtained in this way was named pGE191. The plasmid pGE191 was introduced into the strain ATCC13032ΔldhΔsdh (GES439) according to the aforementioned electroporation, and thus, a strain ATCC13032ΔldhΔsdhΔpoxB (GES524) was obtained by way of selection with a kanamycin-containing culture medium and a sucrose-containing culture medium, followed by screening with the colony PCR, in the same manner as the acquisition of the ATCC13032Δldh strain (GES168).

(2) Introduction of Mutant-Type PEPC Genes into Gene-Deficient Strains (2-1) Construction of Shuttle Vector At first, a shuttle vector for *Corynebacterium glutamicum* ATCC13032 was constructed by way of linking a DNA fragment including a replication origin enabling autonomous replication in cells of the *Corynebacterium*, a DNA fragment including a replication origin enabling autonomous replication in *E. coli*, and a DNA fragment including a kanamycin-resistance gene.

The DNA fragment relating to the replication origin for the *Corynebacterium* was amplified based on the PCR method using pBL1 (kindly provided by Dr. Masaaki Wachi, nucleotide sequence GenBank ID: AF092037.1) serving as a template, and using a pair of Primers F8 and R8 shown in Table 16. Moreover, the DNA fragment relating to the replication origin for *E. coli* was amplified based the PCR method using pMW119 (Takara Bio Inc.) serving as a template, and using a pair of Primers F9 and R9 shown in Table 16. Furthermore, the kanamycin-resistance gene DNA fragment was amplified based on the PCR method using pHSG299 (Takara Bio Inc.) serving as a template, and using a pair of Primers F10 and R10 shown in Table 16.

TABLE 16

| Primer name | Sequence | SEQ ID NO: |
|---|---|---|
| Primer F8 | 5-TTTCTACGCGGCCGCAACAACAAG ACCCATCATAG-3' | 28 |
| Primer R8 | 5'-TCGTCGACGGTACCGGATCCCAT GCACATGCAGTCATGTC-3' | 29 |
| Primer F9 | 5'-GAACCGTAAAAAGGCGACAGTAA GACGGGTAAGCC-3' | 30 |
| Primer R9 | 5'-GCGGCCGCGTAGAAAGTAACGGT GAACAGTTGTTC-3' | 31 |

TABLE 16-continued

| Primer name | Sequence | SEQ ID NO: |
|---|---|---|
| Primer F10 | 5'-CGGTACCGTCGACGATATCGAGG TCTGCCTCGTGAAGAA-3' | 32 |
| Primer R10 | 5'-GCCTTTTTACGGTTCGATTTATT CAACAAAGCCGC-3' | 33 |

A product obtained by circularizing the above-obtained three amplified fragments based on ligation of the fragments with the In-Fusion cloning kit (TAKARA) was named plasmid pGEK004 serving as a shuttle vector for *Corynebacterium glutamicum* ATCC13032.

(2-2) Construction of Plasmids Containing Various Mutant-Type Phosphoenolpyruvate Carboxylase Genes Next, DNA fragments of mutant-type phosphoenolpyruvate carboxylase genes having various types of amino acid substitutions were amplified through the site specific mutagenesis, which is based on the PCR, and then, plasmids obtained by inserting each of the above DNA fragments into the shuttle vector pGEK004 were constructed.

Names of the constructed plasmids, and contents of the amino acid substitutions for the PEPC are shown in Table 17 below.

TABLE 17

| Plasmid name | Amino acid substitutions in Mutant-type PEPCs |
|---|---|
| pGE320 | D299N |
| pGE343 | K813S |
| pGE321 | N917G |
| pGE333 | D299N and K813S |
| pGE322 | D299N and N917G |

Hereinafter, methods for constructing each of the above plasmids will be described in detail.

(2-2-1) pGE320 (ppcD299N Gene)

At first, a DNA fragment including a gapA gene promoter region that serves as a promoter capable of functioning in a coryneform bacterium was amplified based on the PCR, using, as a template, a genomic DNA of the Coryne strain ATCC13032 and using a pair of Primers F11 and R11 shown in Table 18.

TABLE 18

| Primer name | Sequence and description | SEQ ID NO: |
|---|---|---|
| Primer F11 | 5'-CATGTGCATGGGATCGAAGAAAT TTAGATGATTGA-3' | 34 |
| Primer R11 | 5'-AAATCCGTTAATACCAACAC-3' | 35 |
| Primer F12 | 5'-GGTATTAACGGATTTATGACTG ATTTTTTACGCGA-3' *The underlined part refers to a coding region. | 36 |
| Primer R12-1 | 5'-CATGCGGTTCGACAGGCTGAGCT CATGCT-3' *The underlined part corresponds to a mutation-introduced site of D299N. | 37 |

TABLE 18-continued

| Primer name | Sequence and description | SEQ ID NO: |
|---|---|---|
| Primer F13-1 | 5'-CTGTCGAACCGCATGAATAAGGTC ACCCC-3' *The underlined part corresponds to a mutation-introduced site of D299N. | 38 |
| Primer R13 | 5'-CGACGGTACCGGATCGCTGGAGAG TCCGCCGCCTT-3' *The underlined part corresponds to a sequence present 3' downstream of the PEPC-coding region. | 39 |

For the PEPC coding region, at first, a region of about 900 bp corresponding to the N-terminal side of PEPC was amplified based on the PCR method using the genomic DNA of the strain ATCC13032 and using a pair of Primers F12 and R12-1 shown in Table 18, while a region of about 3500 bp including the C-terminal side region of PEPC was amplified in the similar manner using the genomic DNA of the strain ATCC13032 as a template and using a pair of Primers F13-1 and R13 shown in Table 18.

Meanwhile, Primer R12-1 (reverse primer) used for the amplification of the N-terminal side fragment of PEPC, and Primer F13-1 (forward primer) used for the amplification of the C-terminal side fragment of PEPC overlap with each other over the coding region of PEPC, and also, each include mutant codons relating to D299N ("GTT"/"AAC", which are underlined in Table 18, respectively). In addition, the corresponding wild-type codon is "GAC" (sense strand).

Using the In-Fusion cloning kit (Takara Bio Inc.), the three DNA fragments obtained in the above way were tandem-ligated to a linearized vector fragment that had been obtained by way of subjecting pGEK004 to a restriction enzyme treatment with BamHI, and thus, the fragments were circularized, thereby obtaining plasmid pGE320.

(2-2-2) pGE343 (ppcK813S Gene)

At first, a DNA fragment including a gapA gene promoter region was amplified based on the PCR reaction in the same manner as the above preparation of pGE320.

Furthermore, for the PEPC coding region, at first, a region of about 2430 bp corresponding to the N-terminal side of PEPC was amplified based on the PCR method using the genomic DNA of the strain ATCC13032 as a template and using a pair of Primer F12 shown in Table 18 and Primer R12-2 shown in Table 19, while a region of about 530 bp including the C-terminal side region of PEPC was amplified in the same manner using the genomic DNA of the strain ATCC13032 as a template and using a pair of Primer F13-2 shown in Table 19 and Primer R13 shown in Table 18.

TABLE 19

| Primer name | Sequence and description | SEQ ID NO: |
|---|---|---|
| Primer R12-2 | 5'-CGAGGACATCACCTGAGCCATG-3' *The underlined part corresponds to a mutation-introduced site of K813S. | 40 |
| Primer F13-2 | 5'-CAGGTGATGTCCTCGGCAGAGCTG CGTTTGGCAAA-3' *The underlined part corresponds to a mutation-introduced site of K813S. | 41 |

Meanwhile, Primer R12-2 (reverse primer) used for the amplification of the N-terminal side fragment of PEPC and Primer F13-2 (forward primer) used for the amplification of the C-terminal side fragment of PEPC overlap with each other over the coding region of PEPC, and also, each include mutant codons relating to K813S ("CGA"/"TCG" which are underlined in Table 19, respectively). In addition, the corresponding wild-type codon is "AAG" (sense strand).

Then, using the In-Fusion cloning kit (Takara Bio Inc.), the three DNA fragments obtained in the above way were tandem-ligated to a linearized vector fragment that had been obtained by way of subjecting pGEK004 to a restriction enzyme treatment with BamHI, and the DNA fragments were circularized, thereby obtaining plasmid pGE343.

(2-2-3) pGE321 (ppcN917G Gene)

At first, a DNA fragment including a gapA gene promoter region was amplified based on the PCR reaction in the same manner as the above preparation of pGE320.

Furthermore, for the PEPC coding region, at first, the region of about 2430 bp corresponding to the N-terminal side of PEPC was amplified based on the PCR method using the genomic DNA of the strain ATCC13032 as a template, and using a pair of Primer F12 shown in Table 18 and Primer R12-3 shown in Table 20, while a region of about 530 bp including the C-terminal side region of PEPC was amplified in the same manner using the genomic DNA of the strain ATCC13032 as a template and using a pair of Primer F13-3 shown in Table 20 and Primer R13 shown in Table 18.

TABLE 20

| Primer name | Sequence and description | SEQ ID NO: |
|---|---|---|
| Primer R12-3 | 5'-GCCGGAGCCGCGCAGCGCAGTGG AAAGAC-3' *The underlined part corresponds to a mutation-introduced site of N917G. | 42 |
| Primer F13-3 | 5'-CTGCGCGGCTCCGGCTAGTCCAG CCGGCT-3' *The underlined part corresponds to a mutation-introduced site of N917G. | 43 |

In this case, Primer R12-3 (reverse primer) used for amplification of the N-terminal side fragment of PEPC and Primer F13-3 (forward primer) used for the amplification of the C-terminal side fragment of PEPC overlap with each other over the coding region of PEPC, and also, each include mutant codons relating to N917G ("GCC"/"GGC" which are underlined in Table 20, respectively). In addition, the corresponding wild-type codon is "AAC" (sense strand).

Then, using the In-Fusion cloning kit (Takara Bio Inc.), the three DNA fragments obtained in the above way were tandem-ligated to a linearized vector fragment that had been obtained by way of subjecting pGEK004 to a restriction enzyme treatment with BamHI, and thus, the DNA fragments were circularized, thereby obtaining plasmid pGE321.

(2-2-4) pGE333 (ppcD299N/K813S Gene)

A DNA fragment corresponding to the gapA gene promoter region and the ppc gene N-terminal side region was amplified based on the PCR method using the aforementioned plasmid pGE320 serving as a template and using a pair of Primers F12 and R13-2. Furthermore, a DNA fragment corresponding to the C-terminal side of the ppc gene and a region 3' downstream thereof was amplified in the same manner based on the PCR method using a pair of Primers F-14-2 and R14.

Using the In-Fusion cloning kit (Takara Bio Inc.), the two DNA fragments obtained in the above way were tandem-ligated to a linearized vector fragment that had been obtained by way of subjecting pGEK004 to a restriction enzyme treatment with BamHI, and thus, the DNA fragments were circularized, thereby obtaining plasmid pGE333.

(2-2-5) pGE322 (ppcD299N/N917G Gene)

A DNA fragment corresponding to the gapA gene promoter region and the ppc gene N-terminal side region were amplified by the PCR method using the aforementioned plasmid pGE320 serving as a template and using a pair of Primer F12 and Primer R13-3. Further, DNA fragments corresponding to the ppc gene C-terminal and 3' downstream regions were amplified similarly by the PCR method using a pair of a primer F-14-3 and a primer R14.

Using the In-Fusion cloning kit (Takara Bio Inc.), the two DNA fragments obtained in the above way were tandem-ligated to a linearized vector fragment that had been obtained by way of subjecting pGEK004 to a restriction enzyme treatment with BamHI and thus, the DNA fragments were circularized, thereby obtaining plasmid pGE322.

(2-3) Preparation of Recombinant Coryneform Bacteria by Way of Introducing Mutant-Type ppe Genes into Gene-Deficient Strains of *Corynebacterium glutamicum*, and Production of Aspartic Acid Using the Coryneform Bacteria Test Example 1

(Test Procedures)

Based on the above-described electroporation, the gene-deficient strain GES439 (ATCC13032ΔldhΔsdhCAB strain) of *Corynebacterium glutamicum* prepared in Section (1) above was transformed with each of the plasmids pGEK004, pGE320, pGE343, pGE321, pGE333, and pGE322 constructed in Section (2-2) above, thereby obtaining recombinant coryneform bacteria.

Then, each of the recombinant strains of coryneform bacteria was pre-cultured in 5 mL of the “A medium” (in test tube). 2 mL of each of the resulting pre-culture solutions was inoculated into 100 mL of the “NA medium” (2 g of urea, 7 g of $(NH_4)_2SO_4$, 0.5 g of $KH_2PO_4$, 0.5 g of $K_2HPO_4$, 0.5 g of $MgSO_4 \cdot 7H_2O$, 6 mg of $FeSO_4 \cdot 7H_2O$, 4.2 mg of $MnSO_4 \cdot nH_2O$, 200 μg of D-biotin, 200 μg of thiamine hydrochloride, 1 g of yeast extract, and 10 g of glucose dissolved in 1000 mL of distilled water) in a 500-mL flask, so as to prepare two culture samples for each strain, and then, the prepared culture samples were subjected to shaking culture at 33° C. at 200 rpm for 20 hours.

After the cultivation, culture solutions in the above two flasks for each strain were combined together, the liquid culture medium supernatant was removed therefrom based centrifugation, and the separated microbial cells were suspended in 60 mL of BT solution (7 g of $(NH_4)_2SO_4$, 0.5 g of $KH_2PO_4$, 0.5 g of $K_2HPO_4$, 0.5 g of $MgSO_4 \cdot 7H_2O$, 6 mg of $FeSO_4 \cdot 7H_2O$, 4.2 mg of $MnSO_4 \cdot nH_2O$ per Litter), such that the OD value was adjusted to be around 30 to 40. This was transferred to a 100 mL medium bottle with a stirring bar placed inside, and then, 5 mL of 50% glucose and 5 mL of 2 M $(NH_4)_2CO_3$ were further added thereto. This medium bottle was put in a thermostat bath set to 33° C., and was left to stand still, thereby causing a reaction while stirring the reaction solution. The pH of the reaction solution was adjusted to 7.5 with 2 M $(NH_4)_2CO_3$ using a pH controller. In addition, when, during the course of a reaction based on coryneform bacteria in the BT solution, an oxidation-reduction potential of the reaction solution is measured with an oxidation-reduction potentiometer (ORP sensor), the oxidation-reduction potential generally falls approximately between −400 mV to −500 mV.

24 hours after from the start of the reaction, 0.5 mL of the reaction solution was collected, a supernatant thereof was separated by centrifugation, and then, the amount of consumed glucose and amounts of produced amino acids were measured. For the measurement of the amounts of amino acids, an amino acid analysis system Prominence (SHIMADZU CORPORATION) was used.

Results

Figure 4:
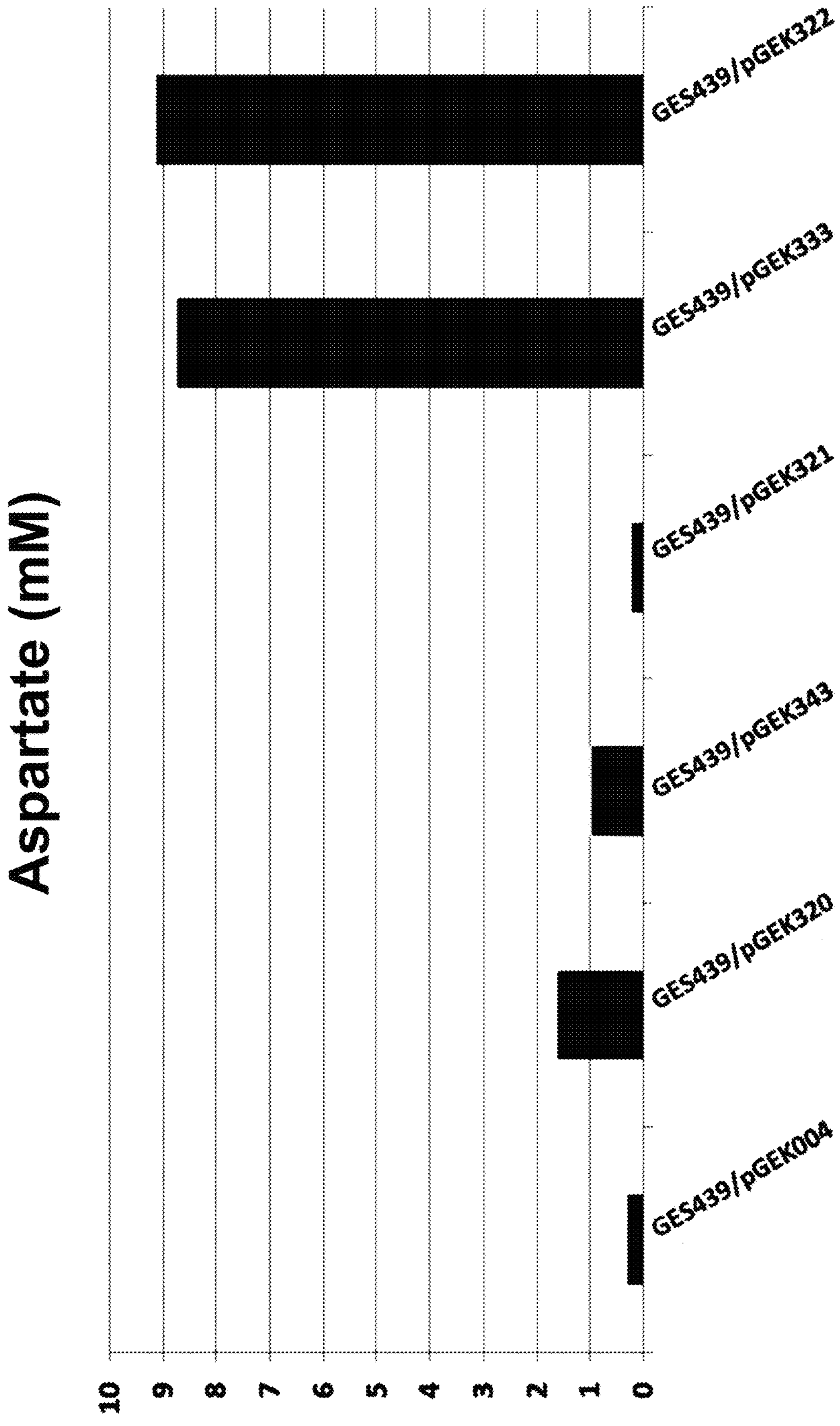
FIG. 4 is a diagram showing results of Test Example 1 in Examples.

The results of the aspartic acid production test are shown in FIG. 4. In the graph of FIG. 4, the vertical axis indicates aspartic acid concentrations in samples after the reactions. Furthermore, Table 21 shows genetic types of the obtained recombinant coryneform bacteria, and aspartic acid production efficiencies (%) calculated based on the aspartic acid production test. Each of the values in the aspartic acid production efficiency (%) refers to a ratio of the produced aspartic acid to 0.5 mol of glucose incorporated into the microbial cells.

TABLE 21

| Names of recombinant coryneform bacteria | Genotype | Amino acid substitutions in mutant-type PEPCs | Aspartate production efficiency (%) |
|---|---|---|---|
| GES439/pGEK004 | ΔldhΔsdhCAB | Any amino acid substitutions of mutant-type PEPCs were NOT introduced. | 0.3 |
| GES439/pGE320 | ΔldhΔsdhCAB | D299N | 1.2 |
| GES439/pGE343 | ΔldhΔsdhCAB | K813S | 0.4 |
| GES439/pGE321 | ΔldhΔsdhCAB | N917G | 0.2 |
| GES439/pGE333 | ΔldhΔsdhCAB | D299N and K813S | 8.1 |
| GES439/pGE322 | ΔldhΔsdhCAB | D299N and N917G | 7.8 |

First, in all of the recombinant coryneform bacteria prepared in this test example, including GES439/pGEK004, which served as a negative control, the ldh gene (lactate dehydrogenase gene) and the sdhCAB gene (succinate dehydrogenase gene) in the genome were disrupted.

In the above background, for GES439/pGE320 and GES439/pGE343, into which the ppc genes (phosphoenolpyruvate carboxylase genes) having only the respective single amino acid substitutions of D299N and K813S had further been introduced, slight increases in the aspartic acid production efficiencies were observed, relative to GES439/pGEK004, which served as a negative control. On the other hand, any increase in aspartic acid production efficiency was not observed for GES439/pGE321, into which the ppc gene having only a single amino acid substitution of N917G had been introduced.

To the contrary, for GES439/pGE333 and GES439/pGE322 having amino acid substitutions of: a combination of D299N and K813S; and a combination of D299N and N917G, respectively, the aspartic acid production efficiencies showed values of 8.1% and 7.8%, respectively. In this way, for GES439/pGE333 and GES439/pGE322, significant increases were observed relative to GES439/pGEK004, which served as a negative control.

Thus, it was realized that, when introduction of a mutant-type phosphoenolpyruvate carboxylase (PEPC) having a combination of: an amino acid substitution at the N-terminal side; and an amino acid substitution at the C-terminal side is adopted under the conditions where the predetermined enzyme activities are inactivated, the production efficiency of a substance will significantly be improved.

Test Example 2

(Test Procedures)

Based on the above-described electroporation, the gene-deficient strains GES168 (Δldh), GES439 (ΔldhΔsdhCAB) and GES524 (ΔldhΔsdhCABΔpoxB) of *Corynebacterium glutamicum* prepared in Section (1) above were each transformed with the plasmid pGE333 (ppcD299N/K813S) constructed in Section (2-2) above, thereby obtaining recombinant coryneform bacteria.

A test for production of aspartic acid was performed using the above-obtained recombinant coryneform bacteria based on the same manner as Test Example 1.

Results

Figure 5:
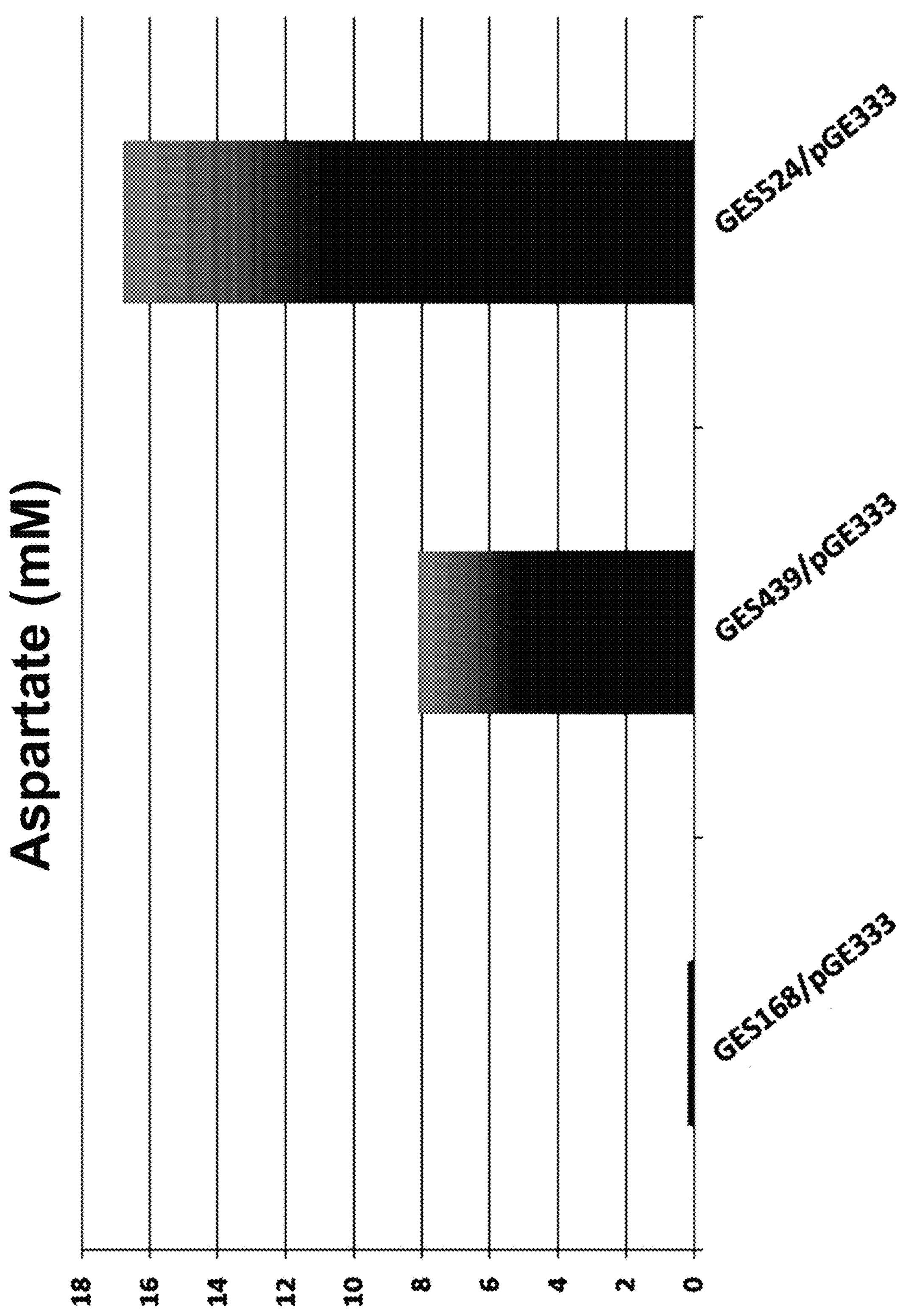
FIG. 5 is a diagram showing results of Test Example 2 in Examples.

Results of the test for production of aspartic acid are shown in FIG. 5. In the graph of FIG. 5, the vertical axis refers to concentrations of aspartic acid in the samples after the reactions. Furthermore, in Table 22 below, genetic types of the obtained recombinant coryneform bacteria and aspartic acid production efficiencies (%) calculated in the test for production of aspartic acid are shown. Each of values of the aspartic acid production efficiencies (%) is a ratio of aspartic acid that was actually produced, to 0.5 mol of glucose incorporated into the microbial cells. The value is a value based on the fact that, theoretically, 2 mol of aspartic acid can be produced from 1 mol of glucose.

TABLE 22

| Names of recombinant coryneform bacteria | Genotype | Amino acid substitutions in mutant-type PEPCs | Aspartate production efficiency (%) |
|---|---|---|---|
| GES168/pGE333 | Δldh | D299N and K813S | 0.2 |
| GES439/pGE333 | ΔldhΔsdhCAB | Same as above | 8.1 |
| GE5524/pGE333 | ΔldhΔsdhCABΔpoxB | Same as above | 16.8 |

First, with regard to the strain GES168/pGE333, which had the mutant-type ppc gene having an amino acid substitution of a combination of D299N/K813S, but which was deficient only in the ldh gene, any significant improvements were not observed in the aspartic acid production efficiency, as shown in FIG. 5 and Table 22.

On the other hand, as confirmed in Test Example 1, with regard to the strain ES439/pGE333, which also had the mutant-type ppc gene having an amino acid substitution of a combination of D299N/K813S, but which was deficient in two genes, namely the ldh gene and sdhCAB, significant improvements were observed in the aspartic acid production efficiency.

Even more surprisingly, with regard to the strain GES524/pGE333, which also had the mutant-type ppc gene having an amino acid substitution of a combination of D299N/K813S, but which was deficient in three genes, namely the ldh gene, sdhCAB, and the poxB gene (pyruvate:quinone oxidoreductase), the aspartic acid production efficiency showed a value of 16.8%, and thus, this strain exhibited remarkably significant improvements in the production efficiency.

Test Example 3

In Test Examples 1 and 2, after the recombinant coryneform bacteria were proliferated in advance using the "A media", and the "NA media" under aerobic cultivation conditions, the culture medium supernatants were then removed by centrifugal separation, and then, the separated microbial cells were suspended in predetermined amounts of BT solutions to perform the reactions for production of aspartic acid. On the other hand, in this test example, after the recombinant coryneform bacteria were proliferated using the "A medium" and the "NA medium" under aerobic cultivation conditions, a reaction for production of aspartic acid was performed using the culture solution itself without separation of the microbial cells based on centrifugation or the like. Hereinafter, the procedures therefor will be shown.

At first, GES439/pGEK004 (ΔldhΔsdhCAB/without introduction of mutant-type PEP) and GES439/pGE322 (ΔldhΔsdhCAB/mutant-type PEPC of D299N and N917G) prepared in Test Example 1 were each inoculated into 5 mL of the "A media" in test tubes to perform pre-cultivation. Then, 2 mL of each of the resulting pre-culture solutions was inoculated into 100 mL of the "NA medium" in a 500-mL flask, and the culture samples were subjected to shaking culture at 33° C. at 200 rpm for 20 hours. After the cultivation, 60 mL of each of the sample culture solutions was transferred directly to a 100-mL medium bottle with a stirring bar placed therein, and then, 5 mL of 50% glucose, and 5 mL of 2 M $(NH_4)_2CO_3$ were added thereto. The medium bottle was placed inside a thermostat bath set to 33° C., and was left to stand still therein to thereby perform a reaction while stirring the sample culture solution with the stirring bar. After 24 hours, 0.5 mL of the reaction solution was harvested, the supernatant was collected based on centrifugation, and then, an amount of consumed glucose, and amounts of produced amino acids were measured.

In addition, for identification and measurement of amino acids, an amino acid analysis system Prominence (SHIMADZU CORPORATION) was used.

Results

Figure 6:
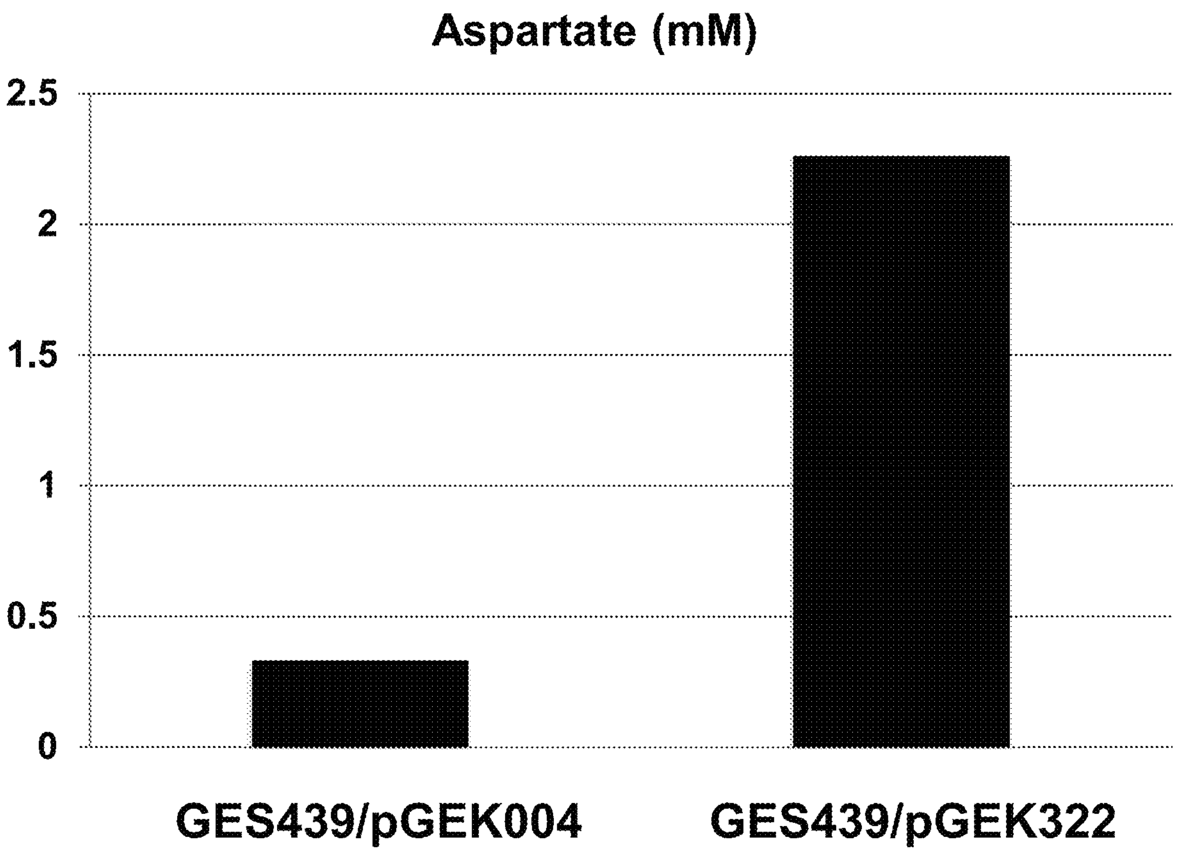
FIG. 6 is a diagram showing results of Test Example 3 in Examples.

Results of the test for production of aspartic acid in this test example are shown in FIG. 6. In the graph of FIG. 6, the vertical axis refers to concentrations of aspartic acid in the samples after the reactions.

Furthermore, in Table 23 below, genetic types of the obtained recombinant coryneform bacteria, and aspartic acid production efficiencies (%) calculated in the test for production of aspartic acid are shown. A value of the aspartic acid production efficiency (%) is, as described above, a ratio of aspartic acid that was actually produced, to 0.5 mol of glucose incorporated into the microbial cells.

TABLE 23

| Names of recombinant coryneform bacteria | Genotype | Amino acid substitutions in mutant-type PEPCs | Aspartate production efficiency (%) |
|---|---|---|---|
| GES439/pGEK004 | ΔldhΔsdhCAB | Any amino acid substitutions of mutant-type PEPCs were introduced. | 0.2 |
| GES439/pGE322 | ΔldhΔsdhCAB | D299N and N917G | 4.0 |

Also in this test example, while the aspartic acid production efficiency for GES439/pGEK004, which served as a negative control, was at a remarkably poor level of 0.2%. On the other hand, GES439/pGE322 having an amino acid substitution of a combination of D299N and N917G exhibited 4.0% for the aspartic acid production efficiency, and thus, such significant increases therefor were observed. That is, according to this test example, it was revealed that the conversion to a target substance (aspartic acid) can efficiently be achieved even in a case where a culture in which the recombinant microbial cells have been proliferated in advance through pre-cultivation under aerobic conditions is employed directly for production of a substance (aspartic acid) without removing the part of culture medium supernatant based on centrifugal manipulations or the like.

As shown in Test Examples 1 to 3 above, it becomes possible to improve efficiency of conversion of a starting substrate, e.g., sugars, to a target substance when a predetermined recombinant coryneform bacterium of the invention.

<Examples Using *Escherichia coli* (*E. coli*)>

Next, an example in which a recombinant microorganism according to the invention, and production of aspartic acid using the recombinant microorganism were carried out using *Escherichia coli* (*E. coli*) will be shown.

Predetermined genes were disrupted in *Escherichia coli* in accordance with the following procedures.

(1) Disruption of pflB Gene

At first, the strain BW25113 (lacI$^q$ rrnB$_{T14}$ ΔlacZ$_{wj16}$ hsdR514 ΔaraBAD$_{AH33}$ ΔrhaBAD$_{LD78}$) described in Datsenko and Wanner (Proc Natl Acad Sci USA 2000, 97:6640-6645.) was prepared in accordance with the method described in this reference document.

Then, in order to disrupt the pflB gene in the above strain BW25113, the strain was transformed in advance with a bacteriophage recombinase expression vector pKD46 (Life Science Market). The resulting transformant was inoculated into 100 mL of the LB culture medium (containing arabinose at a final concentration of 10 mM), and this was cultured at 30° C. until a turbidity of the culture medium at OD600 reached around 0.6. The resulting microbial cells of recombinant *E. coli* were washed with 10% glycerol three times, and were finally suspended in 1 mL of 10% glycerol, thereby preparing competent cells.

Next, a DNA fragment including a coding region for a kanamycin-resistance gene was amplified based on the PCR method using a pair of Primers F14 and R14 shown in Table 24 below, and further using pKD13 serving as a template. In that case, Primers F14 and R14 includes nucleotide sequences homologous to regions upstream and downstream, respectively, of the coding region for the pflB gene in the chromosomal DNA of *E. coli*.

TABLE 24

| Primer name | Sequence and description | SEQ ID NO: |
|---|---|---|
| Primer F14 | 5'-CGAAGTACGCAGTAAATAAAAAA TCCACTTAAGAAGGTAGGTGTTACAT GATTCCGGGGATCCGTCGACC-3' | 44 |
| Primer R14 | 5'-TTTTACTGTACGATTTCAGTCAA ATCTAATTACATAGATTGAGTGAAGG TTGTAGGCTGGAGCTGCTTCG-3' | 45 |

The resulting PCR product was purified using NucleoSpin Gel and PCR Clean-up (Takara Bio Inc.).

Then, 10 μL of the purified PCR product was added to 150 μL of the above-prepared competent cells, followed by performing the gene introduction based on electroporation (2500 V, 25 ρF, 200Ω). The resulting transformants were caused to proliferate on an LB agar medium containing 50 μg/mL of kanamycin, and thus, the growing strains were selected. Disruption of the pflB gene in each of the selected growing strains was confirmed by way of cultivation of the strains in predetermined culture media, followed by performing organic acid analysis on a supernatant of the culture solution, from which the microbial cells had been separated through centrifugal manipulations. That is, in the organic acid analysis, a strain in which production of formic acid had not been observed was collected as a pflB gene-deficient strain. In addition, the organic acid analysis was performed based on HPLC analysis using TSKgel OApak column (Tosoh Corporation).

Then, the strain BW25113ΔpflB::Km obtained in the above way was transformed with pCP20 (Life Science Market) at 30° C., and then, the obtained transformant was streaked on an LB culture medium plate, containing no antibiotic substance, followed by cultivation at 42° C. In the meantime, pCP20 is a plasmid vector designed so as to express the Flp recombinase, which removes the kanamycin-resistance gene cassette, under high culture temperature conditions. According to this, over the LB culture medium plate, on which the strains had been cultured at 42° C., a colony that showed susceptibility to kanamycin was selected, and the colony was named BW25113ΔpflB.

(2) Disruption of the ldhA Gene

The strain BW25113ΔpflB obtained in the above way was again transformed with pKD46 (Life Science Market), and then, competent cells of the resulting transformant were prepared in the same manner.

Next, a DNA fragment including a coding region for the kanamycin-resistance gene was amplified based on the PCR method using a pair of Primers F15 and R15 shown in Table 25 below, and further using pKD13 serving as a template. In that case, the primers F15 and R15 includes nucleotide sequences homologous to regions present upstream and downstream, respectively, of 5 the ldhA gene coding region in the chromosomal DNA of *E. coli*.

TABLE 25

| Primer name | Sequence and description | SEQ ID NO: |
|---|---|---|
| Primer F15 | 5'-CTGCCGGGAAATGACTGTCCGCA AGGAAAAGAGTGTGAGGAAAAACAAT GATTCCGGGGATCCGTCGACC-3' | 46 |
| Primer R15 | 5'-AAAGAAGTAATGTTTTCTTCATC ATCACCTCAGAAAAGATCGCTACGAG TTGTAGGCTGGAGCTGCTTCG-3' | 47 |

In the same manner as the above described manipulations for disruption of the pflB gene, the purified PCR product was transfected into the above competent cells to prepare an ldhA gene-deficient strain. In addition, deletion of the ldhA gene was confirmed by way of cultivation of transformants in predetermined culture media, followed by performing organic acid analysis on a supernatant separated from culture solution based on centrifugal manipulations, as described above. That is, in the organic acid analysis, a strain in which production of lactic acid had not been observed was obtained as the ldhA gene-deficient strain. In addition, removal of the kanamycin-resistance gene from the chromosomal DNA was also performed based on the method using pCP20 (Life Science Market) as described above, a colony showing sensitivity to kanamycin was selected, and the colony was named Strain BW25113ΔpflBΔldhA.

(3) Disruption of frdA Gene

The strain BW25113ΔpflBΔldhA obtained in the above way was transformed again with pKD46 (Life Science Market), and then, competent cells of the obtained transformant were prepared in the same manner.

Next, a DNA fragment including a coding region for the kanamycin-resistance gene was amplified based on the PCR method using a pair of Primers F16 and R16 shown in Table 26 below and further using pKD13 serving as a template. In that case, the primers F16 and R16 includes nucleotide sequences homologous to regions present upstream and downstream, respectively, of the coding region for the frdA gene in the chromosomal DNA of *E. coli*.

TABLE 26

| Primer name | Sequence and description | SEQ ID NO: |
|---|---|---|
| Primer F16 | 5'-ACCCTGAAGTACGTGGCTGTGGG ATAAAAACAATCTGGAGGAATGTCGT GATTCCGGGGATCCGTCGACC-3' | 48 |
| Primer R16 | 5'-GCACCACCTCAATTTTCAGGTTT TTCATCTCAGCCATTCGCCTTCTCCT TTGTAGGCTGGAGCTGCTTCG-3' | 49 |

In the same manner as the above-described manipulations for disruption of the pflB, the purified PCR product was transfected into the above competent cells to thereby prepare an frdA gene-deficient strain. In addition, deletion of the frdA gene was confirmed by way of cultivation of transformants in predetermined culture media, followed by performing organic acid analysis on a supernatant separated from culture solution based on centrifugal manipulations, in the same manner above. That is, in the organic acid analysis, a strain in which production of succinic acid had not been observed was obtained as the frdA gene-deficient strain. In addition, removal of the kanamycin-resistance gene from the chromosomal DNA was also performed based on the method using pCP20 (Life Science Market) as described above, a colony sensitive to kanamycin was selected, and the colony was named Strain BW25113ΔpflBΔldhAΔfrdA.

Test Example 4

The BW25113ΔpflBΔldhAΔfrdA strains obtained in the above way were transformed with pGEK004, pGE333 (ppcD229N/K813S), and pGE322 (ppcD229N/N917G) constructed in Test Example 1, respectively, based on an ordinary method, thereby obtaining various strains of predetermined recombinant *Escherichia coli* of the invention.

Each of the above various recombinant strains was precultured in 5 mL of an LB culture medium in a test tube. The resulting preculture was inoculated into 100 mL of Terrific culture medium (composition for 1 L of the culture medium: 12 g of bactotryptone, 24 g of yeast extract, 4 mL of glycerol, 2.31 g of $KH_2PO_4$, 12.54 g of $K_2HPO_4$) in a 500-mL flask, and then, this was subjected to shaking culture at 37° C. at 200 rpm for 20 hours. After the cultivation, the cells were centrifuged to remove the culture medium supernatant, and then, the obtained microbial cells were suspended in 40 mL of the BT solution, followed by adjustment of the OD value of the suspension to around 15-20. The suspension was transferred to a 100 mL medium bottle with a stirring bar placed therein, and then, 5 mL of 50% glucose and 5 mL of 2 M $(NH_4)_2CO_3$ were added thereto. The medium bottle was placed inside a thermostat bath set to 33° C., and was left to stand still, thereby performing a reaction while stirring the suspension. After 20 hours, 0.5 mL of the reaction solution was collected from the medium bottle, the collected reaction solution was subjected to centrifugation to thereby obtain a supernatant, and then, an amount of consumed glucose, and amounts of produced amino acids were measured. For identification and measurement of amino acids, an amino acid analysis system (SHIMADZU CORPORATION) was used.

Results

Figure 7:
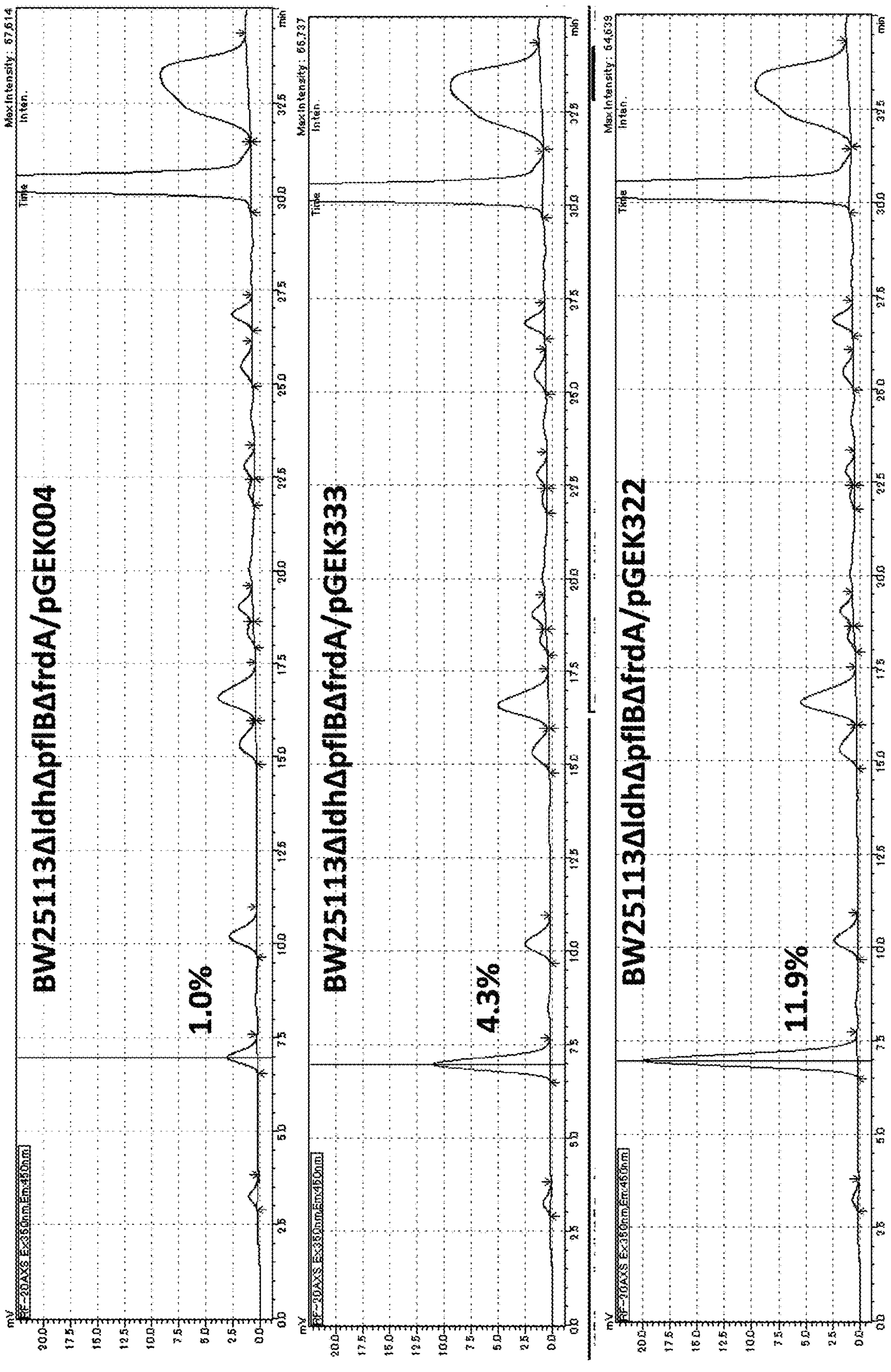
FIG. 7 is a diagram showing results of Test Example 4 in Examples.

The chromatograph obtained through the amino acid analysis is shown in FIG. 7. Additionally, in the chromatograph shown in FIG. 7, the peak appearing around 7 minutes is a peak for aspartic acid. Furthermore, in Table 27 below, genetic types of the obtained recombinant strains of *Escherichia coli*, aspartic acid production efficiencies (%) calculated in the test for production of aspartic acid, etc. are shown. A value of the aspartic acid production efficiency (%) is a ratio of aspartic acid that was actually produced, to 0.5 mol of glucose incorporated into the microbial cells. The value is a value based on the fact that, theoretically, 2 mol of aspartic acid can be produced from 1 mol of glucose.

TABLE 27

| Strain name | Amino acid substitutions in mutant-type PEPCs | Aspartate production efficiency (%) |
|---|---|---|
| BW25113ΔldhΔpflBΔfrdA/pGEK004 | — | 1.0 |
| BW25113ΔldhΔpflBΔfrdA/pGEK333 | D299N and K813S | 4.3 |
| BW25113ΔldhΔpflBΔfrdA/pGEK322 | D299N and N917G | 11.9 |

Also in this test example, in which the predetermined recombinant microorganism of the inventions were produced using *Escherichia coli*, the aspartic acid production efficiency of the strain BW25113ΔldhΔpflBΔfrdA/PGEK004, which served as a negative control, was at a remarkably poor level of 1%. On the other hand, with regard to the strain BW25113ΔldhΔpflBΔfrdA/PGEK333 having an amino acid substitution of a combination of D299N and K813S, and the strain BW25113ΔldhΔpflBΔfrdA/PGEK322 having an amino acid substitution of a combination of D299N and N917G, the aspartic acid production efficiencies of these microorganism showed values of 4.3% and 11.9%, respectively, and thus, significant improvements were recognized in the aspartic acid production efficiencies, exceeding four times that of the negative control. In particular, the strain BW25113ΔldhΔpflBΔfrdA/PGEK322 having an amino acid substitution of a combination of D299N and N917G, significant improvements were recognized in the aspartic acid production efficiency, exceeding 11 times that of the negative control. That is, according to this test example, it was shown that, also in predetermined recombinant microorganisms of the invention using *Escherichia coli* serving as a host, sugars can efficiently be converted into aspartic acid, and that the aspartic acid can significantly efficiently be produced.

From the results of Test Examples 1 to 4 above, it was shown that, according to the invention, production efficiency of aspartic acid or a metabolite produced in a metabolic pathway derived therefrom can be improved, thus improving the yield of a target substance. That is, it was revealed that, according to the invention, efficiency of conversion of a starting substrate, e.g., sugars, into a target substance can be improved, thus realizing energy saving, cost reduction, and efficient substance production in bioprocess.

Supplementary Notes

In Examples, there is also a step of using an In-Fusion cloning kit (Takara Bio Inc.) in cloning of various gene coding regions, promoter regions, and the like as described above, but regarding the primer pairs used at the time of PCR amplification, a supplemental description is given in which an appropriate adapter sequence is added to each 5'-terminal of forward/reverse primers according to the instructions of the cloning kit.

INDUSTRIAL APPLICABILITY

The invention has high industrial applicability in the fields of biotechnology, substance production, and the like.

The invention claimed is:

1. A reaction product comprising a target substance and a genetically modified microorganism, wherein the genetically modified microorganism belongs to the genus *Escherichia* or coryneform bacteria, and satisfying all of the following Conditions (I) to (III):

Condition (I): have an inactivated or disrupted chromosomal gene, the gene encoding a fumarate reductase catalyzing a conversion reaction from fumarate to succinate in a counterclockwise TCA cycle under reducing conditions or anaerobic conditions, and so that succinate dehydrogenase activity or fumarate reductase activity is reduced or inactivated relative to a wild-type unmodified microorganism, wherein the wild-type unmodified microorganism is a wild-type of the genetically modified microorganism;

Condition (II): have an inactivated or disrupted chromosomal lactate dehydrogenase gene so that lactate dehydrogenase activity is reduced or inactivated relative to the wild-type unmodified microorganism; and Condition (III): have an operable gene that encodes a mutant-type phosphoenolpyruvate carboxylase so that the genetically modified microorganism has modified phosphoenolpyruvate carboxylase activity showing resistance to feedback inhibition by aspartic acid in wild-type phosphoenolpyruvate carboxylase activity, or exogenous phosphoenolpyruvate carboxylase activity having higher resistance to feedback inhibition by aspartic acid than that of the wild-type phosphoenolpyruvate carboxylase activity shown by the wild-type unmodified microorganism, the mutant-type phosphoenolpyruvate carboxylase comprises SEQ ID NO: 2, with mutations including at least one amino acid substitution selected from the group consisting of: (a) an amino acid substitution at the position 299 with asparagine, (b) an amino acid substitution at the position 653 with glycine, (c) an amino acid substitution at the position 813 with serine or glycine, (d) an amino acid substitution at the position 869 with glycine, (e) an amino acid substitution at the position 873 with glycine or serine, and (f) an amino acid substitution at the position 917 with glycine, wherein the reaction product is obtained by:

(p) culturing the genetically modified microorganism in a reaction medium (X) comprising a sugar serving as a substrate, to produce the target substance, and the genetically modified microorganism is cultured so as to produce aspartic acid or a downstream metabolite from aspartic acid as the target substance via the counterclockwise TCA cycle under reducing conditions or anaerobic conditions;

wherein the reaction product is an intermediate product, whereby recovering of the target substance is achieved by harvesting the intermediate product containing the target substance, and wherein the genetically modified microorganism produces more aspartic acid or a downstream metabolite from aspartic acid as the target substance as compared to the wild-type unmodified microorganism.

2. The reaction product according to claim 1, wherein the genetically modified microorganism is further satisfying Condition (IV): pyruvate: quinone oxidoreductase is reduced or inactivated relative to the wild-type unmodified microorganism.

3. A method for producing a target substance, the method comprising:

(p) culturing a genetically modified microorganism in a reaction medium (X) comprising a sugar serving as a substrate, to produce a target substance; and (q) recovering the target substance from the reaction medium (X), wherein the genetically modified microorganism belongs to the genus *Escherichia* or coryneform bacteria, and is genetically modified:

(I) to have an inactivated or disrupted chromosomal gene, the gene encoding a fumarate reductase catalyzing a conversion reaction from fumarate to succinate in a counterclockwise TCA cycle under reducing conditions or anaerobic conditions;

(II) to have an inactivated or disrupted chromosomal lactate dehydrogenase gene; and (III) to have an operable gene that encodes a mutant-type phosphoenolpyruvate carboxylase showing increased resistance to feedback inhibition by aspartic acid as compared to a wild-type phosphoenolpyruvate carboxylase, in step (p), the genetically modified microorganism is cultured so as to produce aspartic acid or a downstream metabolite from aspartic acid as the target substance via the counterclockwise TCA cycle under reducing conditions or anaerobic conditions, and the mutant-type phosphoenolpyruvate carboxylase comprises SEQ ID NO: 2, with mutations including at least one amino acid substitution selected from the group consisting of: (a) an amino acid substitution at the position 299 with asparagine, (b) an amino acid substitution at the position 653 with glycine, (c) an amino acid substitution at the position 813 with serine or glycine, (d) an amino acid substitution at the position 869 with glycine, (e) an amino acid substitution at the position 873 with glycine or serine, and (f) an amino acid substitution at the position 917 with glycine, and wherein the genetically modified microorganism produces more aspartic acid or a downstream metabolite from aspartic acid as the target substance as compared to a wild-type unmodified microorganism, wherein the wild-type unmodified microorganism is a wild type of the genetically modified microorganism.

4. The method according to claim 3, wherein, in Step (p), the genetically modified microorganism is cultured in the reaction medium (X under reducing conditions where the genetically modified microorganism does not substantially proliferate, to produce the target substance.

5. The method according to claim 3, wherein an oxidation-reduction potential of the reaction medium (X) is a predetermined value within the range of −200 mV to −500 mV.

6. The method according to claim 3, wherein the reaction medium (X) comprises glucose serving as the substrate.

7. The method according to claim 3, wherein the genetically modified microorganism is precultured to proliferate under aerobic conditions in a predetermined culture medium (Y prior to the step (p).

8. The method according to claim 3, wherein the aspartic acid or the downstream metabolite from aspartic acid serving as the target substance is oxaloacetic acid or malic acid, which is an intermediate metabolite in the counterclockwise TCA cycle under reducing conditions or anaerobic conditions.

9. The method according to claim 3, wherein the target substance is aspartic acid, beta alanine, or asparagine.

10. A mutant-type phosphoenolpyruvate carboxylase comprising an amino acid mutation with respect to an amino acid sequence of a wild-type phosphoenolpyruvate carboxylase of a microorganism belonging to coryneform bacteria, the amino acid mutation being capable of reducing feedback inhibition by aspartic acid in the wild-type phosphoenolpyruvate carboxylase activity, wherein the amino acid mutation at least comprises: based on the amino acid sequence set forth in SEQ ID NO: 2, (g) an amino acid substitution of an amino acid corresponding to the 299th aspartic acid with asparagine;

(i) an amino acid substitution of an amino acid corresponding to the 813th lysine with a predetermined amino acid, wherein the substituted amino acid is not lysine; or (l) an amino acid substitution of an amino acid corresponding to the 917th asparagine with a predetermined amino acid, wherein the substituted amino acid is not asparagine, wherein the mutant-type phosphoenolpyruvate carboxylase has higher resistance to feedback inhibition by aspartic acid than that of a protein having only the amino acid substitution defined in (g), (i), or (1) above with respect to the amino acid sequence of the wild-type phosphoenolpyruvate carboxylase.

11. The mutant-type phosphoenolpyruvate carboxylase according to claim 10, wherein the mutant-type phosphoenolpyruvate carboxylase has an amino acid sequence set forth in in any one of the following (J), (K), and (L):

(J) an amino acid sequence obtained by introducing the amino acid substitution set forth in (g) above and the amino acid substitution set forth in (i) or (1) above into the amino acid sequence set forth in any one of SEQ ID NOs: 2 to 13;

(K) an amino acid sequence having deletion, substitution, and/or addition of one or more amino acids in the amino acid sequence defined in (J) above, wherein each of the above amino acid substitutions has been maintained; and (L) an amino acid sequence having a sequence identity of at least 60% to the amino acid sequence defined in (J) above, wherein each of the above amino acid substitutions has been maintained.

12. The mutant-type phosphoenolpyruvate carboxylase according to claim 11, wherein the amino acid sequence defined in (J) above is an amino acid sequence obtained by introducing the above amino acid substitution into the amino acid sequence set forth in SEQ ID NO: 2.

13. The mutant-type phosphoenolpyruvate carboxylase according to claim 10, wherein the mutant-type phosphoenolpyruvate carboxylase has an amino acid sequence obtained by introducing the above amino acid substitution into the amino acid sequence set forth in any one of SEQ ID NOs: 2 to 13.

14. A nucleic acid coding for the mutant-type phosphoenolpyruvate carboxylase according to claim 12.

15. The nucleic acid according to claim 14, wherein the nucleic acid is a DNA fragment.

16. A genetically modified microorganism into which the nucleic acid according to claim 14 is introduced.

17. The genetically modified microorganism according to claim 16, satisfying all of the following Conditions (I) to (III):

Condition (I): succinate dehydrogenase activity or fumarate reductase activity is reduced or inactivated relative to a wild-type microorganism corresponding to the genetically modified microorganism;

Condition (II): lactate dehydrogenase activity is reduced or inactivated relative to the wild-type microorganism; and Condition (III): the genetically modified microorganism has modified phosphoenolpyruvate carboxylase activity showing resistance to feedback inhibition by aspartic acid in wild-type phosphoenolpyruvate carboxylase activity, or exogenous phosphoenolpyruvate carboxylase activity having higher resistance to feedback inhibition by aspartic acid than that of the wild-type phosphoenolpyruvate carboxylase activity shown by the wild-type microorganism.

18. The genetically modified microorganism according to claim 17, further satisfying Condition (IV): pyruvate: quinone oxidoreductase is reduced or inactivated relative to the wild-type microorganism.

19. The reaction product according to claim 1, wherein the genetically modified microorganism is a genetically modified microorganism belonging to Gram-positive bacteria.

20. The reaction product according to claim 19, wherein the genetically modified microorganism is a genetically modified microorganism belonging to coryneform bacteria.

21. The reaction product according to claim 1, wherein the genetically modified microorganism is a genetically modified microorganism belonging to Gram-negative bacteria.

22. The reaction product according to claim 21, wherein the genetically modified microorganism is a genetically modified microorganism belonging to the genus *Escherichia.*

23. The reaction product according to claim 21, wherein the genetically modified microorganism is further satisfying Condition V): pyruvate formate-lyase activity is reduced or inactivated relative to the wild-type unmodified microorganism.

24. The method according to claim 3, wherein the genetically modified microorganism in Step (p) belongs to the genus *Escherichia*, and is genetically modified to have an inactivated or disrupted chromosomal pyruvate formate-lyase gene.

25. The method according to claim 3, wherein the genetically modified microorganism is genetically modified to have an inactivated or disrupted chromosomal pyruvate: quinone oxidoreductase gene.

26. The method according to claim 3, wherein the mutant-type phosphoenolpyruvate carboxylase comprises the amino acid substitution of (a) above and at least one selected from among the amino acid substations of (c), (e) and (f) above.

27. The method according to claim 3, wherein the genetically modified microorganism belongs to the coryneform bacteria, and the disrupted inactivated or disrupted chromosomal gene encoding the fumarate reductase in (I) above is at least one selected from the group consisting of sdhC, sdhA, sdhB and sdhD.

28. The method according to claim 27, wherein the genetically modified microorganism belongs to the genus *Corynebacterium.*

29. The method according to claim 3, wherein the genetically modified microorganism belongs to the genus *Escherichia*, and the inactivated or disrupted chromosomal gene encoding the fumarate reductase in (I) above is at least one gene selected from the group consisting of frdD, frdC, frdB and frdA.

30. The method according to claim 3, wherein the genetically modified microorganism belongs to the genus *Escherichia*, and is genetically modified to have an inactivated or disrupted chromosomal pyruvate formate-lyase gene.

* * * * *